US009845237B2

(12) United States Patent
Tseng et al.

(10) Patent No.: US 9,845,237 B2
(45) Date of Patent: Dec. 19, 2017

(54) SUPRAMOLECULAR APPROACH FOR PREPARATION OF SIZE CONTROLLABLE NANOPARTICLES

(75) Inventors: Hsian-Rong Tseng, Los Angeles, CA (US); Hao Wang, Los Angeles, CA (US); Shutao Wang, Los Angeles, CA (US); Helen Su, Torrance, CA (US); Caius G. Radu, Los Angeles, CA (US); Johannes Czernin, Pacific Palisades, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 13/148,869

(22) PCT Filed: Feb. 26, 2010

(86) PCT No.: PCT/US2010/025623
§ 371 (c)(1),
(2), (4) Date: Aug. 10, 2011

(87) PCT Pub. No.: WO2010/099466
PCT Pub. Date: Sep. 2, 2010

(65) Prior Publication Data
US 2011/0305685 A1 Dec. 15, 2011

Related U.S. Application Data

(60) Provisional application No. 61/299,753, filed on Jan. 29, 2010, provisional application No. 61/155,784, filed on Feb. 26, 2009.

(51) Int. Cl.
| | |
|---|---|
| A61K 39/395 | (2006.01) |
| A61K 31/7088 | (2006.01) |
| A61K 31/724 | (2006.01) |
| A61K 38/00 | (2006.01) |
| A61K 38/54 | (2006.01) |
| A61P 35/00 | (2006.01) |
| C07H 21/00 | (2006.01) |
| C07H 21/02 | (2006.01) |
| C07K 14/00 | (2006.01) |
| C07K 16/00 | (2006.01) |
| C07K 2/00 | (2006.01) |
| C08B 37/16 | (2006.01) |
| C12N 15/63 | (2006.01) |
| C12N 9/96 | (2006.01) |
| B82B 3/00 | (2006.01) |
| B82Y 30/00 | (2011.01) |
| B82Y 40/00 | (2011.01) |
| A61K 47/48 | (2006.01) |
| C08G 83/00 | (2006.01) |
| A61K 47/62 | (2017.01) |
| A61K 47/69 | (2017.01) |
| B82Y 5/00 | (2011.01) |

(52) U.S. Cl.
CPC .......... *B82B 3/00* (2013.01); *A61K 47/48238* (2013.01); *A61K 47/48861* (2013.01); *A61K 47/62* (2017.08); *A61K 47/6923* (2017.08); *B82Y 30/00* (2013.01); *B82Y 40/00* (2013.01); *C08G 83/008* (2013.01); *B82Y 5/00* (2013.01)

(58) Field of Classification Search
None
See application file for complete search history.

(56) References Cited

U.S. PATENT DOCUMENTS

| | | | |
|---|---|---|---|
| 6,509,323 B1 | 1/2003 | Davis et al. | |
| 6,767,635 B1 * | 7/2004 | Bahr et al. | 428/402 |
| 6,884,789 B2 | 4/2005 | Davis et al. | |
| 7,091,192 B1 | 8/2006 | Davis et al. | |
| 7,270,808 B2 | 9/2007 | Cheng et al. | |
| 8,357,377 B2 * | 1/2013 | Pun et al. | 424/400 |
| 2007/0117177 A1 * | 5/2007 | Luo et al. | 435/68.1 |
| 2007/0258907 A1 | 11/2007 | Davis | |

FOREIGN PATENT DOCUMENTS

| | | |
|---|---|---|
| CN | 1717209 A | 1/2006 |
| WO | WO-2007/008300 A2 | 1/2007 |

OTHER PUBLICATIONS

Chworos, et al. (2004) "Building Programmable Jigsaw Puzzles with RNA", Science (306(5704): 2068-72.*
Kass, et al. (1995) Hematologic Pathology, 9(3-4): 179-84 (Abstract Only).*
Wang, et al. (2009) Angew. Chem. Int. Ed., 48: 4344-48.*
Singh, et al. (2010) "Characterization of Cyclodextrin Inclusion Complexes—A Review", Journal of Pharmaceutical Science and Technology vol. 2 (3), 2010, 171-183.*
Ohlan, et al. "Synthesis and antimicrobial evaluation of urea inclusion complexes", Organic Communications, 1(2): 24-32.*
An et al., "Synthesis and biomedical applications of hollow nanostructures," Nano Today, vol. 4, p. 359-373, 2009.
Anderson et al., "Selective Photothermolysis: Precise Microsurgery by Selective Absorption of Pulsed Radiation," Science, vol. 220, p. 524-527, 1983.
Au et al., "A Quantitative Study on the Photothermal Effect of Immuno Gold Nanocages Targeted to Breast Cancer Cells," ACS Nano, vol. 2, p. 1645-1652, 2008.
Bartlett et al., "Effect of siRNA nuclease stability on the in vitro and in vivo kinetics of siRNA-mediated gene silencing," Biotech. Bioeng., vol. 97, pp. 909-921, 2007.
Bartlett et al., "Impact of tumor-specific targeting on the biodistribution and efficacy of siRNA nanoparticles measured by multimodality in vivo imaging," Proc Natl Acad Sci U S A, vol. 104, pp. 15549-15554, 2007.
Bartlett et al., "Insights into the kinetics of siRNA-mediated gene silencing from live-cell and live-animal bioluminescent imaging," Nucl. Acid Res., vol. 34, pp. 322-333, 2006.

(Continued)

*Primary Examiner* — Robert M Kelly

(74) *Attorney, Agent, or Firm* — Venable LLP; Henry J. Daley; Annette K. Kwok

(57) ABSTRACT

A supramolecular approach has been developed for preparation of size-controllable nanoparticles, from three different molecular building blocks.

23 Claims, 50 Drawing Sheets

(56) References Cited

OTHER PUBLICATIONS

Bartlett et al., "Physicochemical and biological characterization of targeted, nucleic acid-containing nanoparticles," Bioconjug Chem., vol. 18, pp. 456-468, 2007.

Batist, "Cardiac safety of liposomal anthracyclines," Cardiovasc. Toxicol., vol. 7, pp. 72-74, 2007.

Bazin et al., "Electrophoretic Silica-coating process on a nanostructured copper electrode," Chem. Commun., pp. 5004-5006, 2008.

Bellocq et al., "Synthetic biocompatible cyclodextrin-based constructs for local gene delivery to improve cutaneous wound healing," Bioconjugate Chemistry, vol. 15, pp. 1201-1211, 2004.

Bertin, et al., "Multifunctional polymeric nanoparticles from diverse bioactive agents," Journal of the American Chemical Society, vol. 128, pp. 4168-4169, 2006.

Biancaniello et al., "Colloidal Interactions and Self-Assembly Using DNA Hybridization," Physical Review Letters, vol. 94, pp. 058302-1-058302-4, 2005.

Boal et al., "Self-assembly of nanoparticles into structured spherical and network aggregates," Nature, vol. 404, pp. 746-748, 2000.

Boddy, "A phase I and pharmacokinetic study of paclitaxel poliglumex (XYOTAX), investigating both 3-weekly and 2-weekly schedules," Clin. Cancer Res., vol. 11, pp. 7834-7840, 2005.

Brust et al., "Synthesis of Thiol-derivatised Gold Nanoparticles in a Two-phase Liquid-Liquid System," J. Chem. Soc. Chem. Comm., p. 801-802, 1994.

Bull et al., "Self-assembled peptide amphiphile nanofibers conjugated to MRI contrast agents," Nano Letters, vol. 5, pp. 1-4, 2005.

Cai, et al, "Nanoplatforms for Targeted Molecular Imaging in Living Subjects," Small vol. 3, p. 1840, 2007.

Carlson et al., "Selective tumor cell targeting using low affinity, multivalent interactions," ACS Chem. Biol., vol. 2, pp. 119-127, 2007.

Chen et al., "Constructions, DNA wrapping and cleavage of a carbon nanotube-polypseudorotaxane conjugate," Chem. Commun., pp. 4106-4108, 2009.

Chen et al., "Immuno Gold Nanocages with Tailored Optical Properties for Targeted Photothermal Destruction of Cancer Cells," Nano Lett, vol. 7, p. 1318-1322, 2007.

Chen et al., "Surface properties, more than size, limits convective distribution of virus-sized particles and viruses in the central nervous system," J Neurosurg, vol. 103, pp. 311-319, 2005.

Cheng et al., "Nanopatterning self-assembled nanoparticle superlattices by moulding microdroplets," Nature Nanotechnology, vol. 3, p. 682-690, 2008.

Cheon et al., "Synergistically Integrated Nanoparticles as Multimodal Probes for Nanobiotechnology," Acc. Chem. Res., vol. 41, pp. 1630-1640, 2008.

Choi et al., "Renal clearance of quantum dots," Nat Biotechnol, vol. 25, p. 1165-1170, 2007.

Davis et al., "Cyclodextrin-based pharmaceutics: Past, present and future," Nat Rev Drug Discov 3, 1023-1035, 2004.

Davis et al., "Cyclodextrin-Containing Polymers for Gene Delivery," Journal of Inclusion Phenomena and Macrocyclic Chemistry, vo. 44, pp. 17-22, 2003.

Davis et al., "Drug Targeting: Focusing drug actions at target tissue sites 20.370S10 workshop," Nat. Rev. Drug Discov., vol. 7, pp. 771-782, 2008.

Dickerson et al., "Gold nanorod assisted near-infrared plasmonic photothermal therapy (PPTT) of squamous cell carcinoma in mice," Cancer Letters, vol. 269, p. 57-66, 2008.

Dong et al., "Engineering metal ion coordination to regulate amyloid fibril assembly and toxicity," Proceedings of the National Academy of Sciences of the United States of America, vol. 104, p. 13313-13318, 2007.

Dreher et al., "Tumor vascular permeability, accumulation, and penetration of macromolecular drug carriers," J. Natl Cancer Inst. vol. 98, pp. 335-344, 2006.

Elghanian et al., "Selective colorimetric detection of polyuncleotides based on the distance-dependent optical properties of gold nanoparticles," Science, vol. 277, p. 1078-1081, 1997.

Erbacher et al., "Gene transfer with synthetic virus-like particles via the integrin-mediated endocytosis pathway," Gene Ther, vol. 6, pp. 138-145, 1999.

Ferreira et al., "New opportunities: the use of nanotechnologies to manipulate and track stem cells," Cell stem cell, vol. 3, pp. 136-146, 2008.

Fukushima et al., "PEGylated Polyplex Micelles from Triblock Catiomers with Spatially Ordered Layering of Condensed pDNA and Buffering United for Enhanced Intracellular Gene Deliver," J. Am. Chem. Soc., vol. 127, pp. 2810-2811, 2005.

Gao et al., "In vivo cancer targeting and imaging with semiconductor quantum dots," Nat. Biotechnol., vol. 22, p. 969-976, 2004.

Gatter et al., "Transferrin receptors in human tissues: their distribution and possible clinical relevance," J. Clin. Pathol., vol. 36, pp. 539-545, 1983.

Glover et al., "Towards Safe, Non-Viral Therapeutic Gene Expression in Humans," Nat Rev, vol. 6, pp. 299-310, 2005.

Gobin et al., "Near-Infrared Resonant Nanoshells for Combined Optical Imaging and Photothermal cancer Therapy," Nano Lett, vol. 7, p. 1929-1934, 2007.

Govorov et al., "Generating heat with metal nanoparticles," Nano Today, vol. 2, p. 30-38, 2007.

Gratton et al., "The Pursuit of a Scalable Nanofabrication Platform for Use in Material and Life Science Applications," Acc. Chem. Res., vol. 41, p. 1685-1695, 2008.

Green et al., "A combinatorial polymer library approach yields insight into nonviral gene delivery," Accounts of Chemical Research 41, 749-759 , 2008.

Heath et al., "Nanotechnology and Cancer," Annu. Rev. Med., vol. 59, p. 251-265, 2008.

Heidel et al., "Administration in non-human primates of escalating intravenous doses of targeted nanoparticles containing ribonucleotide reductase subunit M2 siRNA," Proc. Natl Acad. Sci. USA, vol. 104, pp. 5715-5721, 2007.

Hleb et al., "LANTCET: elimination of solid tumor cells with photothermal bubbles generated around clusters of gold nanoparticles," Nanomed, vol. 3, p. 647-667, 2008.

Hong, "The binding avidity of a nanoparticle-based multivalent targeted drug delivery platform," Chem Biol., vol. 14, pp. 107-115, 2007.

Hu et al., "Efficient Near-IR Hyperthermia and Intense Nonlinear Optical Imaging Contrast on the Gold Nanorod-in-Shell Nanostructures," J Am Chem Soc, vol. 131, p. 14186-14187, 2009.

Hu-Lieskovan et al., "Sequence-specific knockdown of EWS-FLI1 by targeted, nonviral delivery of small interfering RNA inhibits tumor growth in a murine model of metastatic Ewing's sarcoma," Cancer Res., vol. 65, pp. 8984-8992, 2005.

Huang et al., "Cancer Cell Imaging and Photothermal Therapy in the Near-Infrared Region by Using Gold Nanorods," J Am Chem Soc, vol. 128, p. 2115-2120, 2006.

Huang et al., "Plasmonic photothermal therapy (PPTT) using gold nanoparticles," Lasers Med Sci, vol. 23, p. 217-228, 2008.

Huang et al., "Selective Photothermal Therapy for mixed Cancer Cells Using Aptamer-Conjugated Nanorods," Langmuir, vol. 24, p. 11860-11865, 2008.

Hwang et al., Cucurbit[7]uril: A simple macrocyclic, pH-triggered hydrogelator exhibiting guest-induced stimuli-responsive behavior. Angew. Chem. Int. Ed., vol. 46, pp. 210-213, 2007.

Ingram et al., "Poly-hetero-?-functionalized Alkanethiolate-Stabilized Gold Cluster Compounds," J. Am. Chem. Soc., vol. 119, p. 9175-9178, 1997.

Ito et al., "Comparison of Nanoparticle Size and Electrophoretic Mobility Measurements Using a Carbon-Nanotube-Based Coulter Counter, Dynamic Light Scattering, Transmission Electron Microscopy, and Phase Analysis Light Scattering," Langmuir, vol. 20, pp. 6940-6945, 2004.

Jain et al., "Noble Metals on the Nanoscale: Optical and Photothermal Properties and Some Applications in Imagining, Sensing, Biology, and Medicine," Acc Chem Res, vol. 41, p. 1578-1586, 2008.

(56) References Cited

OTHER PUBLICATIONS

Jun et al., "Chemical Design of Nanoparticle Probes for High-Performance Magnetic Resonance Imaging," Angew. Chem. Int. Ed., vol. 47, p. 5122-5135, 2008.
Jun et al., "Chemisches Design von leistungsfähigan Nanosonden für die Kernspintomographie," Angew. Chem., vol. 120, p. 5200-5213, 2008.
Kang et al., "Cancer-Cell Targeting and Photoacoustic Therapy Using Carbon Nanotubes as "bomb" Agents," Small, vol. 5, p. 1292-1301, 2009.
Kato et al., "A Liquid-Crystalline Polymer Network built by Molecular Self-Assembly through Intermolecular hydrogen Bonding," Angewandte chemie-International edition in English vol. 33, p. 16441645, 1994.
Katz et al., "Integrated Nanoparticle-Biomolecule Hybrid Systems: Syntheis, Properties, and Applications," Angew Chem Int Ed Engl, vol. 43, p. 6042-6108, 2004.
Khlebtsov et al., "Optical amplification oh photothermal therapy with gold nanoparticles and nanoclusters," Nanotechnology, vol. 17, p. 5167-5179, 2006.
Kim et al. "Strategies for Silencing Human Disease using RNA Interferences," Nat Rev, vol. 8, pp. 173-184, 2007.
Kim et al., "Designed Fabrication of Multifunctional Magnetic Gold Nanoshells and Their Application to Magnetic Resonance Imaging and Photothermal Therapy," Angewandte Chemie-International Edition, vol. 45, p. 7754-7758, 2006.
Kim et al., "Entrapment of Hydrophobic Drugs in nanoparticle Monolayers with Efficient Release into Cancer Cells," J. Am. Chem. Soc., vol. 131, p. 1360-1361, 2009.
Kirpotin et al., "Antibody targeting of long-circulating lipidic particles does not increase tumor localization but does increase internalization in animal models," Cancer Res., vol. 66, pp. 6732-6740, 2006.
Klajn et al., "Dynamic hook-and-eye nanoparticle sponges," Nat Chem, vol. 1, p. 733-738, 2009.
Kotaidis et al., "Caviation dynamics on the nanoscale," Appl Phys Lett, vol. 87, pp. 213102-1-312102-3, 2005.
Kumar et al., "Supramlecular-directed synthesis of RNA-mediated CdS/ZnS nanotubes," Chem. Commun., pp. 5433-5435, 2009.
Lal et al., "Nanoshell-Enabled Photothermal Cancer Therapy: Impending Clinical Impact," Acc Chem Res, vol. 41, p. 1842-1851, 2008.
Lapotko et al., "Method of laser activated nano-thermolysis for elimination of tumor cells," Cancer Lett, vol. 239, p. 36-45, 2006.
Lapotko et al., "Selective Laser Nano-Thermolysis of Human Leukemia Cells with Microbubbles Generated Around Cluster of Gold Nanoparticles," Laser Surg Med, vol. 38, p. 631-642, 2006.
Lee et al., "Dual-Mode Nanoparticle Probes for High-Performance Magnetic Resonance and Fluorescence Imaging of Neuroblastoma," Angew Chem Int Ed Engl, vol. 45, p. 8160-8162, 2006.
Li et al., "Cationic Supramolecules Composed of Multiple Oligoethylenimine-Grated ?-Cyclodextrins Threaded on a Polymer Chain for Efficient Gene Delivery," Adv. Mater., vol. 18, pp. 2969-2974, 2006.
Li, et al., "Cyclodextrin-based Supramolecular Architectures: Synthesis, Structures and applications for Drug and Gene Delivery" Advance Drug Delivery Reviews, vol. 60, No. 9, pp. 1000-1017, 2008.
Liang et al., "Polymorphism of DNA-anionic liposome complexes reveals hierarchy of ion-mediated interactions," Proc Natl Acad Sci U S A, vol. 102, pp. 11173-11178, 2005.
Lin et al., "One-Dimensional Plasmon Coupling by Facile Self-Assembly of Hold Nanoparticles into branched Chain Networks," Adv Mater, vol. 17, p. 2553-2559, 2005.
Liu et al., "In vivo biodistribution and highly efficient tumour targeting of carbon nanotubes in mice," Nat. Nanotech., vol. 2, pp. 47-52, 2007.
Liu et al., "Water-Soluble Supramolecular Fullerene Assembly Mediated by Metallobridged ?-Cyclodextrins," Angew. Chem. Int. Ed. Engl., vol. 43, p. 2690-2694, 2004.
Loo et al., "Nanoshell-Enabled Photonics-Based Imaging and Therapy of Cancer," Technol. Cancer Res. Treat, vol. 3, p. 33-40, 2004.
Lowery et al., "Immunoanoshells for Selective Photothermal Therapy," Clin Cancer Res, vol. 11, p. 9097s, 2005.
Lu et al., "Self-Assembly and tunable plasmonic property of gold nanoparticles on mercapto-silica microspheres," J Mater Chem, vol. 19, p. 4597-4602, 2009.
Ludden et al., "Molecular printboards: versatile platforms for the creation and positioning of supramolecular assemblies and materials," Chemical Society Reviews, vol. 35, pp. 1122-1134, 2006.
Mathias et al., "Self-Assembly Through Hydrogen Bonding: Preparation of a Supramolecular Aggregate Composed of Ten Molecules," Angewandte Chemie-International Edition in English, vol. 32, p. 1766-1769, 1993.
Matsumura et al., "A new concept of macromolecular therapies in cancer chemotherapy: mechanism of tumortropic accumulation of proteins and the antitumor agent SMANCS," Cancer Res., vol. 6, pp. 6387-6392, 1986.
Maye et al., "Mediator-Teomplate Assembly of Nanoparticles," J Am Chem Soc, vol. 127, p. 1519-1529, 2005.
Meyer et al., "Breathing Life into POlycations: Functionalization with pH-Responsive Endosomolytic Peptides and Polyethylene Glycol Enables siRNA Delivery," J. Am. Chem. Soc., vol. 130, pp. 3272-3273, 2008.
Meyer et al., "Template-directed synthesis employing reversible imine bond formation," Chem. Soc. Rev., vol. 36, pp. 1705-1725, 2007.
Mitragotri et al., "Physical approaches to biomaterial design," Nat Mater, vol. 8, p. 15-23, 2009.
Montet et al., "Multivalent effects of RGD peptides obtained by nanoparticle display," J. Med. Chem, vol. 49, pp. 6087-6093, 2006.
Napier et al., "Nanoparticle Drug Delivery Platform," Nanoparticle drug delivery platform. Polymer Reviews 47, 321-327, 2007.
Nel et al., "Understanding biophysicochemical interactions at the nano-bio interface," Nat Mater, vol. 8, p. 543-557, 2009.
Ng et al., "Engineering clustered Ligand Binding Into Nonviral Vectors: ?V?3 Targeting as an Example," Mol. Ther., vol. 17, pp. 828-836, 2009.
Nie et al., "Nanotechnology Applications in Cancer,".Annu. Rev. Biomed. Eng., vol. 9, p. 257-288, 2007.
Niemeyer, "Nanoparticles, Proteins, and Nucleic Acids: Biotechnology Meets Materials Science," Angewandte Chemie-International Edition, vol. 40, p. 4128-4158, 2001.
Niidome et al., "Gene Therapy Progress and Prospects: Nonviral vectors," Gene Ther., vol. 9, p. 1647-1652, 2002.
Nomura et al., "Effect of particle size and charge on the disposition of lipid carriers after intratumoral injection into tissue-isolated tumors," Pharm Res., vol. 15, pp. 128-132, 1998.
O'Neal et al., "Photo-thermal tumor ablation in mice using near infrared-absorbing nanoparticles," Cancer Lett, vol. 209, p. 171-176, 2004.
Ofir et al., "Polymer and biopolymer mediated self-assembly of gold nanoparticles," Chem Soc Rev, vol. 37, p. 1814-1825, 2008.
Pack et al., "Design and Development of Polymers for Gene Delivery," Nat. Rev. Drug Discov., vol. 4, p. 581-593, 2005.
Park et al., "DNA-programmable nanoparticle crystallization," Nature, vol. 451, pp. 553-556, 2008.
Park, et al., "Supramolecular Assembly of Cyclodextrin-Based Nanoparticles on Solid Surfaces for Gene Delivery", Langmuir, vol. 22 (20), pp. 8478-8484, 2006.
Peek et al., "Nanotechnology in vaccine delivery," Adv. Drug Deliv. Rev., vol. 60, p. 915-928, 2008.
Petter et al., "Cooperative Binding by Aggregated Mono-6-(alkylamino-?-cyclodextrins," J. Am. Chem. Soc., vol. 112, pp. 3860-3868, 1990.
Pitsillides et al., "Selective Cell Targeting with Light-Absorbing Microparticles and Nanoparticles," Biophys J, vol. 84, p. 4023-4032, 2003.

(56) References Cited

OTHER PUBLICATIONS

Pommier, "Camptothecins and topoisomerase I a foot in the door. Targeting the genome beyond topoisomerase I with camptothecins and novel anticancer drugs: importance of DNA replication, repair and cell cycle check points," Curr. Med. Chem. Anticancer Agents, vol. 4, pp. 429-434, 2004.

Popielarski et al., "A nanoparticle-based model delivery system to guide the rational design of gene delivery to the liver. 2. In vitro and in vivo uptake results," Bioconjug Chem., vol. 16, pp. 1071-1080, 2005.

Prata et al., "A new helper phospholipid for gene delivery," Chem. Commun., pp. 1566-1568, 2008.

Pun et al., "Cyclopdextrin-Modified Polyethylimine Polymers for GeneDelivery," Bioconjugate Chem, vol. 15, pp. 831-840, 2004.

Pun et al., "Development of a Nonviral Gene Delivery Vehicle for Systemic Application," Bioconjugate Chem, vol. 13, pp. 630-639, 2002.

Rahman et al., "Anthracycline-induced cardiotoxicity and the cardiac-sparing effect of liposomal formulation," Int. J. Nanomedicine, vol. 2, pp. 567-583, 2007.

Rawlings et al., "Families of Serine Peptidases," Meth. Enzymol., vol. 244, pp. 19-61, 1994.

Rekharsky et al., "Complexation Thermodynamics of Cyclopdextrins," Chem Rev, vol. 98, p. 1875-1917, 1998.

Richardson et al., "Experimental and Theoretical Studies of Light-to-Heat Conversion and Collective Heating Effects in Metal Nanoparticle Solutions," Nano Lett, vol. 9, p. 1139-1146, 2009.

Rosi et al., "Nanostructures in Biodiagnostics," Chem. Rev., vol. 105, pp. 1547-1562, 2005.

Shenhar et al., "Polymer-Mediated Nanoparticle Assembly: Structural Control and Applications," Adv. Mater., vol. 17, p. 657-669, 2005.

Skrabalak et al., "Gold Nanocages: Synthesis, Properties, and Applications," Acc Chem Res, vol. 41, p. 1587-1595, 2008.

Song et al., "Antibody mediated in vivo delivery of small interfering RNAs via cell-surface receptors," Nature Biotech., vol. 23, pp. 709-717, 2005.

Srinivasachari et al., "Versatile supramolecular pDNA vehicles via "click polymerization" of ?-cyclodextrin with oligoethyleneamines," Biomaterials, vol. 30, pp. 928-938, 2009.

Starkey et al., "New Two-Photon Activated Photodynamic Therapy Sensitizers Induce Xenograft Tumor Regressions after near-IR Laser Treatment through the Body of the Host Mouse," Clin Cancer Res, , vol. 14, p. 6564-6573, 2008.

Stoddart et al., "Chemical synthesis gets a fillip from molecular recognition and self-assembly processes," Proc. Natl. Acad. Sci. U S A, vol. 99, p. 4797-4800, 2002.

Sun et al., "Strategies for optimized radiolabeling of nanoparticles for in vivo PET Imaging," Advanced Materials, vol. 19, p. 3157-3162, 2007.

Sutton et al., "Functionalized micellar systems for cancer targeted drug delivery," Pharm. Res., vol. 24, pp. 1029-1046, 2007.

Torchilin et al., "Cell transfection in vitro and in vivo with nontoxic TAT peptide-liposome-DNA complexes," Proc Natl Acad Sci U S A, vol. 100, pp. 1972-1977, 2003.

Torchilin, "Recent advances with liposomes as pharmaceutical carriers," Nat. Rev. Drug Discov., vol. 4, pp. 145-160, 2005.

Troutman et al., "Biodegradable Plasmon Resonant Nanoshells," Adv Mater, vol. 20, p. 2604-2608, 2008.

Uziely, "Liposomal doxorubicin: antitumor activity and unique toxicities during two complementary Phase I studies," J. Clin. Oncol, vol. 13, pp. 1777-1785, 1995.

Venturoli et al., "Ficoll and dextran vs. globular proteins as probes for testing glomerular permselectivity: effects of molecular size, shape, charge and deformability," Am. J. Physiol. vol. 288, pp. F605-F613, 2005.

Wang et al., "A Supramolecular Approach for Preparation of Size-Controlled Nanoparticles," Angewandte Chemie International Edition, vol. 48, pp. 4344-4348, 2009.

Wang et al., "Gold Nanorod/Fe3O4 Nanoparticles "Nano-Pearl-Necklaces" for Simultaneous Targeting, Dual-Mode Imaging., and Photothermal Ablation of Cancer Cells," Angew Chem Int Ed Engl, vol. 48, p. 2759-2763, 2009.

Wenz et al., "Cyclodextrin rotaxanes and polyrotaxanes," Chemical Reviews, vol. 106, pp. 782-817, 2006.

Woodrow et al., "Intravaginal gene silencing using biodegradable polymer nanoparticles densely loaded with small-interfering RNA," Nat. Mater., vol. 8, pp. 526-533, 2009.

Written Opinion of the International Searching Authority issued in counterpart International Application No. PCT/US2010/025623 dated Sep. 30, 2010.

Xie et al., "Ultrasmall c(RGDyK)-Coated Fe3O4 nanoparticles and Their specific Targeting to Integrin AvB3-Rich Tumor cells," J. Am. Chem. Soc., vol. 130, pp. 7542-7543, 2008.

Yu et al., "Bioresponsive polymers for nonviral gene delivery," Curr. Opinion Mol. Ther., vol. 11, pp. 165-178, 2009.

Zamboni, "Liposomal, nanoparticle, and conjugated formulation of anticancer agents," Clin. Cancer Res, vol. 11, pp. 8230-8234, 2005.

Zhuang et al., "Controlling Colloidal Superparticle Growth Through Solvophobic Interactions," Angew Chem Int Ed Engl, vol. 47, p. 2208-2212, 2008.

Zugates et al., "Synthesis of Poly(?-amino ester)s with Thiol-Reactive Side Chains for DNA Delivery," J. Am. Chem. Soc., vol. 128, pp. 12726-12734, 2006.

Office Action issued in Chinese Application 201080016338.6, dated Jun. 20, 2013, with English translation.

\* cited by examiner

SUPRAMOLECULAR APPROACH FOR PREPARATION OF SIZE CONTROLLABLE NANOPARTICLES

CROSS-REFERENCE OF RELATED APPLICATION

This application is a National Stage Application under 35 U.S.C. §371 of PCT/US2010/025623, filed Feb. 26, 2010, the entire contents of which are hereby incorporated by reference which claims priority to U.S. Provisional Application No. 61/155,784, filed Feb. 26, 2009, the entire contents of which are hereby incorporated by reference and U.S. Provisional Application No. 61/299,753, filed Jan. 29, 2010, the entire contents of which are hereby incorporated by reference.

This invention was made with Government support of Grant No. U54 CA119347, awarded by the National Institutes of Health. The Government has certain rights in this invention.

BACKGROUND

Field of Invention

The invention relates to supramolecular structures, also called supramolecular nanoparticles (SNP) prepared using molecular recognition properties of building blocks. The invention also includes methods of producing supramolecular structures using molecular recognition and methods of controlling the size of the nanoparticles produced. The invention also includes methods of using the supramolecular structures to deliver genes, therapeutic compounds, and as photothermal therapy agents.

Discussion of Related Art

Nanoparticle therapeutics are typically particles comprised of therapeutic entities, such as small-molecule drugs, peptides, proteins and nucleic acids, and components that assemble with the therapeutic entities, such as lipids and polymers. Such nanoparticles can have enhanced anticancer effects compared with the therapeutic entities they contain. This is owing to more specific targeting to tumor tissues via improved pharmacokinetics and pharmacodynamics, as well as active intracellular delivery. These properties depend on the size and surface properties (including the presence of targeting ligands) of the nanoparticles Although an enormous amount of research is ongoing in the area, a majority portion of the work will not be translatable to the clinic. Some of the main obstacles include the use of immunostimulatory components, the use of components that have barriers to large-scale current good manufacturing practice (cGMP) production and/or hurdles in the development of well-defined chemistry, manufacturing and controls assays. A limited number of nanoparticle systems have achieved clinical applications, and information is becoming available to begin to understand some of the issues of moving these experimental systems into humans.

Over the past decades, there have been significant efforts devoted to explore the use of nanoparticles in the fields of biology and medicine. Several different types of nanoparticles have successfully made their ways into pre-clinical studies in animals, clinic trials in patients or even successful commercial products used in routine clinical practice. (Davis et al., *Nat. Rev. Drug Discov.* 2008, vol. 7, p. 771) For example, gold nanoshells (Loo et al., *Technol. Cancer Res. Trea*, vol. 3, p. 33, 2004), quantum dots (Gao et al., *Nat. Biotechnol.*, vol, 22, p. 969, 2004; Nie et al., *Annu. Rev. Biomed. Eng.*, vol. 9, p. 257, 2007) and super-paramagnetic nanoparticles, (Jun et al., *Angew. Chem.*, vol. 120, p. 5200, 20080; Jun et al., *Angew. Chem. Int. Ed.*, vol. 47, p. 5122, 2008) which carry target-specific ligands have been employed in in vivo cancer imaging; drug molecules can be packaged into polymer-based nanoparticles and/or liposomes (Heath et al., *Annu. Rev. Med.*, vol. 59, p. 251, 2008; Torchilin et al., *Nat. Rev. Drug Discov.*, vol. 4, p. 145, 2005) to achieve controlled released at disease sites (Napier et al., *Poly. Rev.*, vol. 47, p. 321, 2007; Gratton et al., *Acc. Chem. Res.*, vol. 41, p. 1685, 2008); positively charged nanoparticles can serve as a non-viral delivery system for both in vitro and in vivo genetic manipulation and programming (Davis et al., *Nat. Rev. Drug Discov.*, vol. 7, p. 771, 2008; Green et al., *Acc. Chem. Res.*, vol. 41, p. 749, 2008; Pack et al., *Nat. Rev. Drug Discov.*, vol. 4, p. 581, 2005). However, there remains an imperious desire for developing novel synthetic approaches in order to produce new-generation nanoparticles which have (i) controllable sizes and morphologies, (ii) low toxicity, compatible immunogenicity and in vivo degradability, and (iii) proper surface charges and chemistry for improved physiological stability and longer circulation time.

Noble-metal nanostructures with unique photophysical properties have been considered as prime-candidate agents for photothermal treatment of cancer (Anderson et al., *Science*, vol. 220, p. 524, 1983; Jain et al., *Acc Chem Res*, vol. 41, p. 1578, 2008; An et al., *Nano Today*, vol. 4, p. 359, 2009; Lal et al., *Acc Chem Res*, vol. 41, p. 1842, 2008). Typically, the photothermal properties of these nanostructures can be controlled by manipulating their sizes and shapes (Lal et al., *Acc Chem Res*, vol. 41, p. 1842, 2008; Skrabalak et al., *Acc Chem Res*, vol. 41, p. 1587, 2008). Over the past two decades, significant endeavors have been devoted to produce a variety of gold (Au) nanostructures, e.g., nanoparticles (Lapotko et al., *Laser Surg Medi*, vol. 38, p. 631, 2006; Huang et al., *Lasers Med Sci*, vol. 23, p. 217, 2008), nanoshells (Gobin et al., *Nano Lett*, vol. 7, p. 1929, 2007; Hu et al., *J Am Chem Soc*, vol. 131, p. 14186, 2009; Kim et al., *Angewandte Chemie-International Edition*, vol. 45, p. 7754, 2006), nanorods (Dickerson et al., *Cancer Letters*, vol. 269, p. 57, 2008; Huang et al., *Langmuir*, vol. 24, p. 11860, 2008) and nanocages (Skrabalak et al., *Acc Chem Res*, vol. 41, p. 1587, 2008; Chen et al., *Nano Lett*, vol. 7, p. 1318, 2007; Au et al., *ACS Nano*, vol. 2, p. 1645, 2008), which are able to overcome limitations of the organic dye-based photothermal agents (Huang et al., *Lasers Med Sci*, vol. 23, p. 217, 2008), such as low light absorption and undesired photobleaching. In order to harvest/generate sufficient energy to damage tumor cells, the sizes of these nanostructure-based agents are required in the range of tens to hundreds nm (Lowery et al., *Clin Cancer Res*, vol. 11, p. 9097s, 2005). However, the relatively "large" sizes of the agents often lead to poor bio-clearance (i.e., accumulation in liver, spleen and kidney), representing a major obstacle toward their in vivo applications (Mitragotri et al., *Nat Mater*, vol. 8, p. 15, 2009; Choi et al., *Nat Biotechnol*, vol. 25, p. 1165, 2007; Nel et al., *Nat Mater*, vol. 8, p. 543, 2009). Alternatively, the photophysical properties of noble-metal nanostructures can be systematically altered by forming aggregates via self assembly (Khlebtsov et al., *Nanotechnology*, vol. 17, p. 5167, 2006; Lu et al., *J Mater Chem*, vol. 19, p. 4597, 2009; Zhuang et al., *Angew Chem Int Ed Engl*, vol. 47, p. 2208, 2008; Troutman et al., *Adv Mater*, vol. 20, p. 2604, 2008; Ofir et al., *Chem Soc Rev*, vol. 37, p. 1814, 2008; Elghanian et al., *Science*, vol. 277, p. 1078, 1997; Lin et al., *Adv Mater*, vol. 17, p. 2553, 2005; Katz et al., *Angew Chem Int Ed Engl*, vol. 43, p. 6042, 2004; Cheng et al.,

*Nature Nanotechnology*, vol. 3, p. 682, 2008; Maye et al., *J Am Chem Soc*, vol. 127, p. 1519, 2005; Niemeyer, *Angewandte Chemie-International Edition*, vol. 40, p. 4128, 2001; Klajn et al., *Nat Chem*, vol. 1, p. 733, 2009). It has been observed (Lapotko et al., *Cancer Lett*, vol. 239, p. 36, 2006) that antibody-assisted aggregation of Au-nanoparticles on cell membranes or in intracellular environments led to the enhancement of photothermal performance, as a result of the collective effects (Govorov et al., *Nano Today*, vol. 2, p. 30, 2007; Richardson et al., *Nano Lett*, vol. 9, p. 1139, 2009) associated with the assembled structures. Therefore, self-assembly of small noble-metal building blocks, i.e., noble-metal colloids with the sizes (<8 nm) (Mitragotri et al., *Nat. Mater.*, vol. 8, p. 15, 2009; Choi et al., *Nat Biotechnol*, vol. 25, p. 1165, 2007; Nel et al., *Nat Mater*, vol. 8, p. 543, 2009) compatible with renal clearance, would provide a promising approach toward a new type of noble-metal photothermal agents.

Gene therapy generally requires delivery vehicles that are capable of (i) carrying/protecting genetic materials, e.g., DNA and siRNA, and (ii) target-specific delivery to desired tissues or subsets of cells (Kim et al. *Nat Rev Genet*, vol. 8, p.p. 173-184, 2007). Over the past decades, significant endeavors have been devoted to develop non-viral gene delivery vehicles (Glover et al., *Nat Rev Genet*, vol. 6, pp. 299-310, 2005; Rosi et al., *Chem. Rev.*, vol. 105, pp. 1547-1562, 2005) as alternatives to their viral counterparts, whose applications are restricted due to the potential safety issues and complex processes of preparation. Among the existing non-viral gene delivery systems (Niidome et al., *Gene Ther.*, vol. 9, p. 1647-1652, 2002; Prata et al., *Chem. Commun.*, pp. 1566-1568, 2008; Woodrow et al., *Nat. Mater.*, vol. 8, pp. 526-533, 2009; Chen et al., *Chem. Commun.*, pp. 4106-4108, 2009; Torchilin et al., *Proc Natl Acad Sci USA*, vol. 100, pp. 1972-1977, 2003), nanoparticle-based gene delivery vehicles (Liang et al., *Proc Natl Acad Sci USA*, vol. 102, pp. 11173-11178, 2005; Kumar et al., *Chem. Commun.*, pp. 5433-5435, 2009; Bazin et al., *Chem. Commun.*, pp. 5004-5006, 2008; Cheon et al., *Acc. Chem. Res.*, vol. 41, pp. 1630-1640, 2008) have received extensive attention. Nanoparticles have been regarded as promising transfection agents for effective and safe delivery of nucleic acids into specific type of cells or tissues, providing an alternative gene manipulation/therapy strategy to viral delivery. However, the slow, multistep synthetic approaches restrict the diversity of existing delivery materials, representing a major obstacle to achieving optimal transfection performance.

SUMMARY

Aspects of the invention include supramolecular structures, also called supramolecular nanoparticles (SNPs), having 1) a plurality of structural components that are suitable to at least provide some mechanical structure to said supramolecular structure; 2) plurality of binding components, each having a plurality of binding regions adapted to bind to said plurality of structural components; and 3) a plurality of terminating components, each of which is adapted to bind to a binding region of one of said plurality of binding components. The structural components and binding components self assemble when brought into contact to form a supramolecular structure. The terminating components act to occupy binding regions of the binding components to terminate further binding when the terminating components are present in a sufficient quantity relative to the binding regions of the binding components. In some embodiments, the structural component comprises a plurality of binding elements that bind to the binding regions of the binding components. In some embodiments, the terminating component has a single binding element that binds to one binding region on one binding component. In some embodiments, the supramolecular structure has two or more different terminating components.

In some embodiments, the binding regions (on the binding component) bind to the terminating components or structural components and form a molecular recognition pair.

In some embodiments, at least one of the structural component, binding component, or terminating component also has a functional element. In some embodiments, the supramolecular structure has two or more different functional elements.

In some embodiments, the supramolecular structure also includes a cargo.

Other aspects of the invention include methods of delivering a gene to a cell by contacting the cell with a supramolecular structure having a plasmid cargo.

Other aspects of the invention include methods of delivering a therapeutic compound to a cell by contacting the cell with a supramolecular structure having a therapeutic compound as cargo.

Other aspects of the invention include methods of producing supramolecular structures by preparing a suspension of structural components and binding components; and adding terminating components to said suspension. The ratio of an amount of structural components to binding components to terminating components are selected in accordance with a predetermined size of said supramolecular structures. The structural, binding and terminating components self assemble into said supramolecular structures having substantially said predetermined size.

BRIEF DESCRIPTION OF THE DRAWINGS

FIG. 9A shows In vivo biodistribution studies of the SNPs by systemically injecting the SNPs into mice via the tail veins. Left panel: 30-nm SNPs; right panel: 100-nm SNPs. FIG. 9B Lymph node trafficking studies of SNPs via front footpad injections. The 30- and 100-nm SNPs were injected respectively on different sides of footpads of a mouse. MicroPET/CT was carried out for 40 min (left panel) immediately after injection and also at 20 h post injection (right panel).

FIG. 11C shows a cartoon representation illustrating tail vein and footpad injections. FIGS. 11A and 11B show time-activity curves of mice that received the tail vein injection of the 30-nm and 100-nm SNPs, respectively. FIG. 11D shows the time-activity curve of mice that received the front footpad injection of the 30-nm and 100-nm SNPs.

FIGS. 15C and 15D show histograms summarizing the size distributions of 100-nm SNPs-DNA and 300-nm SNPs-DNA in dry states.

FIG. 17A shows cell viability of SNPs-DNA and RGD-SNPs-DNA transfected 3T3 cells along with non-treated 3T3 cells were determined by cell viability assay after 48 h of transfection. Error bars were obtained from three independent experiments. FIG. 17B shows the fluorescence microscope image of 100-5% RGD-SNPs-DNA transfected 3T3 cells after 48 h. The green and red fluorescence expressing cells were depicted as live and dead cells, respectively.

FIG. 19A shows EGFP transfection efficiency of a collection of SNPs-DNA and RGD-SNPs-DNA along with control delivery systems for two $\alpha_v\beta_3$ high-expressed cells (U87 and scraping-collected 3T3 cells) and two $\alpha_v\beta_3$ low-expressed cells (MCF7 and 0.25% trypsin-treated 3T3 cells). The representative fluorescence micrographs of 57±11% and 9±4% transfection efficiencies observed for 5 mol % (FIG. 19B) RGD-grafted 100-nm RGD-SNPs-DNA (100-5%)-treated $\alpha_v\beta_3$ high-expressed 3T3 cells and 1 mol % (FIG. 19C) RGD-grafted 300-nm RGD-SNPs-DNA (300-1%)-treated $\alpha_v\beta_3$ low-expressed 3T3 cells.

FIG. 21A shows 3D profile of gene transfection performance of RGD-SNPs-EGFP-DNA with variation of N/P ratios and RGD coverage. FIG. 21B shows 3D profile of gene transfection performance of TAT-SNPs-EGFP-DNA with variation of N/P ratios and TAT coverage. FIG. 21C shows 4D profile of gene transfection performance of TAT/RGD-SNPs-EGFP-DNA with variation of N/P ratios, RGD and TAT coverages. The XY, YZ and XZ plates across the best performance were simplified and denoted 2D contour images. FIG. 21D shows 4D profile of gene transfection performance of TAT/RGD-SNPs-FLuc-DNA with variation of N/P ratios, RGD and TAT coverages. The XY, YZ and XZ plates across the best performance were simplified and denoted 2D contour images.

FIGS. 22A and 22B show TEM and SEM images of the resulting SNPs with different sizes of 42±4, 86±9 and 160±13 nm. Scale bars: 100 nm. FIG. 22C shows dynamic light scattering (DLS) to measure SNP hydrodynamic sizes. FIG. 22D shows size-dependent zeta potentials variations of SNPs in PBS buffer (pH 7.2, containing 1.5 mM KH2PO4, 155 mM NaCl and 2.7 mM Na2HPO4).

FIG. 23A shows pH-dependent size variations of SNPs in the respective buffer solutions with pH values ranging from 4.05±0.03 to 8.23±0.03. Error bars are obtained from three measurements. FIG. 23B shows temperature-dependent size variation of both of the 40- and 80-nm SNPs in PBS buffer (pH=7.2) with different temperatures at rt, 37 and 60° C. FIG. 23C shows size variations of both 40- and 80-nm SNPs in presence and absence of 10% serum containing DMEM medium. Error bars are obtained from three measurements.

FIG. 27A shows Ad-grafted 2-nm Au colloids are the inorganic building blocks of Au-SNPs. FIG. 27B shows 118-nm Au-SNPs obtained via the supramolecular synthetic approach. FIG. 27C shows a titration plot summarizes the relationship between Au-SNP sizes and mixing ratios of the Au colloids and CD-PEI. FIG. 27D shows temperature and FIG. 27E shows pH effect on the stability of 118-nm Au-SNPs.

FIG. 29A shows the size variation of 40 and 118-nm Au-SNPs at different temperature ranging from 7 to 100° C. TEM histogram of 118-nm Au-SNPs at 25° C. (FIG. 29B), 50° C. (FIG. 29C) and 100° C. (FIG. 29D).

FIG. 31A shows Optical absorption spectra of 2-nm Au colloids and the 118-nm Au-SNPs. Time resolved bright-field micrographs of FIG. 31B shows 118-nm Au-SNPs suspension and FIG. 31C shows Ad-grafted 2-nm Au colloids suspension during the scanning of pulse laser (6 ns, 532 nm, 32 mJ/cm$^2$ for 118-nm Au-SNPs and 265 mJ/cm$^2$ for Ad-grafted 2-nm Au colloids).

FIG. 32A shows fluorescence micrographs of 118-nm RGD-Au-SNPs-treated U87 cells ($\alpha_v\beta_3$+). FIG. 32B shows fluorescence micrographs of 118-nm RGD-Au-SNPs-treated MCF7 cells ($\alpha_v\beta_3$-), and FIG. 32C shows fluorescence micrographs of RGD-grafted 2-nm Au colloids-treated U87 cells after irradiation of pulse laser (6 ns, 120 mJ/cm$^2$). A mask was employed to confine the laser beam diameter of 1 mm (as indicated by the white dashed circles).

FIG. 33A shows Fluorescence micrographs of a cell mixture containing 1:1 U87 and MCF7 cells. After treatment of RGD-Au-SNPs and sequential media exchange, the cell mixture was irradiated by pulse laser. In the laser irradiated region after 2 hr culture, U87 cells were depleted, while leaving MCF7 cells alive on the substrates. FIG. 33B shows Time-resolved images of a $\alpha_v\beta_3$-positive U87 cell with a 118-nm RGD-Au-SNPs grafted on its cellular protrusion. Upon irradiation of the 6-ns pulse laser (120 mJ/cm$^2$), fast contract of the cellular protrusion was observed as the result of the localized mechanical destruction caused by the formation of microbubbles.

DETAILED DESCRIPTION

Figure 1:
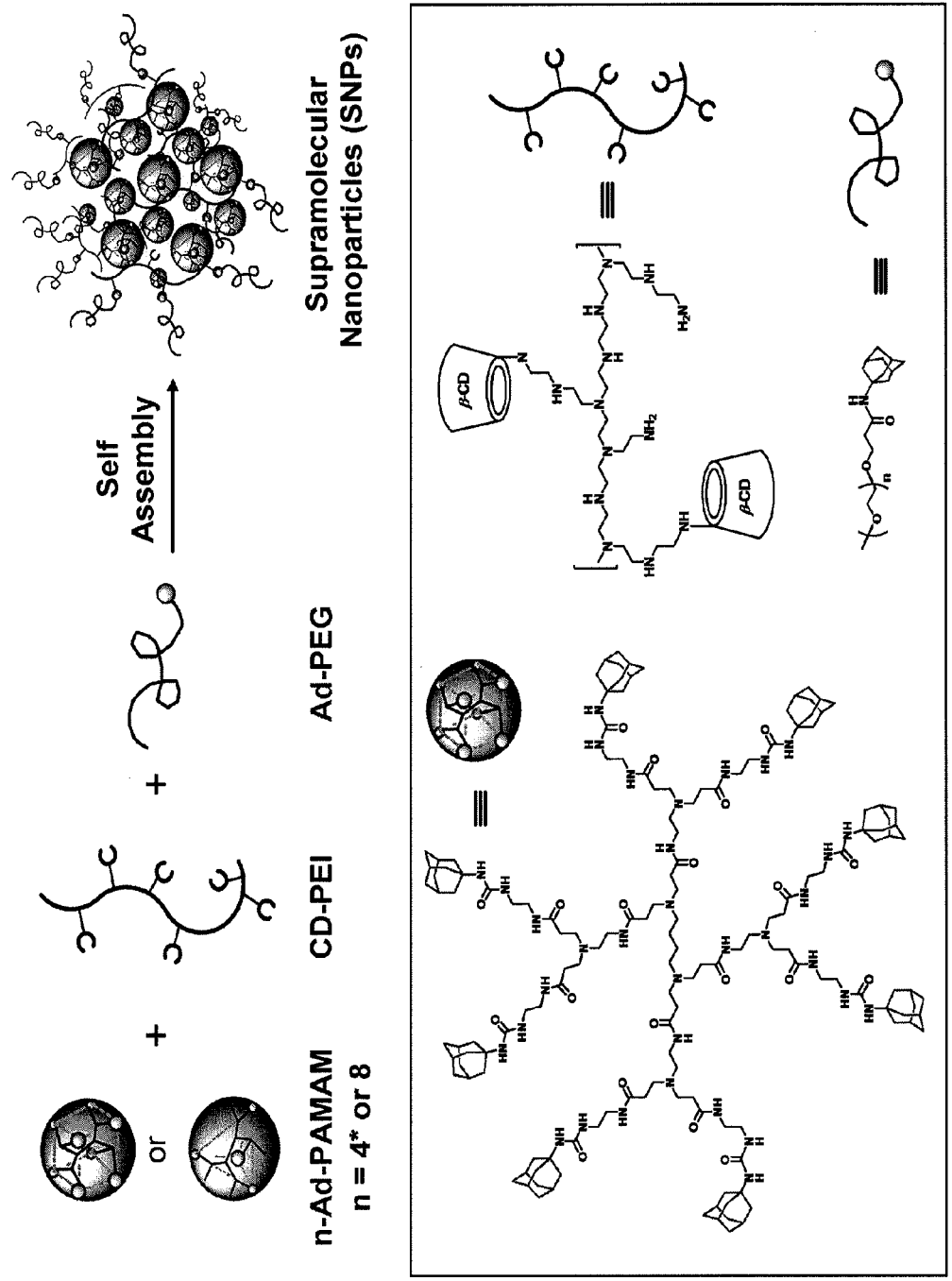
FIG. 1 shows graphical representations of a convenient, flexible and modular synthetic approach for preparation of size-controllable supramolecular nanoparticles (SNPs). A molecular recognition system based on adamantane (Ad) and β-cyclodextrin (CD) was employed to assemble three molecular building blocks (i) n-Ad-PAMAM, (n=4* or 8) (ii) CD-PEI, and (iii) Ad-PEG.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification are incorporated by reference as if each had been individually incorporated.

Some aspects of the invention include supramolecular structures, also called supramolecular nanoparticles (SNPs), having 1) a plurality of structural components that are suitable to at least provide some mechanical structure to the supramolecular structure; 2) a plurality of binding components, each having a plurality of binding regions adapted to bind to said plurality of structural components; and 3) a plurality of terminating components, each of which is adapted to bind to a binding region of one of said plurality of binding components. The structural components and binding components self assemble when brought into contact to form a supramolecular structure. The terminating components occupy binding regions of the binding components to terminate further binding when the terminating components are present in a sufficient quantity relative to the binding regions of the binding components.

The structural component binds to binding regions of the binding component. The structural component may bind to multiple binding regions of a single binding component, may bind to multiple binding components, or both. In general, the structural component binds to multiple binding regions on multiple binding components and spontaneously self-assembles, forming a crosslinked network or hydrogel between structural and binding components. The terminating component also binds to the binding region of the binding component. In this way, when the terminating component is present in sufficient concentration, the terminating component competes for binding regions on the binding component, thereby constraining the continuous propagation of the crosslinked network. In this way, the terminating component terminates growth of the crosslinked network and forms a discrete particle.

The at least three components bind to each other by one or more intermolecular forces. Examples of intermolecular forces include hydrophobic interactions, biomolecular interactions, hydrogen bonding interactions, π-π interactions, electrostatic interactions, dipole-dipole interactions, or van der Waals forces. Examples of biomolecular interactions include DNA hybridization, a protein-small molecule interaction (e.g. protein-substrate interaction (e.g. a streptavidin-biotin interaction) or protein-inhibitor interaction), an antibody-antigen interaction or a protein-protein interaction. Examples of other interactions include inclusion complexes or inclusion compounds, e.g. adamantane-β-cyclodextrin complexes or diazobenzene-α-cyclodextrin complexes. Generally, the intermolecular forces binding the components of the supramolecular structure are not covalent bonds.

Structural Component

In some embodiments, the structural component has a plurality of binding elements that bind to the binding regions of the binding components. The binding element is a chemical moiety that binds to the binding region of the binding component by one or more intermolecular forces. The binding element of the structural component and the binding region of the binding element are specifically selected to bind to each other, and may use molecular recognition properties to identify the binding regions.

In some embodiments, the structural component is at least one of an inorganic or organic core.

In some embodiments, inorganic cores include inorganic nanoparticles, such as metal nanoparticles (e.g. gold nanoparticles, silver nanoparticles, silicon nanoparticles, or other metals). Other inorganic nanoparticles include metal oxide nanoparticles (e.g. silica nanoparticles or iron oxide nanoparticles), and nanoparticles of other inorganic compounds. Functional nanoparticles may be used, such as, magnetic nanoparticles, quantum dots (e.g., CdS or CdSe nanoparticles), or semiconductive oxide particles.

In some embodiments, the inorganic core is spherical. In other embodiments, the morphology of the inorganic core may be triangular, cubic, star-like, rod-like, shell, diamond-like, plate-like, pyramidal, irregular or cage structure.

In some embodiments, the inorganic core has a maximum dimension of less than about 100 nm. The maximum dimension of the inorganic core may be less than about 70 nm, less than about 50 nm, less than about 25 nm, less than about 10 nm, or less than about 5 nm. The size of the inorganic core may vary based on the function of the supramolecular structure.

Where a range of values is provided in the present application, it is understood that each intervening value, to the tenth of the unit of the lower limit unless the context clearly dictates otherwise, between the upper and lower limit of that range and any other stated or intervening value in that stated range, is encompassed within the invention. The end values of any range are included in the range.

Numerous inorganic nanoparticles are known in the art. The inorganic core binds to binding regions of the binding component. In some embodiments, the binding component has binding regions that bind to the inorganic core directly. In other embodiments, the surface of the inorganic core is derivatized with a plurality of binding elements that bind to the binding regions of the binding component by one or more intermolecular forces.

In some embodiments, a plurality of inorganic core particles are present in the supramolecular structure. In such cases, the plurality of inorganic core particles bind with a plurality of binding components to form a crosslinked network or hydrogel. The continuous propagation of the crosslinked network is constrained or terminated by terminating components that also bind to the binding regions of the binding component.

In some embodiments, the structural component is an organic core. Organic cores include dendrimers, polymers, proteins, oligosaccharides, micelles, liposomes or vesicles. In some embodiments, the organic core is a dendrimer, polymer or polypeptide. In some embodiments, the structural component is a dendrimer (e.g. polyamidoamine dendrimer or PAMAM), branched polyethyleneimide (PEI), linear polyethyleneimide, polylysine, polylactide, polylactide-co-glycolide, polyanhydrides, poly-ε-caprolactones, polymethyl methacrylate, poly(N-isopropyl acrylamide) or polypeptide. In some embodiments, the organic core is a polyamidoamine dendrimer. In some embodiments, the organic core is a poly-L-lysine polymer.

In some embodiments, the binding regions of the binding component bind to binding elements present as part of the organic core structure. In other embodiments, the organic core is derivatized with a plurality of binding elements. The binding elements bind to the binding regions of the binding component by one or more intermolecular forces and self-assemble into a crosslinked network or hydrogel. The continuous propagation of the crosslinked network is constrained or terminated by terminating components that also bind to the binding regions of the binding component. The binding elements and binding regions may be selected based on the type of binding desired and may use molecular recognition properties in some embodiments.

Numerous dendrimers are known in the art. The advantage of dendrimer cores lies in their rapid synthesis, and easy ability to be functionalized with binding elements. The dendrimer may be synthesized to include binding elements as part of the structure. Alternatively, during dendrimer synthesis, a reactive functionality is present at each terminating point, which may be terminated with a chemical moiety that functions as a binding element to bind to the binding region of the binding component. Examples of specific dendrimers include polyamidoamine dendrimer or PAMAM.

Numerous polymers are known in the art. The advantage of polymer cores lies in their rapid synthesis and ability to be easily functionalized with binding elements. The polymer may be synthesized to include binding elements as part of the structure. Alternatively, reactive functional groups on a polymer may be derivatized with a chemical moiety that functions as a binding element. For example, polypeptides having lysine residues have reactive amine ($-NH_2$) groups which may be functionalized with binding elements. A specific example is poly-L-lysine.

In some embodiments, two or more different structural components are present, so long as both have binding elements that bind to the binding components.

In some embodiments, the structural component is a polyamidoamine dendrimer derivatized with a binding element, such as adamantane. In other embodiments, the structural component is an inorganic (for example, gold) nanoparticle derivatized with adamantane.

Terminating Component

The terminating components occupy binding regions of the binding components to constrain the continuous propagation of the crosslinked network when the terminating components are present in a sufficient quantity relative to the binding regions of the binding components. The binding component and structural component self-assemble into a supramolecular structure, while the terminating components occupy binding regions and prevent further self-assembly between the binding component and structural component. The extent to which the terminating component limits the self-assembly process is based on the relative concentration between the binding elements on the terminating components and the number of binding regions on the binding components. When the concentration of terminating components reaches a sufficient level, the self-assembly of the three components results in formation of a particle, rather than a crosslinked network or hydrogel. A benefit of this supramolecular approach to producing nanoparticles is that the size of the final particles may be readily adjusted by adjusting the relative concentrations of the components in the preparation mixture.

In some embodiments, the terminating component has a single binding element that binds to one of the binding regions on the binding component. In these cases, each terminating component has only one binding element. The binding element is a chemical moiety that binds to the binding region of the binding component by one or more intermolecular forces. These terminating components bind to only one binding region on the binding component. In this way, crosslinking between the terminating component and the binding component may be avoided.

In some embodiments, the terminating component is a polymer, polypeptide, oligosaccharide or small molecule, so long as the terminating component binds to a binding region of the binding component. In some embodiments, the terminating component is a polymer that is derivatized with a binding element. In some embodiments, the terminating component is poly(ethyleneglycol) derivatized with a binding element, such as adamantane.

In some embodiments, the supramolecular structure may have two or more terminating components. In these embodiments, the supramolecular structure may have 2, 3, 4, 5, or 6 different terminating components. Each terminating component may have the same binding element, or they may have different binding elements, but each binding element will bind to the binding region of the binding component.

Binding Component.

The binding component has a plurality of binding regions that bind to the structural component and the terminating component. The binding region is a chemical moiety that binds to the structural component and the terminating component by one or more intermolecular forces.

In some embodiments, two or more different binding components may be used, so long as both have binding regions that bind to the structural and terminating components.

In some embodiments, the binding component is a polymer, oligosaccharide, or polypeptide. Any suitable material may be used that includes a plurality of binding regions. In some embodiments, the binding component is a polymer. In some embodiments, the binding component is polyethylene imine or branched polyethylene imine derivatized with a plurality of binding regions. A specific example of a binding component is a branched polyethylene imine derivatized with β-cyclodextran. Another example of a binding component is poly-L-lysine derivatized with β-cyclodextran.

Molecular Recognition

In some embodiments, the binding regions and/or binding elements are molecular recognition elements. In other words, a binding region forms a molecular recognition pair with a binding element on either the structural component or the terminating component.

Molecular recognition refers to the specific interaction between two or more molecules through one or more intermolecular forces. The molecules involved in molecular recognition exhibit molecular complementarity, and are called a molecular recognition pair or host-guest complex. In this case, the terms "host" and "guest" do not impart any particular relationship, but only describe two compounds which exhibit molecular complementarity, i.e.; bind to each other by molecular recognition. A "host" and a "guest" bind to each other, while two "host" compounds do not. Molecular recognition is a specific interaction, meaning that each molecular recognition element will bind to complementary molecules having particular structural features. In general, molecular recognition pairs bind more tightly than nonspecific binding, since multiple interactions occur between the two molecular recognition elements.

Examples of molecular recognition pairs include small molecule host-guest complexes (including but not limited inclusion complexes), pairs of complementary olignucleotide sequences (e.g. DNA-DNA, DNA-RNA or RNA-RNA that bind to each other by hybridization), antibody-antigen, protein-substrate, protein-inhibitor, and protein-protein interactions (such as α-helical peptide chains and β-sheet peptide chains).

In some embodiments, the supramolecular structure self-assembles by molecular recognition. In this case, binding regions on the binding component form a molecular recognition pair with binding elements on the structural component. Binding elements on the terminating component also bind to binding regions on the binding component to form a molecular recognition pair. The molecular recognition pairs formed between the binding component and the structural component may be the same as the molecular recognition pair formed between the binding component and the terminating component, or they may be different. In other words, the binding element on the structural component may be the same as the binding element on the terminating component, or they may be different, but both binding elements bind to the same binding region on the binding component.

Specific examples of molecular recognition pairs include adamantane-β-cyclodextrin complexes or diazobenzene-α-cyclodextrin complexes. Other molecular recognition pairs include molecular complexes (e.g., steroid, pyrene, Rhodamine or doxorubicin in cyclodextrin) Other examples of molecular recognition pairs include biotin-streptavidin and complementary oligonucleotides.

Functional Elements

In some embodiments, at least one of the structural component, binding component or terminating component further includes a functional element. A functional element is a chemical moiety that imparts an additional function or activity to the supramolecular structure that is not present when the functional element is missing. In some embodiments, the functional element is a light emitting (i.e. fluorescent or phosphorescent) compound. Fluorescent and phosphorescent labeled supramolecular structures may be used, for example in imaging studies in vitro or in vivo. In other embodiments, the functional element may be a compound having a radioactive or magnetically active isotope. For example, positron emitting isotopes, such as $^{64}$Cu may be used to measure biodistribution of the supramolecular structures. Other suitable isotopes will be readily apparent to one of ordinary skill.

In some embodiments, the functional element is a targeting element that functions to target the supramolecular structure to particular cells. Such targeting elements include peptides, oligonucleotides, antibodies, and small molecules that bind to cell surface proteins. In general, any chemical moiety that specifically binds to one or more cell surface protein may be incorporated into the supramolecular structure. The cell surface proteins may be, for example, proteins on cancer cells or on bacteria or fungi. Specific examples of cell targeting moieties include RGD and EGF, folic acid, transferrin, and antibodies for targeting cell surface markers (e.g., Herceptin for Her2 on breast cancer cells).

In some embodiments, the functional element is a cell permeation element, that functions to increase cell membrane permeation. Specific examples of ligands that increase cell membrane permeation include the TAT ligand. Other cell membrane permeation ligands may also be used.

In some embodiments, the supramolecular structure has two or more functional elements. For example, the supramolecular structure may have two targeting elements, increasing cell targeting selectivity, or increasing binding affinity by targeting more than one cell surface protein. Other examples include supramolecular structures having a targeting element and a cell permeation element, combining the effects of improved cell targeting and increased cell permeation. Yet another example may be a supramolecular structure having an imaging element (light emitting or radioisotope) and targeting element for imaging targeted cells. Other combinations, such as two targeting elements and a cell permeation element, two targeting elements and a visualizing element, etc. may be readily envisioned.

In some embodiments, the supramolecular structure includes two or more terminating components, each of which may further include a functional element. In this way, multiple functional elements may be incorporated by using multiple terminating components. For example, a supramolecular structure may have a terminating component having no functional element and a terminating component having a targeting element. Terminating components having no functional element may be exchanged with terminating components having a functional element by treating the supramolecular structure with a second terminating component or mixture of other terminating components. Likewise, the supramolecular structure may be prepared using a mixture of terminating components, each of which will be incorporated into the supramolecular structure.

Cargo

In some embodiments, the supramolecular structure further includes a cargo. The cargo is a chemical moiety encapsulated within the supramolecular structure and released from the supramolecular structure. Cargo materials may bind to one or more of the structural component, binding component or terminating component, but do not interfere with self-assembly of the nanoparticle because they do not bind specifically to the binding regions of the binding component. The cargo compound may be a small molecule, such as a therapeutic compound (such as doxorubicin, taxol, rapamycin, or cis-platin for cancer therapy), protein, peptide, oligonucleotide (such as siRNA), or plasmid (for gene delivery). The supramolecular structures may deliver therapeutic proteins and oligonucleotides to a target cell, protecting the therapeutic compounds, proteins or oligonucleotides from degradation prior to delivery.

In some embodiments, the supramolecular structure may include two or more cargo compounds. In some instances, two or more therapeutic compounds may be incorporated, allowing for delivery of a defined ratio of therapeutic compounds to a cell by adjusting the ratio of the therapeutic compound in the supramolecular structure. In other instances, a plasmid and small molecule may be incorporated. Other combinations may also be used.

Preparation

Embodiments of the invention include methods for preparing the supramolecular structures described above by preparing a suspension of structural components and binding components; and adding terminating components to said suspension. The ratio of an amount of structural components to binding components to terminating components are selected in accordance with a predetermined size of said supramolecular structures. The structural, binding and terminating components self assemble into said supramolecular structures having substantially said predetermined size. In some embodiments, the predetermined size is at least about 30 nm and less than about 500 nm.

The supramolecular structures may be readily prepared by combining the components together. The at least three components self-assemble into the supramolecular structure. Additional components (structural, binding or terminating) or cargo compounds may also be used, so long as the minimum elements are present. The additional components may include one or more functional elements.

After the supramolecular structure is formed, components may be exchanged with other components bearing appropriate binding elements or binding regions by treating the supramolecular structure with additional components. For example, terminating components may be exchanged by treating the supramolecular structure with other terminating components (for example, bearing a functional element). Likewise, structural or binding components may be exchanged by treating the supramolecular structure with additional structural or binding components. A suspension or solution of the components may be sonicated to accelerate or assist in component exchange reactions.

The size of the supramolecular structures may be easily adjusted by varying the ratios between the components used to prepare the supramolecular structures. A wide variety of supramolecular structures of different sizes may be easily prepared. This also enables combinatorial synthesis, as arrays of supramolecular structures may be assayed based on their specific function to optimize their activity.

Using component exchange, the size of the supramolecular structures may be adjusted after the supramolecular structures are formed by treating the pre-formed supramolecular structures with additional component. For example, if the pre-formed supramolecular structure is treated with additional binding component, the size will decrease. If the pre-formed supramolecular structure is treated with additional structural component, the size will increase. Examples of this effect are presented in the Examples below.

The supramolecular structures can be disassociated in vitro and in vivo environments according to some embodiments of the current invention.

Functional elements may also be easily adjusted using this method. In many cases, components bearing a functional element may be included in the mixture used to prepare the supramolecular structure. The extent to which the functional elements are present in the supramolecular structure may be readily adjusted by changing the ratio between components having a functional element and components without. For example, if the functional element is present on the binding component, the ratio of the binding component having the functional element and the binding component lacking the functional element determines the extent to which the functional element is present in the supramolecular structure formed. The same holds true when the functional element is present on the terminating component or structural component.

When functional elements are present on terminating components, previously assembled supramolecular structures may be treated with terminating component(s) having a functional element. A portion of the terminating components will exchange to produce a supramolecular structure bearing the functional element(s). Multiple terminating components bearing multiple different functional elements may be added in a similar manner. The extent to which the functional element is present on the resulting supramolecular structure is determined by the concentration of the terminating component used to treat the pre-formed supramolecular structure.

Individual components may be readily prepared using chemistry known in the art. The binding elements are selected based on the type of intermolecular forces desired for binding the components together, and may be selected at will. Molecular recognition provides numerous examples of chemical moieties that may be used as binding elements or binding regions. For structural components, inorganic cores may be derivatized using methods known in the art to provide binding elements on the surface, when needed. Organic compounds, such as polymers and dendrimers, may be synthesized with suitable binding elements. Alternatively, organic cores, including polymers, dendrimers, polypeptides, etc. may be prepared bearing reactive functional groups, that may be derivatized with suitable binding elements or binding regions as desired.

Numerous methods exist for derivatizing organic compounds with suitable binding elements. For example, reactive functional groups on organic compounds, such as hydroxyls, thiols, amines, carboxylic acids, halides, alkenes, alkynes, azides, and others may be reacted or activated to react with a variety of other functional groups to form covalent bonds. For example, amine-bearing compounds having a free $NH_2$ group may be reacted with binding elements bearing amine-reactive groups such as isocyanates, isothiocyanates, and activated esters, such as N-hydroxysuccinimide (NHS) esters. In this way, binding elements may be readily added to any component. The number of binding elements on a particular component may be varied based on the number of reactive sites, and the amount of the reactive binding element used to prepare the component. For specific examples, see the Examples described below.

For example, amines on branched polyethyleneimine may be reacted with an activated cyclodextran, such as tosylated cyclodextran to prepare a binding component of polyethylene imine derivatized with cyclodextran (CD-PEI in Example 1). Analogously, other polymers, such as poly-L-lysine, may be reacted with an activated cyclodextran, such as tosylated cyclodextran to prepare a component of poly-L-lysine derivatized with cyclodextran binding elements. In other Examples, amines, such as those in polyamidoamine dendrimers or in poly-L-lysine may be reacted with other activated binding elements, such as adamantine isocyanate, to prepare components derivatized with adamantane binding elements.

Chemistry commonly used to derivatize proteins may also be used to add binding elements to proteins, peptides, or antibodies. For example, amine-coupling or thiol-ene coupling can be used to generate irreversible bonds.

In some cases a linker may be required. Various bifunctional crosslinkers are known to those in the art for covalently bonding to proteins, any of which may be used. For example, heterodifunctional crosslinkers such as succinimidyl-4-[N-maleimidomethyl]cyclohexane-1-carboxylate (SMCC) and melaimidobutyryloxysuccinimide ester (GMBS) may be used to react with amines (via the succinimide esters), and then form a covalent bond with a free thiol (via the maleimide). Other crosslinkers, such as succinimidyl 3-(2-pyridyldithio)-propionate (SPDP) may react with amines (via the succinimide ester), and form a covalent bond with a free thiol via thiol exchange. Other difunctional crosslinkers include suberic acid bis(N-hydrosuccinimide ester), which can react with two amines. Other bifunctional and heterobifunctional crosslinkers useable with various surface modifications will be evident to those of skill in the art.

In some embodiments of the invention, it is desirable to include a reversible (cleavable) linker, a variety of which will be evident to a skilled worker. For example, 4-allyloxy-4-oxo-butanoic acid has an alkene group on one end that can be used for thiol-ene coupling to thiol, and its other end is a carboxylic group that can be coupled to an amine. There is an ester group in the middle of the linker that should hydrolyze slowly over time under physiological conditions. Other cleavable cross-linkers will be evident to a skilled worker. These include, e.g., disulfide bonds which will cleave upon reduction.

Uses

The supramolecular structures have a variety of uses, particularly in biological applications. The simple methods required to produce the supramolecular structures enable rapid preparation of supramolecular structures of various sizes, or bearing specific functional elements. The use of different materials for structural, binding, and terminating components enables a wide variety of utilities.

The supramolecular structures can be disassociated in vitro and in vivo environments according to some embodiments of the current invention. This enables release of cargo materials from the supramolecular structure.

The supramolecular structures may be used for gene therapy (in vivo) or for cellular transfection (in vitro) by delivering genes or plasmids to cells.

Embodiments of the invention include methods of delivering a gene to a cell by contacting the cell with a supramolecular structure described herein, bearing a plasmid cargo. Treating the cell with the supramolecular structure results in internalization of the supramolecular structure, followed by release of the plasmid into the cell. This can result in effective "transfection" of the targeted cell with the plasmid of interest. In general, any plasmid, bearing any gene may be introduced into the cell in this manner. Likewise, targeting and/or cell permeation elements may improve cell specificity and/or internalization.

Embodiments of the invention include methods of delivering therapeutic compounds by treating a cell with a supramolecular structure described herein, having a therapeutic compound as cargo. The therapeutic compound may be, for example, a protein or peptide (including antibodies), an oligonucleotide (e.g., siRNA) or a small molecule. The small molecule may be, for example, an anti-cancer (e.g. doxorubicin, taxol, paclitaxel, cis-platin, or rapamycin), antibiotic, anti-bacterial, or anti-fungal agent. Functional elements on the supramolecular structure may improve cell targeting, internalization, or distribution. More than one therapeutic compound may be delivered in a single supramolecular structure, and if desired, the ratio of therapeutic compounds may be controlled.

Other methods of using the supramolecular structures described herein include methods of photothermotherapy by treating cells with supramolecular structures described herein having gold nanoparticles as structural components.

Other methods of using the supramolecular structures described herein include cell, protein or peptide sorting by treating cells, proteins or peptides with supramolecular structures having magnetic nanoparticles as structural components. Targeting functional elements allow the supramolecular structures to bind to specific cells, proteins or peptides, allowing magnetic separation.

The supramolecular nanoparticles may be used for molecular imaging (e.g. PET), using components bearing functional elements having one or more suitable isotopes or light emitting compounds. Likewise, supramolecular structures may be used for radiotherapy where one or more components includes a functional element having a therapeutic isotope. Cell targeting and cell permeation functional elements may further improve the effectiveness of these supramolecular structures.

Pharmaceutical Compositions

The supramolecular structures or nanoparticles discussed herein can be formulated into various compositions, for use in diagnostic or therapeutic treatment methods. The compositions (e.g. pharmaceutical compositions) can be assembled as a kit. Generally, a pharmaceutical composition of the invention comprises an effective amount (e.g., a pharmaceutically effective amount) of a composition of the invention.

A composition of the invention can be formulated as a pharmaceutical composition, which comprises a composition of the invention and pharmaceutically acceptable carrier. By a "pharmaceutically acceptable carrier" is meant a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. For a discussion of pharmaceutically acceptable carriers and other components of pharmaceutical compositions, see, e.g., Remington's Pharmaceutical Sciences, 18$^{th}$ ed., Mack Publishing Company, 1990. Some suitable pharmaceutical carriers will be evident to a skilled worker and include, e.g., water (including sterile and/or deionized water), suitable buffers (such as PBS), physiological saline, cell culture medium (such as DMEM), artificial cerebral spinal fluid, or the like.

A pharmaceutical composition or kit of the invention can contain other pharmaceuticals, in addition to the compositions of the invention. The other agent(s) can be administered at any suitable time during the treatment of the patient, either concurrently or sequentially.

One skilled in the art will appreciate that the particular formulation will depend, in part, upon the particular agent that is employed, and the chosen route of administration. Accordingly, there is a wide variety of suitable formulations of compositions of the present invention.

Formulations which are suitable for topical administration directly in the CNS include, e.g., suitable liquid carriers, or creams, emulsions, suspensions, solutions, gels, creams, pastes, foams, lubricants, or sprays. Topical administration in the CNS is possible when the CNS is opened by wound or during a surgery.

One skilled in the art will appreciate that a suitable or appropriate formulation can be selected, adapted or developed based upon the particular application at hand. Dosages for compositions of the invention can be in unit dosage form. The term "unit dosage form" as used herein refers to physically discrete units suitable as unitary dosages for animal (e.g. human) subjects, each unit containing a predetermined quantity of an agent of the invention, alone or in combination with other therapeutic agents, calculated in an amount sufficient to produce the desired effect in association with a pharmaceutically acceptable diluent, carrier, or vehicle.

One skilled in the art can easily determine the appropriate dose, schedule, and method of administration for the exact formulation of the composition being used, in order to achieve the desired effective amount or effective concentration of the agent in the individual patient.

The dose of a composition of the invention, administered to an animal, particularly a human, in the context of the present invention should be sufficient to effect at least a detectable amount of a diagnostic or therapeutic response in the individual over a reasonable time frame. The dose used to achieve a desired effect will be determined by a variety of factors, including the potency of the particular agent being administered, the pharmacodynamics associated with the agent in the host, the severity of the disease state of infected individuals, other medications being administered to the subject, etc. The size of the dose also will be determined by the existence of any adverse side effects that may accompany the particular agent, or composition thereof, employed. It is generally desirable, whenever possible, to keep adverse side effects to a minimum. The dose of the biologically active material will vary; suitable amounts for each particular agent will be evident to a skilled worker.

Another embodiment of the invention is a kit useful for any of the methods disclosed herein, either in vitro or in vivo. Such a kit can comprise one or more of the compositions of the invention. Optionally, the kits comprise instructions for performing the method. Optional elements of a kit of the invention include suitable buffers, pharmaceutically acceptable carriers, or the like, containers, or packaging materials. The reagents of the kit may be in containers in which the reagents are stable, e.g., in lyophilized form or stabilized liquids. The reagents may also be in single use form, e.g., in single dosage form.

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

Terms listed in single tense also include multiple unless the context indicates otherwise.

The examples disclosed below are provided to illustrate the invention but not to limit its scope. Other variants of the invention will be readily apparent to one of ordinary skill in the art and are encompassed by the appended claims. All publications, databases, and patents cited herein are hereby incorporated by reference for all purposes.

Methods for preparing, characterizing and using the compounds of this invention are illustrated in the following Examples. Starting materials are made according to procedures known in the art or as illustrated herein. The following examples are provided so that the invention might be more fully understood. These examples are illustrative only and should not be construed as limiting the invention in any way.

EXAMPLES

Example 1—Preparation of Supramolecular Nanoparticles (SNPs)

General

Reagents and solvents were purchased from Sigma-Aldrich (St. Louis, Mo.) and used as received without further purification otherwise noted. Branched polyethylenimine (PEI, MW=10 kD) was purchased from polysciences Inc (Washington, Pa.). Polymers contain primary, secondary, and tertiary amine groups in approximately 25/50/25 ratio. $1^{st}$-generation polyamidoamine dendrimer (PAMAM) with 1,4-diaminobutane core and amine terminals in 20% wt methanol solution was purchased from Dendritic Nanotechnologies, Inc (Mount pleasant, MI). 1-Adamantanamine hydrochloride and β-cyclodextrin (β-CD) were purchased from TCI America (San Francisco, Calif.). N-hydroxysuccinimide (NHS) functionalized methoxyl polyethylene glycol (mPEG-NHS, MW=5 kD) was obtained from NANOCS Inc (New York, N.Y.). 1,4,7,10-Tetraazacyclododecane-1,4,7,10-tetraacetic acid mono(N-hydroxysuccinimide ester) (DOTA-NHS) was purchased from Macrocycles (Dallas, Tex.). 6-Mono-tosyl-β-cyclodextrin (6-OTs-β-CD) was prepared according to literature reported method (R. C. Petter, J. S. Salek, C. T. Sikorski, G. Kumaravel, F. T. Lin *J. Am. Chem. Soc.* 1990, 112, 3860-3868). Dry $CH_2Cl_2$ was obtained by refluxing in $CaH_2$ and freshly distilled before use.

$^1$H NMR spectra were recorded on a Bruker Avance 400 spectrometer in deuterated solvents. Mass spectra were acquired using an Applied. Biosystems Voyager DE-STR MALDI-TOF mass spectrometer (Framingham, Mass., USA). Dynamic light scattering was performed on a Coulter N4 Plus Submicron Particle Sizer (Beckman Coulter, Inc., USA). Zeta potentials of the supramolecular nanoparticles (SNPs) were measured on Zetasizer Nano instrument (Malvern Instruments Ltd., United Kingdom). Transmission electron microscope (TEM) was measured on Philips CM 120 electron microscope operating with an acceleration voltage of 120 kV.

Synthesis of Building Blocks

Figure 34:
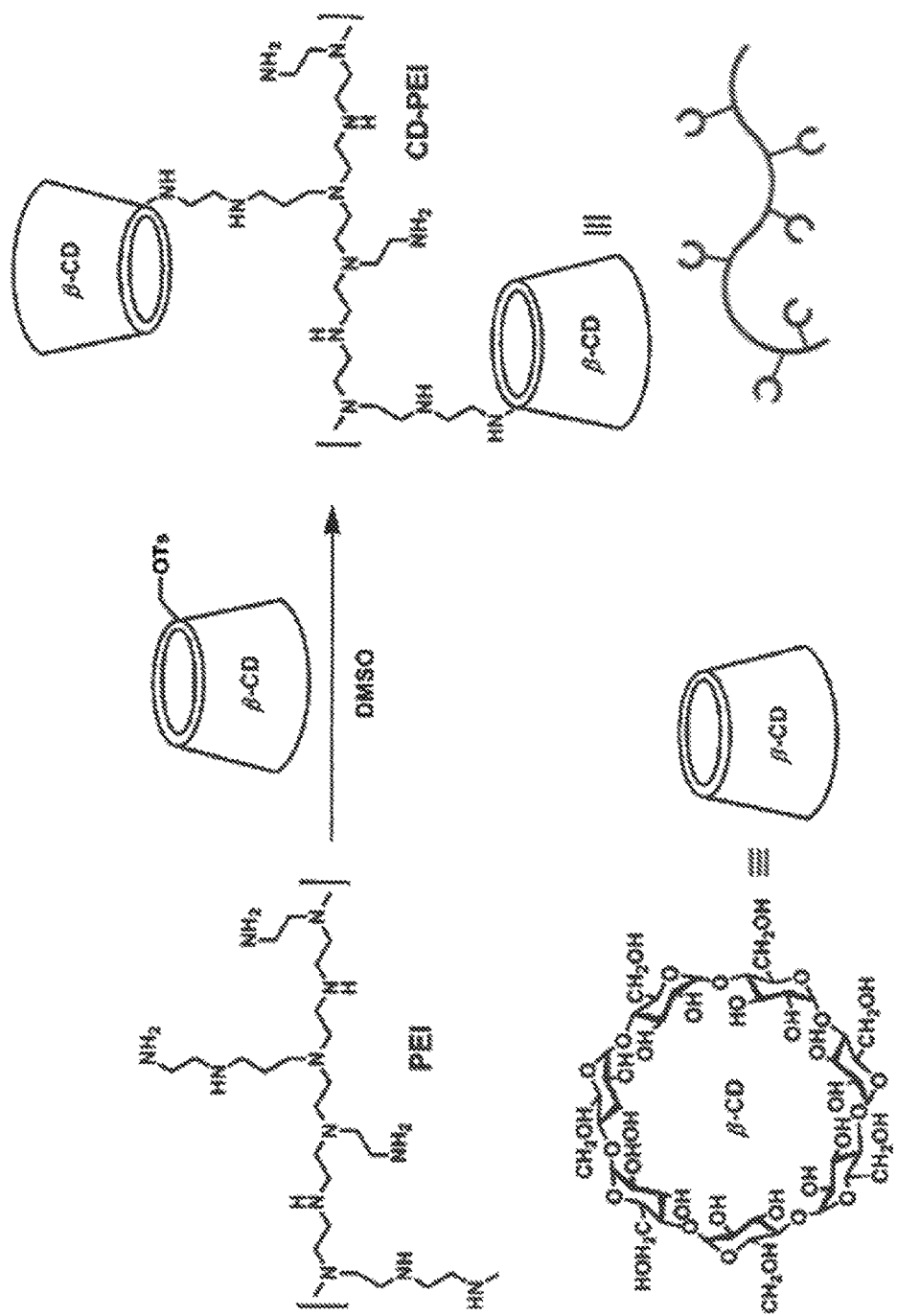
FIG. 34 shows the synthesis of CD-PEI and 6-OTs-β-CD.

Synthesis of CD-PEI (FIG. 34)

To a solution of branched PEI (100 mg, 10 μmol in 100 ml DMSO, 6-OTs-β-CD (1.29 g, 1 mmol) was added. After reaction at 70° C. for 3 days, the mixture was transferred to a Slide-A-Lyzer® dialysis cassette (MWCO, 10 kD) and dialyzed against deionized (DI) water for 6 days. After dialysis, the reaction mixture was filtrated to remove the unreacted 6-OTs-β-CD as white precipitate, and the filtrate was lyophilized overnight to afford CD-PEI (150 mg, 8.3 μmol) as a white floppy solid in 83% yield. $^1$H NMR (400 MHz, $D_2O$) δ 4.92 (br, $C_1\underline{H}$ of CD), 3.27-3.66 (m, $C_{2\text{-}6}\underline{H}$ of CD), 2.3-3.0 (br, $OC\underline{H}_2$ of PEI). The CD/PEI ratio in a CD-PEI molecule was calculated based on the proton integration of $C_1H$ of CD versus $CH_2$ of PEI.

Figure 35:
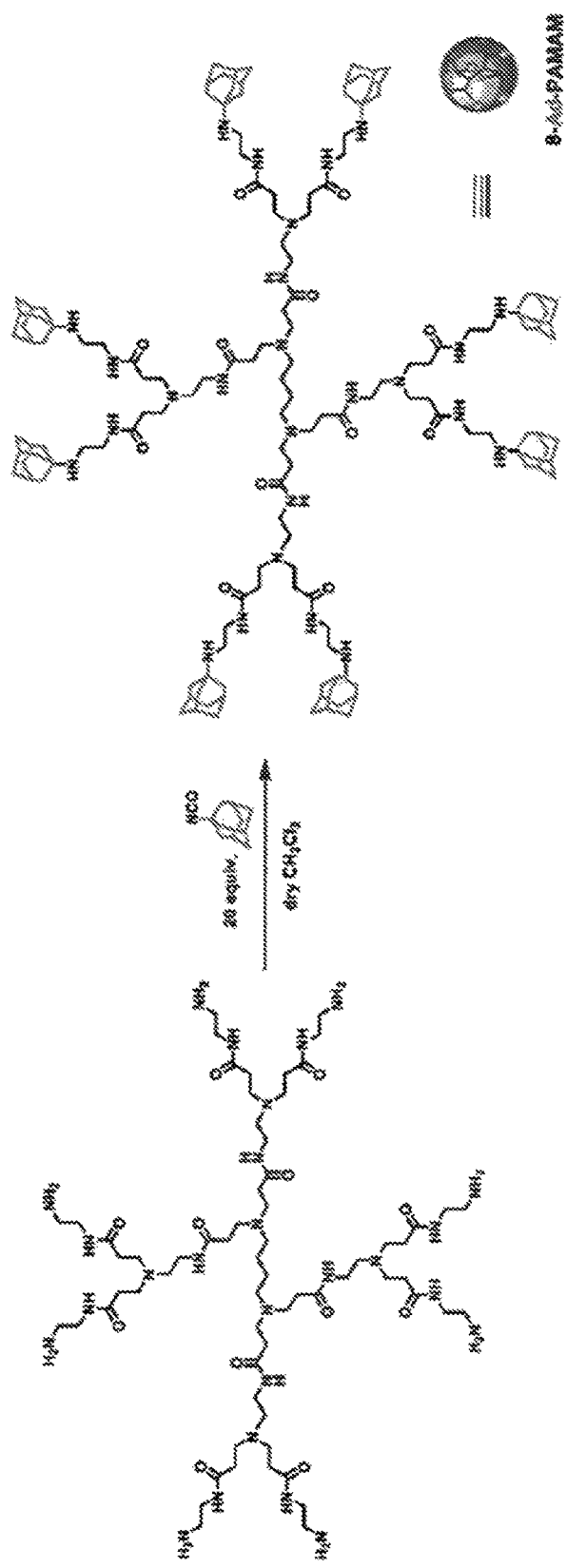
FIG. 35 shows the synthesis of 8-Ad-PAMAM from PAMAM and 8-Ad-PAMAM.

Synthesis of 8-Ad-PAMAM (FIG. 35)

A methanol solution containing PAMAM (20% wt, 100 mg, 0.069 mmol) was added into a round-bottom flask. Methanol was evaporated in vacuo and the sticky solid was redissolved in 10 ml dry THF. 1-adamantane isocyanide (244.6 mg, 1.38 mmol) in 10 ml dry THF was directly added the PAMAM solution. After the reaction mixture was stirred at rt for 2 h, the solvent was removed in vacuo. Ether (100 ml) was added to the reaction residue to generate a white precipitate, which was collected through filtration. The white precipitate was washed with ether (100 ml×3), and dried to give 8-Ad-PAMAM (169 mg, 0.059 mmol) as a white solid in 85% yield. $^1$HNMR (400 MHz, $CDCl_3$): δ 7.82-7.98 (m, 8H, CON$\underline{H}$), 6.10 (s, 4H, N$\underline{H}$CONH), 5.37 (s, 4H, NHCON$\underline{H}$), 3.24 (br, 32H, COC$\underline{H}_2$), 2.34-2.76 (m, 68H, NC$\underline{H}_2$), 1.64-2.03 (m, 120H, protons on Ad). ESI-MS: calcd. for $C_{152}H_{252}N_{34}O_{20}$ $[M+H]^+$: m/z=2875.98. found: 2875.78.

Figure 36:
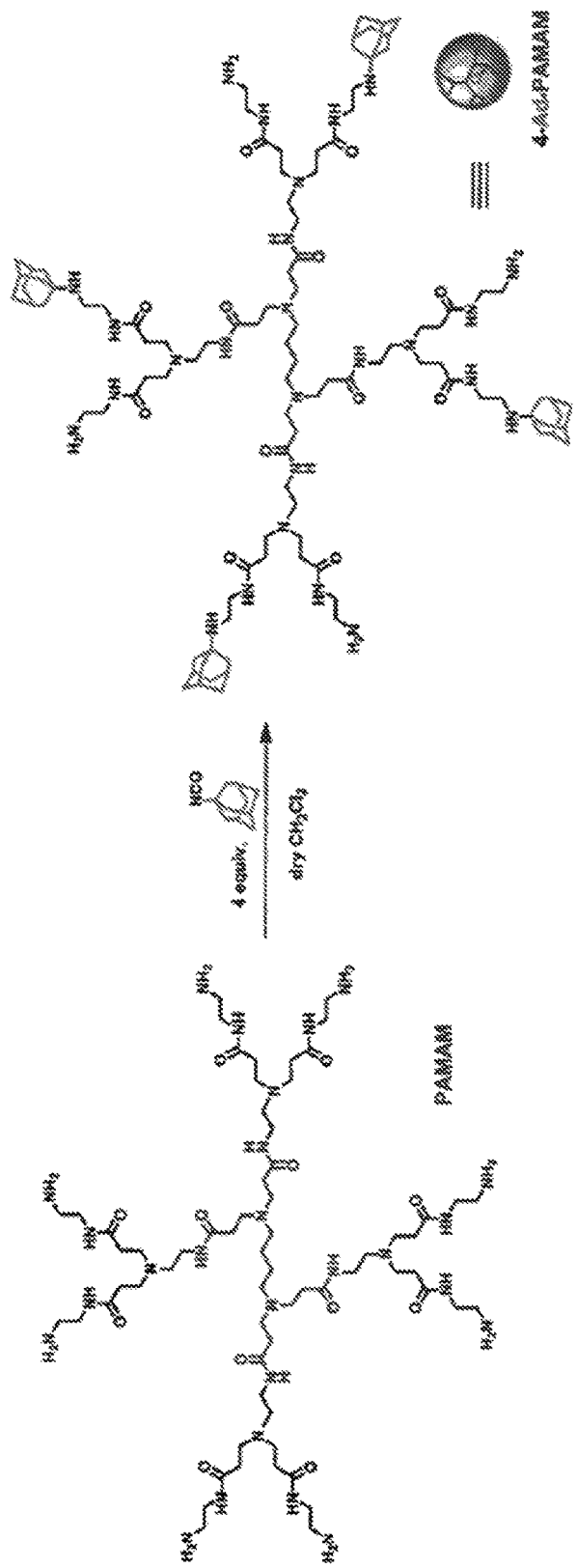
FIG. 36 shows the synthesis of 4-Ad-PAMAM from PAMAM and 4-Ad-PAMAM.

Synthesis of 4-Ad-PAMAM (FIG. 36)

To a 10-ml THF solution containing PAMAM (100 mg, 0.069 mmol), a 10-ml dry THF solution containing 1-adamantane isocyanide (50.1 mg, 0.283 mmol) was slowly added through a syringe pump (with an injection rate of 10 ml $h^{-1}$). After purification by precipitation from ether, 4-Ad-PAMAM (89.7 mg, 0.041 mmol) was obtained as a white solid in 60% yield. $^1$H NMR (400 MHz, $CDCl_3$): δ 7.83-7.95 (m, 8H, CON$\underline{H}$), 6.14 (s, 2H, N$\underline{H}$CONH), 5.42 (s, 2H, NHCON$\underline{H}$), 3.35 (br, 32H, COC$\underline{H}_2$), 2.35-2.81 (m, 68H, $NCH_2$), 1.60-2.01 (m, 60H, protons on Ad). ESI-MS: calcd. for $C_{108}H_{192}N_{30}O_{16}$ $[M+H]^+$: m/z=2167.52. found: 2167.18.

Figure 37:
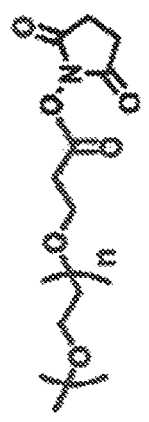
FIG. 37 shows the synthesis of Ad-PEG from 1-adamantanamine hydrochloride and mPEG-NHS.
Figure 37:
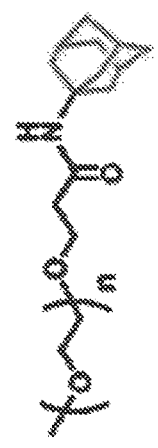
Figure 37:
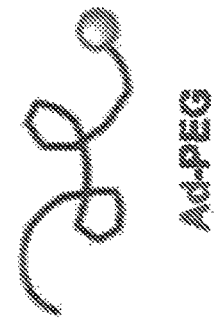

Synthesis of Ad-PEG (FIG. 37)

To a solution of 1-adamantanamine hydrochloride (187.7 mg, 1 mmol, 5 equiv.) in 10 ml $CH_2Cl_2$, triethylamine (105 mg, 1.04 mmol, 5.1 equiv.) and mPEG-NHS (1 g, 0.2 mmol, 1 equiv.) was added in sequence. The reaction mixture was stirred at rt for 2 h. After the reaction, the solvent was subsequently removed in vacuo, and water was added to the reaction residue. The solution was transferred into a centrifuge tube and centrifuged at 10,000 rpm for 10 min to remove the unreacted 1-adamantanamine. The solution was dialyzed with Slide-A-Lyzer® dialysis cassette (MWCO, 2 kD) against water overnight and lyophilized to yield Ad-PEG (0.92 g, 0.18 mmol) a white powder in 91% yield. $^1$H NMR (400 MHz, DMSO-$d_6$): δ 3.42-3.54 (br, 440H, OC$\underline{H}_2$), 1.13-1.18 (br, 15H, protons on Ad).

Nanoparticle Preparation

Preparation of SNPs

To a solution of Ad-PEG (6.3 mg, 1.26 μmol, 5 equiv.) in 750 μL DI water or PBS buffer, variable amount of n-Ad-PAMAM in 15-μL DMSO was slowly injected via a Hamilton under vigorous stirring. 750-μL of DI water or PBS buffer containing CD-PEI (4.3 mg, 0.25 μmol, 1 equiv.) was sequentially added into the mixture to obtain SNPs with different sizes from 30 to 450 nm. See FIG. 1.

Dynamic Light Scattering

DLS experiments were performed with a Coulter N4 Plus DLS instrument equipped with a 10-mW helium-neon laser (λ=632.8 nm) and thermoelectric temperature controller. Measurements were taken at a 90° scattering angle. SNPs samples for DLS were diluted with respective solution to make 90°-scattering intensities in the range from $5\times10^4$ to $1\times10^6$ counts per S. The sizes and the standard derivations of assembled SNPs were calculated by average values of at least three times measurements. For the temperature-dependent experiments, each sample was equilibrated at different temperatures for >20 min.

Zeta Potential (ζ) Measurements

Figure 2:
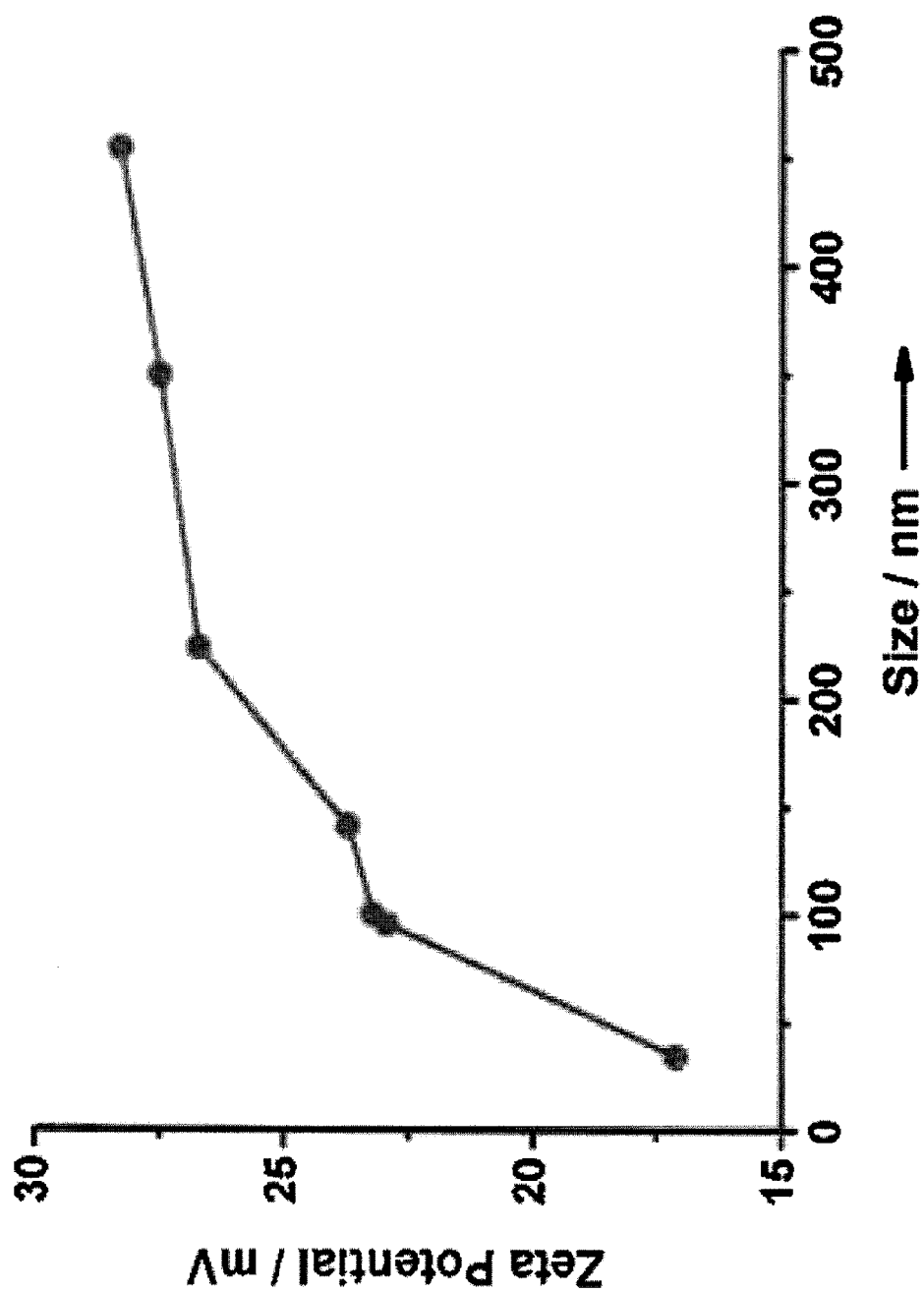
FIG. 2 shows size-dependent zeta potentials variations of SNPs in PBS buffer (pH 7.2)

Zeta potentials of SPNs were determined by photon correlation spectroscopy using a Zetasizer Nano instrument, (Malvern Instruments, Malvern, Worcestershire, UK). The measurements were performed at 25° C. with a detection angle of 90°, and the raw data were subsequently correlated to Z average mean size using a cumulative analysis by the Zetasizer software package. All analyses were performed on samples appropriately diluted with filtered DI water. Through multivalent Ad/CD recognition interactions, the ammonium groups in CD-PEI and 8-Ad-PAMAM endow the SNPs with positive charges. The zeta potentials were increased from 17.1 to 28.3 mV with increase of the diameter of SNPs from 30 to 450 nm (FIG. 2).

Transmission Electron Microscopy (TEM)

The morphology and sizes of SNPs were directly examined using transmission electron microscope. The studies were carried out on a Philips CM 120 electron microscope, operating at an acceleration voltage of 120 kV. The TEM samples were prepared by performing drop-coating of 2-μL SNPs solutions onto carbon-coated copper grids. After contacting the droplets with copper grids for 45 s, excess amount of droplets were removed by filter papers. Subsequently, the surface-deposited SNPs were negatively stained with 2% uranyl acetate for 45 before the TEM studies. As shown in FIGS. 3B-E, TEM images suggest that the SNPs exhibit the spherical shapes and narrow size distributions (FIG. 4), which are consistent to those observed by DLS.

Stability of SNPs (Based on the Octa-Substituted PAMAM Dendrimer 8-Ad-PAMAM)

Figure 4:
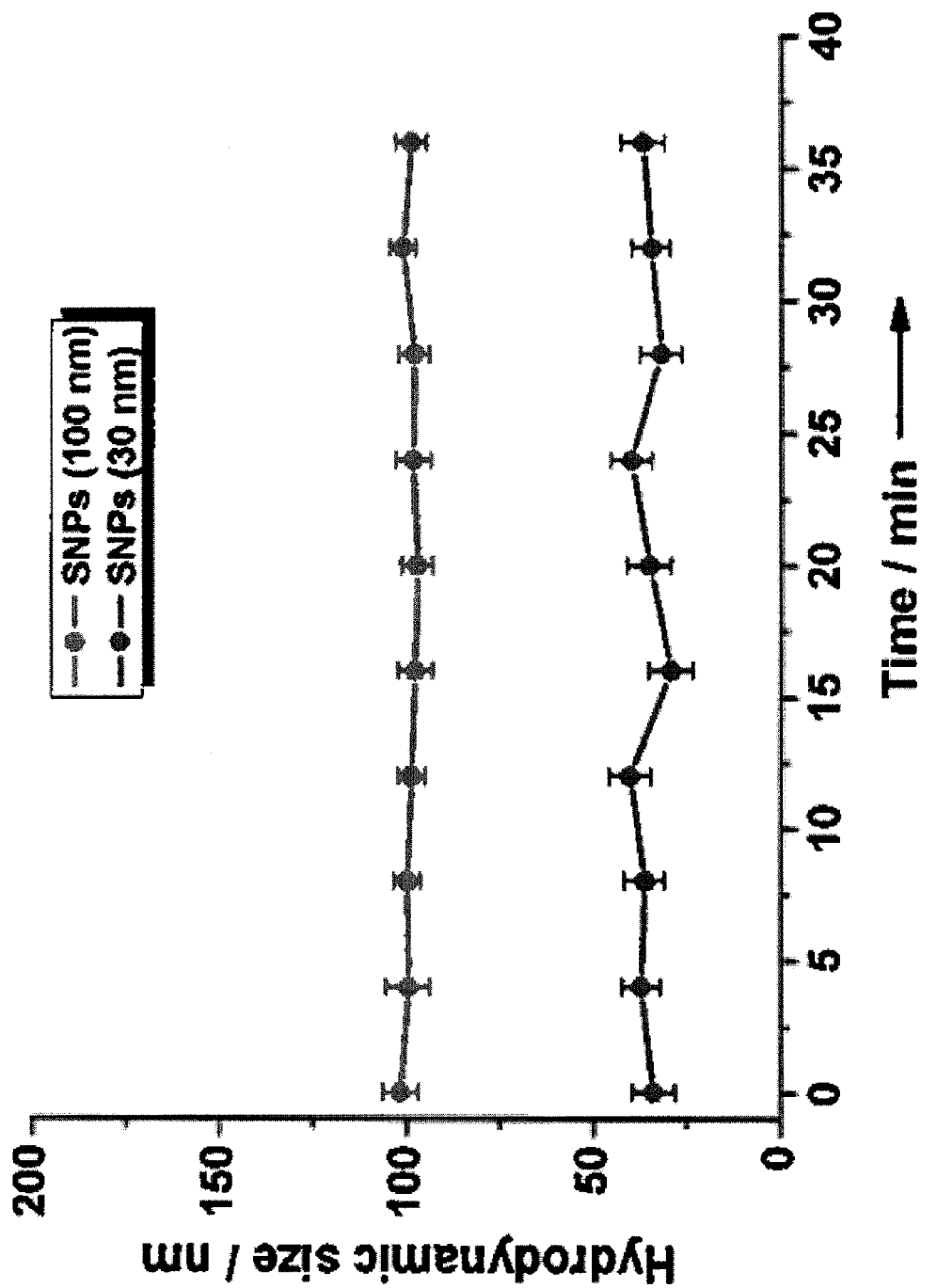
FIG. 4 shows time-dependent size variation of the 30 and 100-nm SNPs in PBS (pH 7.2) under a physiological ionic strength (I=150 mM).
Figure 5:
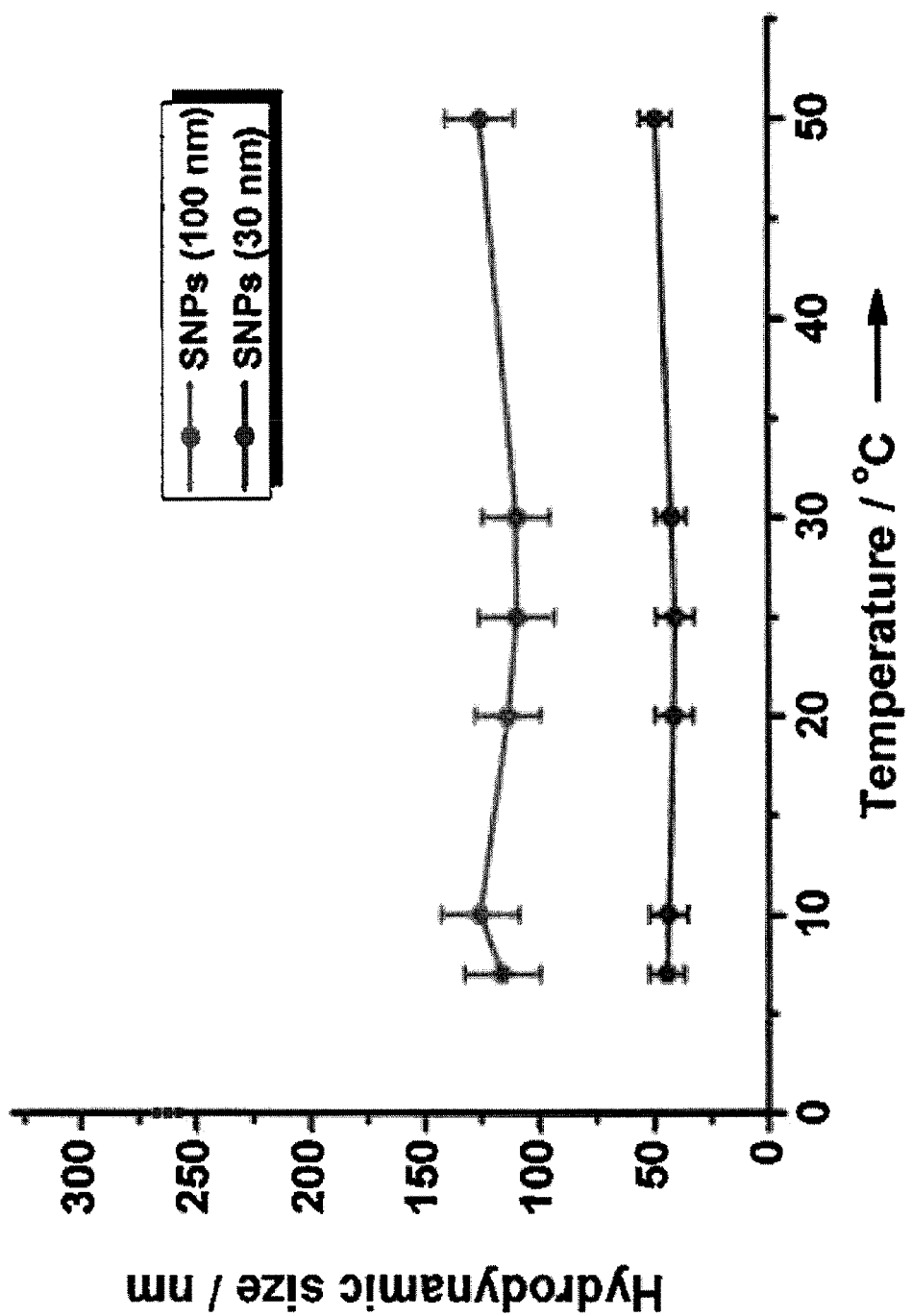
FIG. 5 shows the temperature-dependent size variation of both of the 30 and 100-nm SNPs in PBS buffer (pH=7.2, I=150 mM NaCl) with temperature increase from 7 to 50° C.
Figure 6:
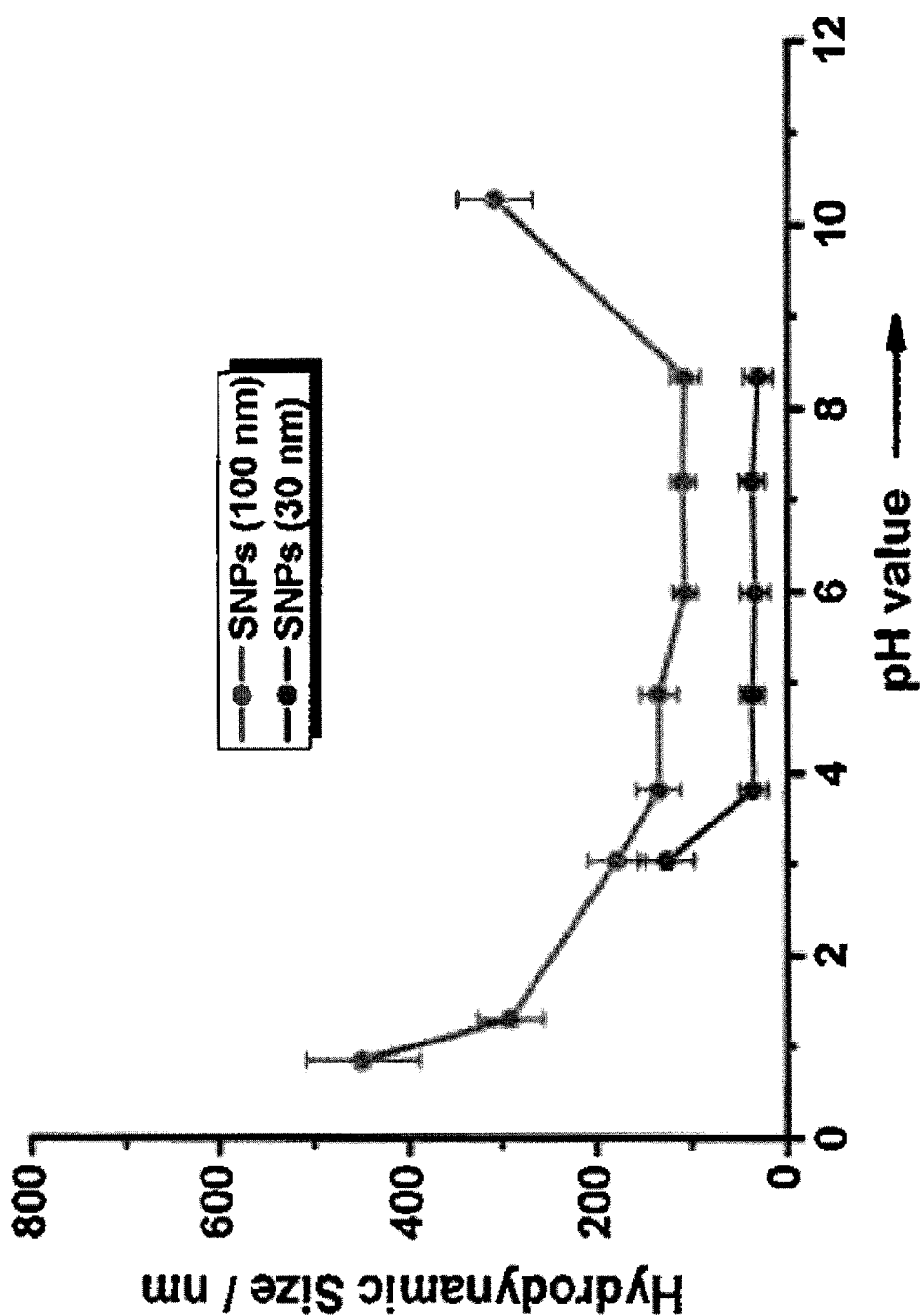
FIG. 6 shows pH-dependent size variation of both 30 and 100-nm SNPs in the respective buffer solutions with pH values ranging from 0.84 to 10.28 (I=100 mM).
Figure 7:
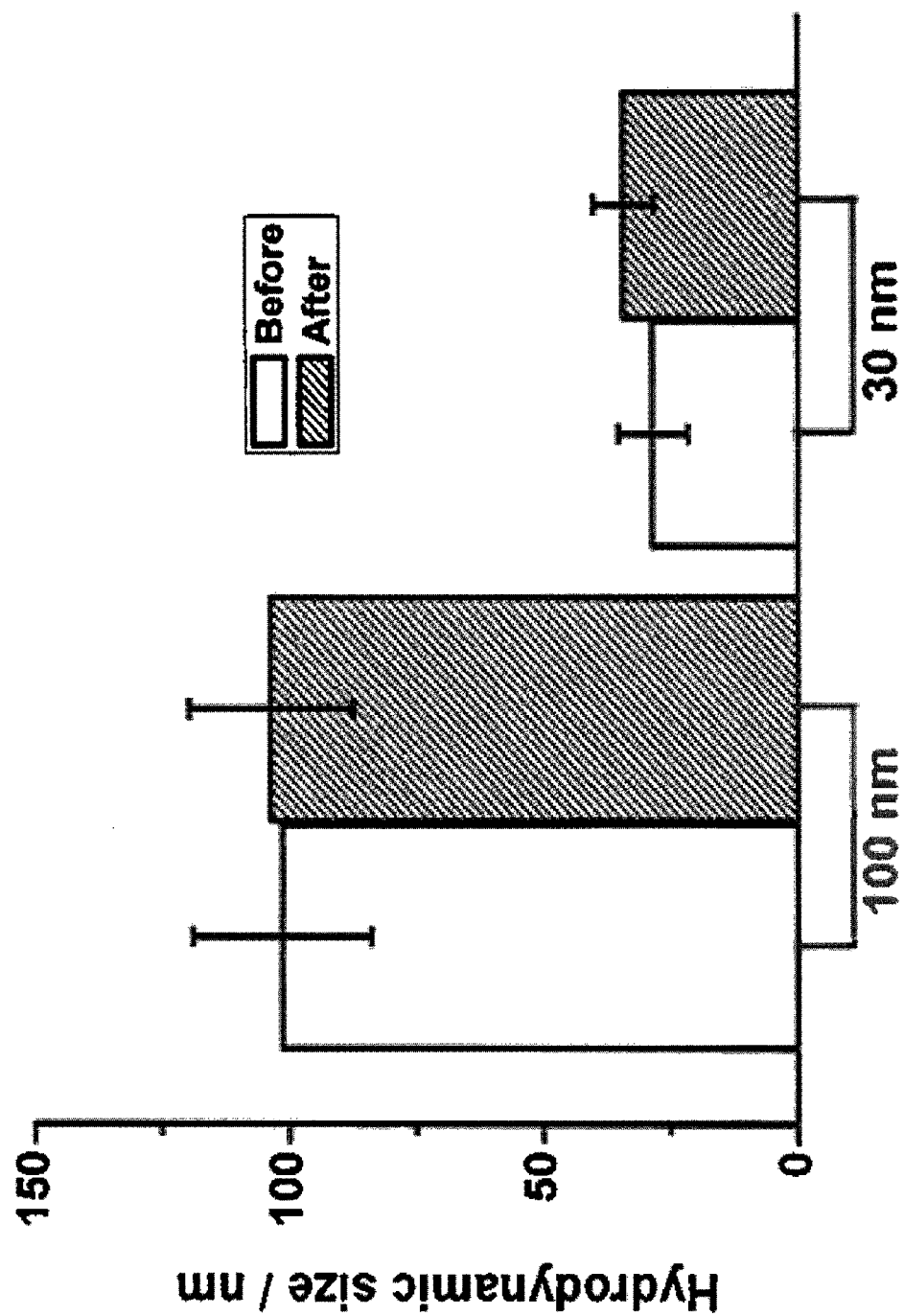
FIG. 7 shows the Sonication effect on size variation of 30 and 100-nm SNPs.
Figure 8:
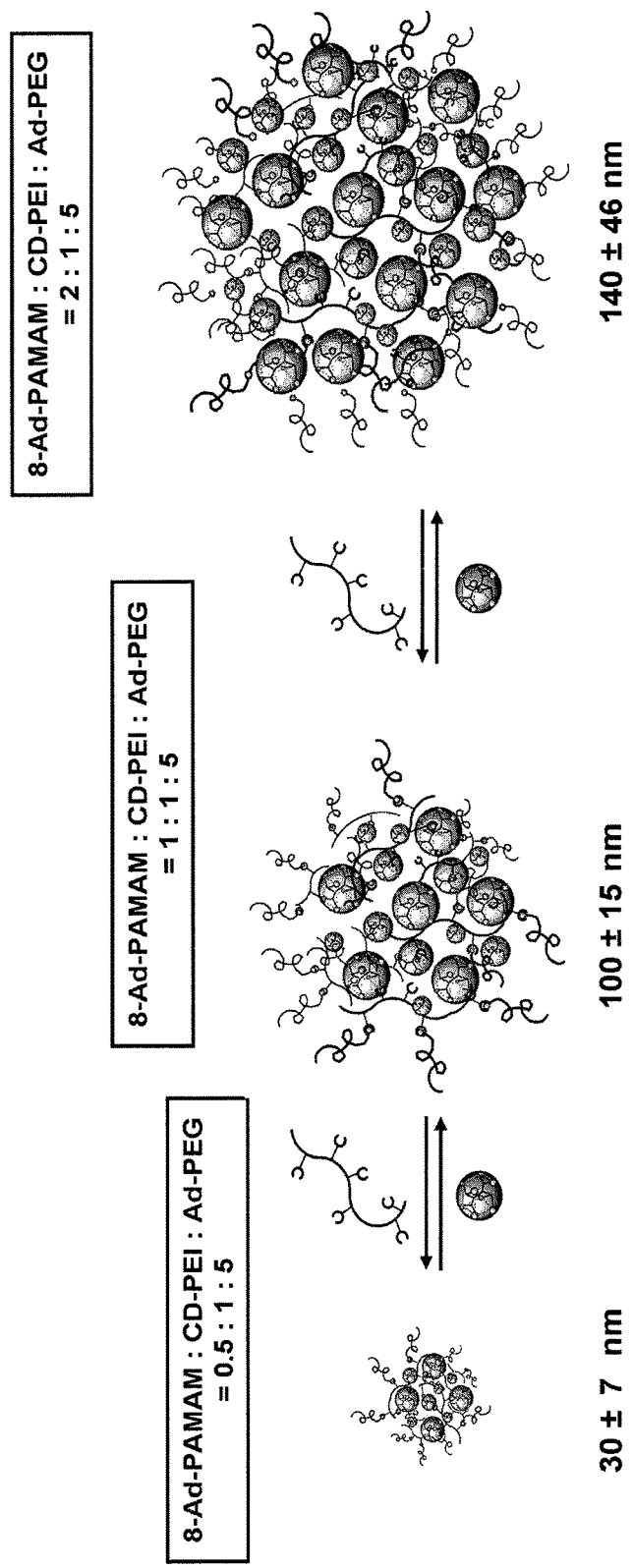
FIG. 8 shows a schematic representation illustrating the reversible size controllability of SNPs.

The use of supramolecular approach confers dynamic characteristics to the self-assembled SNPs. To understand the dynamic stability of the SNPs, real-time DLS measurements were used to monitor the size variation of the 30-nm and 100-nm SNPs (composed of 8-Ad-PAMAM-based dendrimer) at different temperatures, pH values, as well as in physiological ionic strength media. First, the variable-temperature DLS measurements indicate that the SNPs are stable at wide range of temperatures (7 to 50° C.) (FIG. 5). Second, negligible size variation of the SNPs was observed against the changes of pH values (from pH 3.8 to 8.3) and physiological ionic strength (FIGS. 4 and 6). The stability of these SNPs may be attributed to the multivalent CD/Ad recognition, which holds individual molecular building blocks into each SNP. Two sets of experiments were carried out to examine the dynamic characteristics (i.e., competitive disassembly and reversible size controllability) of these SNPs, which further validates the molecular mechanism of this supramolecular approach. First, 100 eq of a competitive reagent (i.e., 1-adamantamine hydrochloride) was introduced into a solution containing either 30-nm or 100-nm SNPs. After 10-min sonication, disassembly of SNPs was observed by DLS as a result of competition inclusion of the free 1-adamantamine hydrochloride into CD-PEI. As a control, without the addition of 1-adamantamine hydrochloride, sonication alone could not disassemble the SNPs (FIG. 7). Second, starting from 100-nm SNPs (8-Ad-PAMAM/CD-PEI=1:1, mol/mol), the size of the SNPs was reduced to 30 nm by adding the polymer component CD-PEI in situ (8-Ad-PAMAM/CD-PEI=1:2, mol/mol), or increase the size of SNPs to 140 nm by adding the dendrimer component 8-Ad-PAMAM in situ (8-Ad-PAMAM/CD-PEI=2:1, mol/mol) (FIG. 8). In these studies, 10-min sonication was employed to facilitate the conversion among the three sizes of SNPs.

Stability of SNPs Under a Physiological Ionic Strength (I=150 mM NaCl)

To ensure the in vivo stability of the SNP, the size variation of under a physiological ionic strength was examined (I=150 mM NaCl). 30-nm and 100-nm SNPs were prepared in PBS solutions (pH=7.2) under an ionic strength (I) of 150 mM NaCl. After mixing the three molecular building blocks in respective ratios, real-time DLS measurements were employed to monitor the size variation of both of the 30-nm and 100-nm SNPs at different times. The SNP sizes were recorded every 4 min for 36 min. The results (FIG. 4) indicate that the SNPs exhibit good stability in solution under a physiological ionic strength.

Stability of SNPs Under Different Temperatures

To understand the thermal stability of the SNPs, real-time DLS measurements were employed to monitor the size variation of both of the 30-nm and 100-nm SNPs in PBS (pH=7.2, I=150 mM NaCl) at different temperatures ranging from 7 to 50° C. In each case, the samples were equilibrated under a given temperature for 20 min prior to data acquisitions. The results (FIG. 5) indicated that the SNPs exhibit good thermal stability at the temperature range of 7 to 50° C., allowing the use of the SNPs in living organisms with temperate 36-38° C.

Stability of SNPs in Different pH Values

Information on the stability of SNPs in variable pH environments is needed to understand its characteristics under physiological conditions and to provide a reasonable pH range for chemical modification of SNPs for further experiments. The pH-dependent stability of SNPs was tested at pH range from 0.84 to 10.28 by DLS analysis. The original SNPs stock solution in PBS buffer was diluted to a proper concentration with buffer solutions with different pH values for DLS detection. The following buffers were used to adjust the pH values of the samples: 100 mM HCl—KCl buffer (pH 0-2.0), 100 mM Glycine-HCl buffer (pH 2.2-3.6), 100 mM $CH_3COOH$—$CH_3COONa$ buffer (pH 3.7-5.6), 100 mM $Na_2HPO_4$—$NaH_2PO_4$ buffer (pH 5.8-8.0), 100 mM Tris-HCl buffer (pH 70-9.0) and 100 mM $Na_2CO_3$—$NaHCO_3$ buffer (pH 9.2-10.8). The final pH values were determined by pH meter. As can be seen from FIG. 6, SNPs showed excellent stability in a wide pH range from 3.8 to 8.3, indicating that the SNPs are stable enough for the biological environment. Under lower (pH<3.8) and higher (pH>8.3) value, SNPs with 100-nm size swelled up to more than 400 nm. Meanwhile, the SNPs with 30-nm sizes were completely disassembled and no significant scatter light signals could be detected by.

Sonication Stability

To examine the dynamic characteristics (i.e., competitive disassembly and reversible size controllability) of the SNPs, which further validate the molecular mechanism of this supramolecular approach, sonication was applied to provide the energy for overcoming the energy barrier required for reorganization of the SNPs. In order to understand how sonication affects the size variation of SNPs, The sizes of 30 and 100-nm SNPs in PBS (pH 7.2, I=150 mM) buffer solution were monitored by DLS before and after the respective SNPs were sonicated for 10 min at rt. No significant size variation was observed under the experimental condition (FIG. 7), suggesting that only sonication itself can not disassemble the SNPs.

In Vivo Biodistribution

Figure 10:
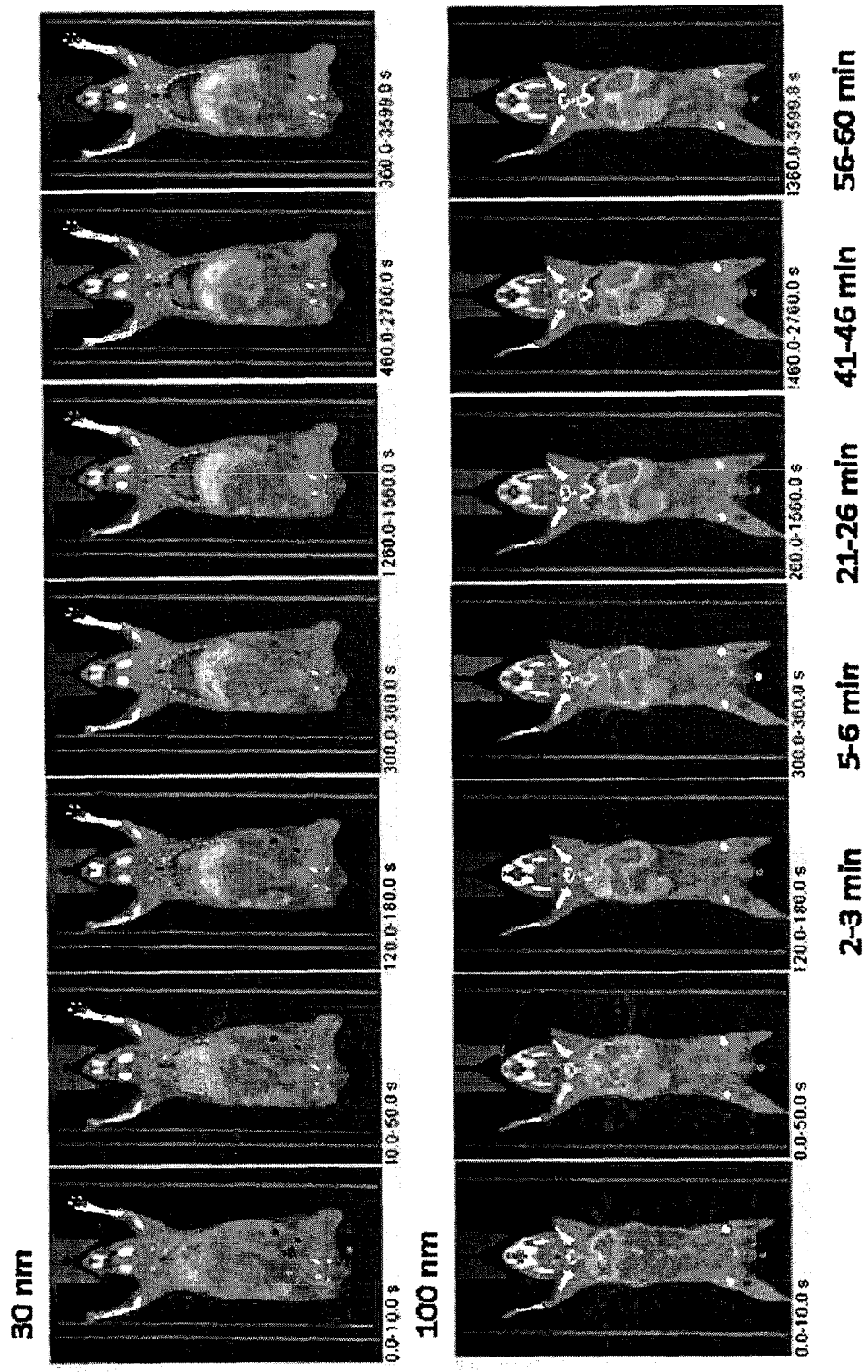
FIG. 10 shows time-resolved microPET/CT images from a 1 h dynamic scan. The top panel shows the images from a mouse that received the 30-nm DOTA-grafted SNPs via tail vein injection. The lower panel shows the images from a mouse that received the 100-nm DOTA-grafted SNPs also via tail vein injection
Figure 11:
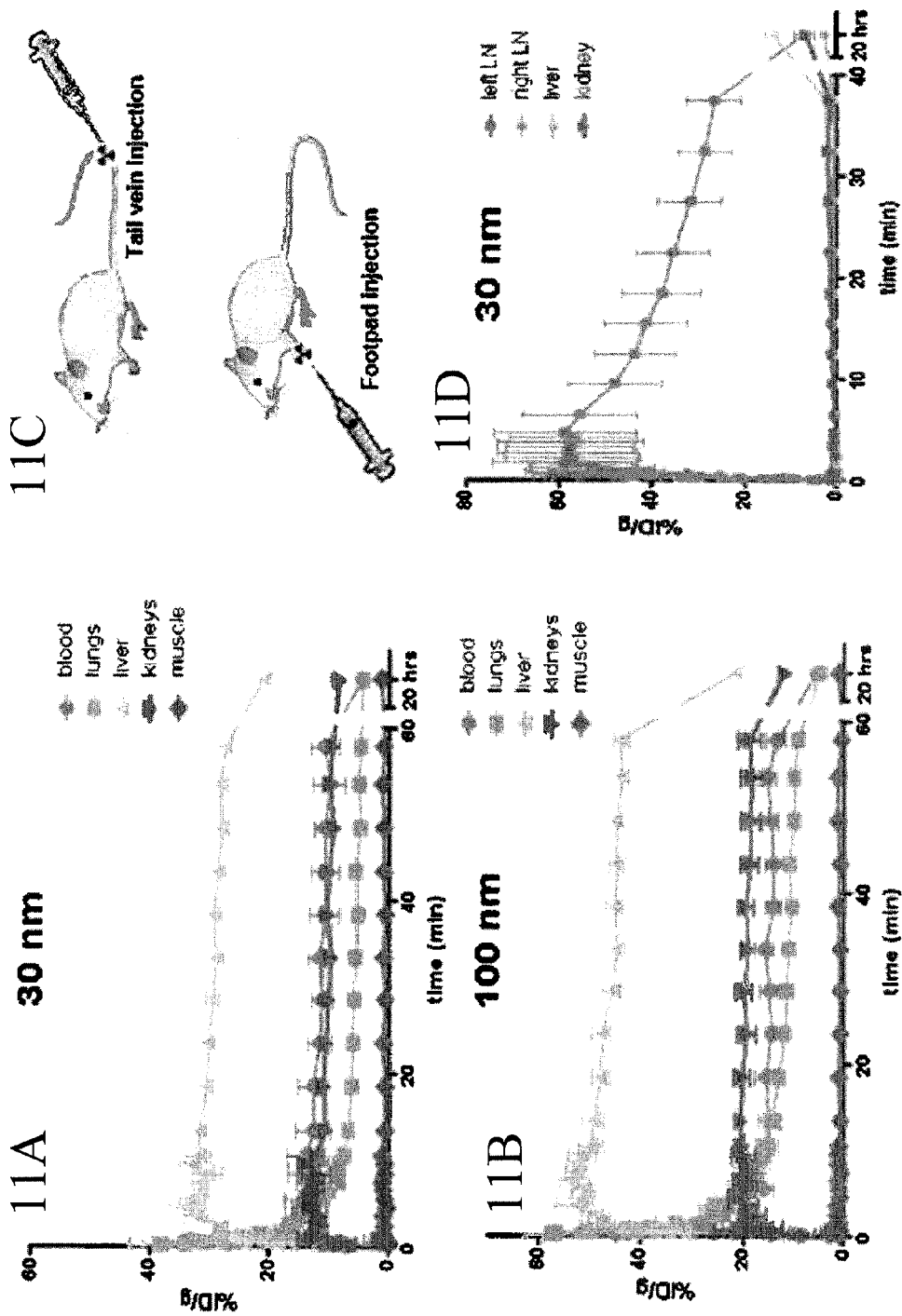
FIG. 11 shows the biodistribution of 30- and 100-nm SNPs following tail and footpad injections.

The in vivo biodistribution (FIG. 9A and FIG. 10) of both of the 30-nm and 100-nm $^{64}Cu$-labeled SNPs (composed of 8-Ad-PAMAM-based dendrimer) were measured by systemically injecting the SNPs into mice via the tail veins (FIG. 11C). MicroPET/CT studies suggested that the biodistribution patterns of the 30-nm and 100-nm SNPs were quite similar (FIGS. 11A and 11B). In both cases, rapid blood clearance through liver accumulation (30-50% ID/g of the SNPs accumulated in the liver within 5 min after injection) was observed, and there was less accumulation in the kidneys (16-20% ID/g) and lungs (8-12% ID/g). A nonlinear two-phase decay fit of the SNPs plasma concentrations yielded initial elimination half-lives of 0.87 min and 1.1 min for the 30-nm and 100-nm SNPs, respectively. The terminal elimination half-lives were also quite different (30-nm SNPs was 68 min, and 100-nm SNPs was 108 min). Together, the results indicated that the in vivo clearance of the 30-nm SNPs is faster than that of the 100-nm SNPs.

Lymph Node Trafficking

Figure 9:
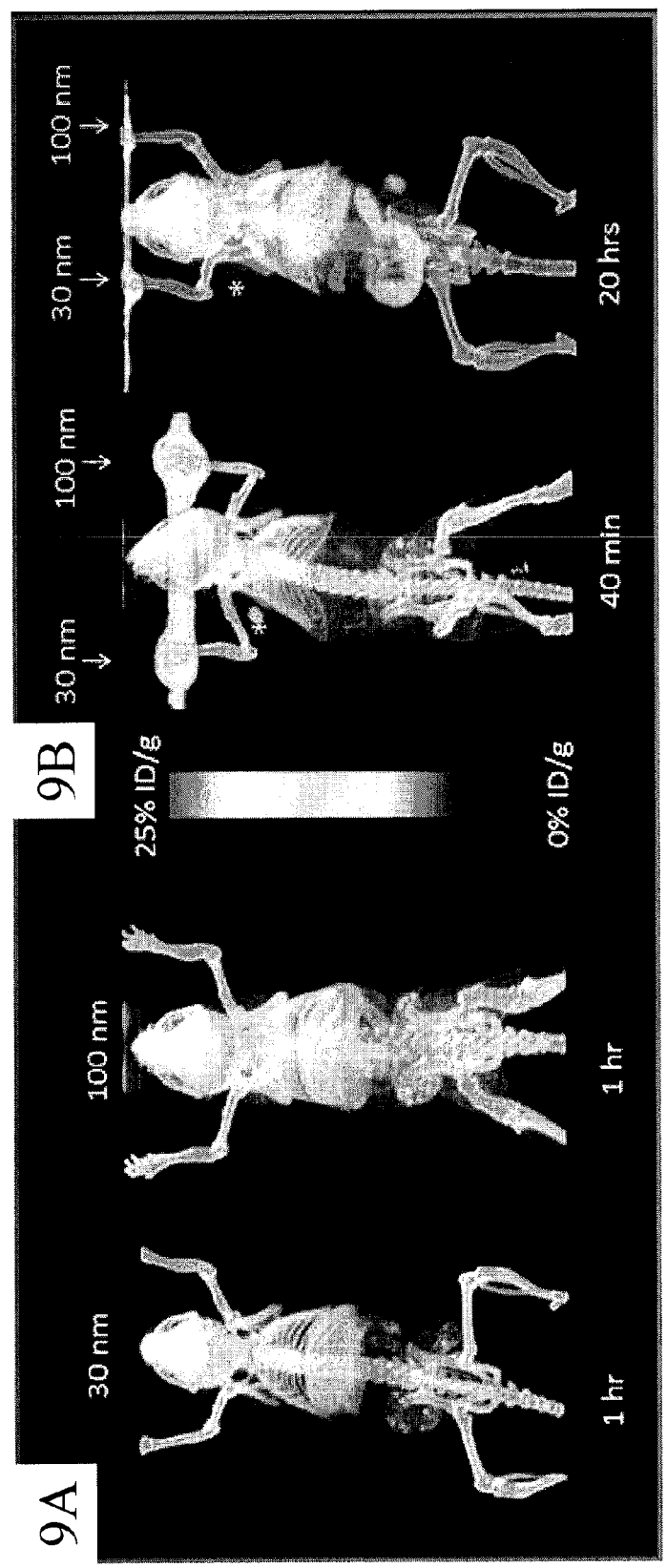
FIG. 9 shows MicroPET/CT studies of both 30-nm and 100-nm $^{64}$Cu-labeled SNPs at various time points after injections into mice.

To explore the use of the SNPs for immune modulation, lymph node trafficking of both 30-nm and 100-nm $^{64}$Cu-labeled SNPs via front footpad injection (FIG. 11C) was investigated. The path of lymph drainage from footpad injections is well known, and hence this is a common method for delivery of immunological agents (Peek et al., *Adv. Drug Deliv. Rev.*, vol. 60, p. 915, 2008). The 30-nm and the 100-nm SNPs were injected on different sides of footpads of a mouse, and microPET/CT imaging was carried out for 40 min (FIG. 9B, left panel) immediately after injection and at 20 h post injection (FIG. 9B, right panel). The 30-nm SNPs drained to the local auxiliary lymph node and peaked at 5 min post injection with 58.6±15.6% ID/g of signal accumulation (FIG. 11D). This signal decreased to 26.6±5.8% ID/g at 40 min post injection, and further reduced to 7.0±2.2% ID/g by 20 h post injection. No significant accumulation was detected in the lymph nodes on the same side that the 100-nm SNPs were injected. Other than the footpad injection site and the lymph node in which the 30-nm SNPs were drained, the SNPs did not distribute to other regions in vivo by 1 h after injection. The results revealed that the sizes of SNPs are critical factors for their lymph node trafficking.

Preparation of $^{64}$Cu-Labeled SNPs

For the purpose of PET imaging studies, both the 30-nm and 100-nm $^{64}$Cu-labeled SNPs were prepared. 30 and 100-nm DOTA-grafted SNPs can be prepared by self assembly of three different molecular building blocks—namely (i) 8-Ad-PAMAM, (ii) CD-PEI-DOTA and (iii) Ad-PEG.

Figure 38:
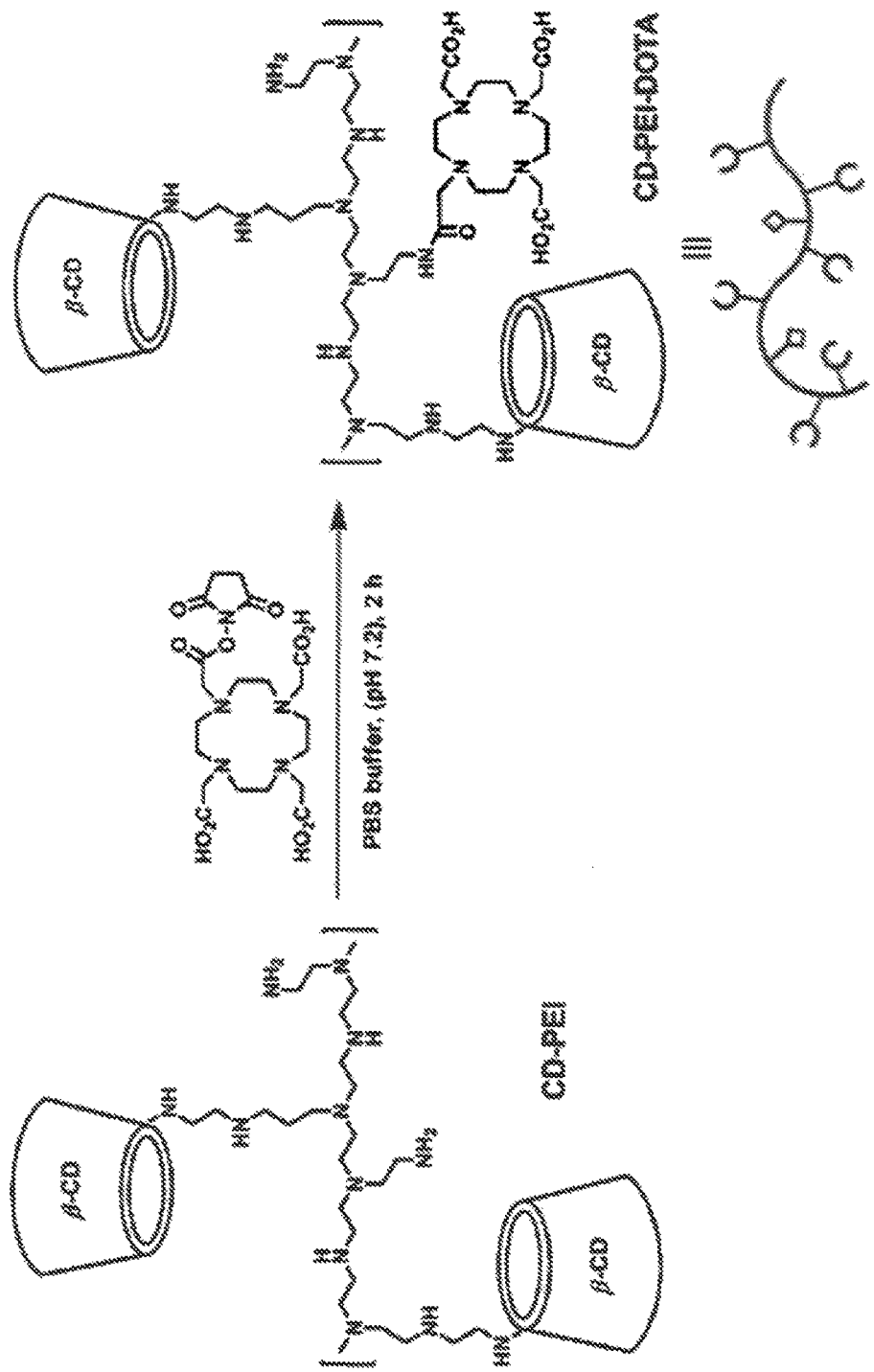
FIG. 38 shows the synthesis of CD-PEI-DOTA from CD-PEI and DOTA-NHS.

Synthesis of CD-PEI-DOTA (FIG. 38)

To a solution of CD-PEI (1.7 mg, 0.1 µmol, 1 equiv.) in PBS buffer solution (pH 7.2), DOTA-NHS (0.5 mg, 1 µmol, 10 equiv.) was added, and the reaction mixture was stirred at rt for 2 h. After the reaction completed, the mixture was purified by dialysis (Slide-A-Lyzer® dialysis cassette, MWCO 10 kD) against DI water overnight and lyophilized to yield CD-PEI-DOTA.

Figure 39:
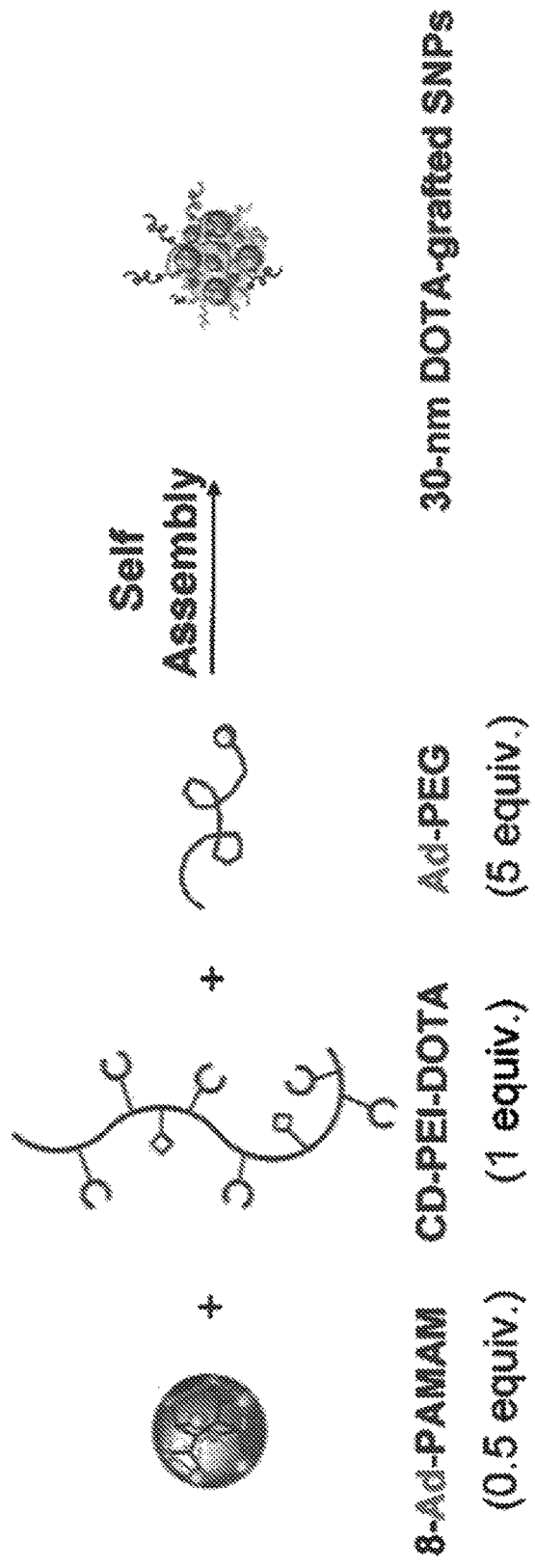
FIG. 39 shows the preparation of 30-nm DOTA-grafted SNPs from 8-Ad-PAMAM, CD-PEI-DOTA, and Ad-PEG.

Preparation of 30-nm DOTA-Grafted SNPs (FIG. 39)

To a solution of Ad-PEG (6.3 mg, 1.26 µmol, 5 equiv.) in 750 µL DI water, 8-Ad-PAMAM (0.39 mg, 0.12 µmol, 0.5 equiv.) in 15-µL DMSO was slowly injected via a Hamilton under vigorous stirring. 750-4 of DI water containing CD-PEI-DOTA (4.3 mg, ~0.25 µmol, 1 equiv.) was sequentially added into the mixture to obtain 30-nm DOTA-grafted SNPs.

Figure 40:
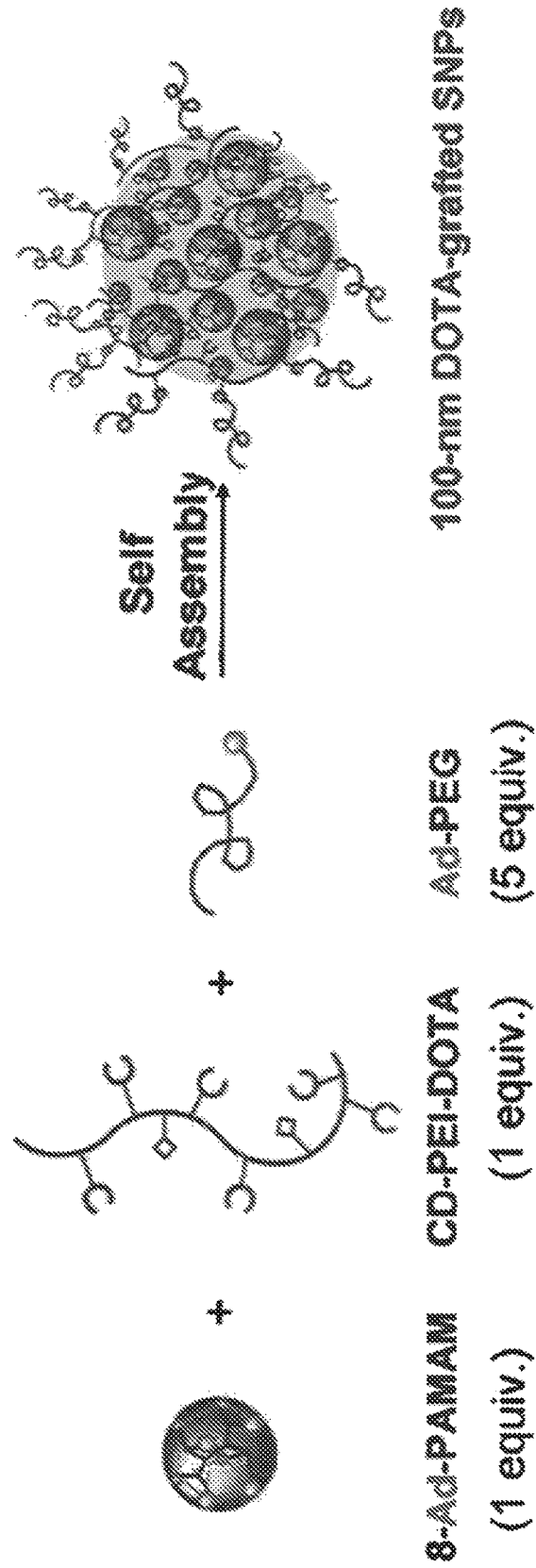
FIG. 40 shows the preparation of 100-nm DOTA-grafted SNPs from 8-Ad-PAMAM, CD-PEI-DOTA, and Ad-PEG.

Preparation of 100-nm DOTA-Grafted SNPs (FIG. 40)

In a similar manner to prepare 30-nm DOTA-grafted SNPs, Ad-PEG (6.3 mg, 1.26 µmol, 5 equiv.), 8-Ad-PAMAM (0.78 mg, 0.25 µmol, 1 equiv.), and CD-PEI-DOTA (4.3 mg, ~0.25 µmol, 1 equiv.) were mixed to prepare 100-nm DOTA-grafted SNPs.

Figure 41:
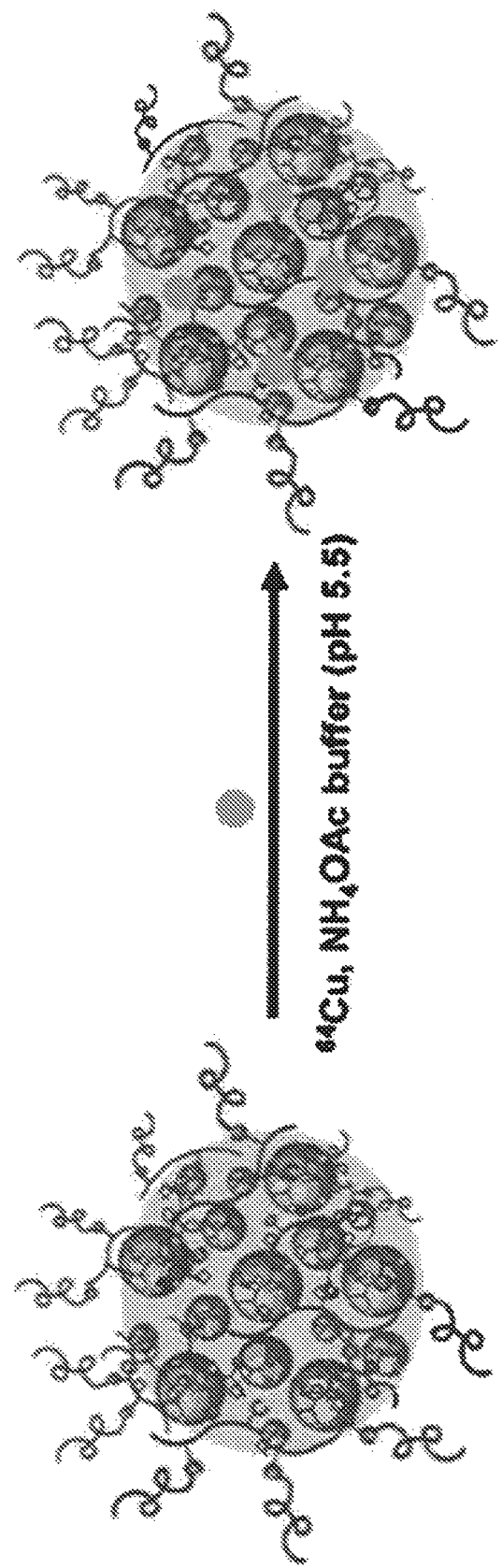
FIG. 41 shows the preparation of $^{64}$Cu labeling of DOTA-grafted SNPs.

$^{64}$Cu Labeling of DOTA-Grafted SNPs (FIG. 41)

All liquids were pretreated with Chelex-100 (Bio-Rad, Herchules, Calif.) to remove trace metal contaminants. The $^{64}$Cu chloride (MDS Nordion, Vancouver, Canada) was mixed with NH$_4$OAc buffer (pH 5.5, I=0.1 M), and 800-fold excess of nanoparticles were added to above solution. The mixture was incubated for 1 h at 60° C., and the $^{64}$Cu-labeled SNPs product was purified by a molecular weight cut off filter (Centricon YM10, Billerica, Mass.) with a spin speed of 10000 g for 10 min. The labeling yield (>90%) was determined by measuring the radioactivity in the filter, the filtrate and the retaintate, respectively. The $^{64}$Cu-labeled SNPs are then re-suspended in PBS for in vivo injections.

Micro-PET/CT Imaging

C57BL/6 mice were purchased from Jackson Laboratory (Bar Harbor, Me.). All animal manipulations were performed with sterile technique and were approved by the University of California at Los Angeles Animal Research Committee. Micro-PET/CT imaging was performed with a micro-PET FOCUS 220 PET scanner (Siemens, Malvern, Pa.) and a MicroCAT 11 CT scanner (Siemens). Fifteen minutes before imaging, mice were anesthetized by using 1.5-2% isoflurane in a heated (30° C.) induction chamber, then transferred to a heated isolation/imaging chamber. $^{64}$Cu (100-300 µCi) was injected either via tail vein or in the footpad while the anesthetized animals were positioned on the scanner bed, and a dynamic PET scan was acquired for 1 h (FIG. 10). The volume used for the tail vein injection were ~100 µL, and for the footpad injection <20 µL. Mice were moved to the micro-CT in the same isolation/imaging chamber. PET images were reconstructed by filtered back projection, using a ramp filter to yield an image resolution of 1.7 mm. Immediately after the micro-PET scan, mice underwent a 7-min micro-CT scan, using routine image acquisition parameters. The micro-CT scan was used for anatomical localization of the tissue concentrations of the $^{64}$Cu over time by micro-PET. Static micro-PET scans were acquired on the following day (18-24 h after injection) with another micro-CT scan for anatomical co-registration.

To determine temporal changes of tracer concentration in various tissues, ellipsoid regions of interest were placed in the region that exhibited the highest $^{64}$Cu activity as determined by visual inspection. To ensure accurate anatomical positioning, regions of interest were placed on fused micro-PET/CT images generated by the AMIDE software. To minimize partial volume effects, care was taken not to include the anatomical borders of the organs. Considering the size of the studied organs and tumors and the spatial resolution of the PET scanner, partial volume effects are not expected to have a major impact on the results of quantitative analysis. Activity concentrations are expressed as percent of the decay-corrected injected activity per cm$^3$ of tissue (can be approximated as percentage ID/g), using the AMIDE software, and these values are normalized to an elliptic cylinder region of interest drawn over the entire mouse.

Discussion

Herein, a convenient, flexible and modular synthetic approach (FIG. 1) for preparation of size-controllable supramolecular nanoparticles (SNPs) is described. The CD/Ad recognition was employed to achieve self assembly of SNPs from three different molecular building blocks—namely (i) Ad-grafted 1$^{st}$-generation polyamidoamine dendrimer, n-Ad-PAMAM, (ii) β-CD-grafted branched polyethylenimine (MW=10 kD), CD-PEI, and (iii) Ad-functionalized PEG compound (MW=5 kD), Ad-PEG. Similar to a previously reported "bricks and mortar" strategy (Boal et al., Nature, vol. 404, p. 746, 2000) to construct cross-linked network (Belloc et al., *Bioconjugate Chem.*, vol. 15, p. 1201, 2004). The use of a capping/solvation group, Ad-PEG, which, on one hand, competes with the dendrimer block, n-Ad-PAMAM to constrain the continuous propagation of the cross-linked network, and on the other hand, confers water-solubility to the SNPs. By tuning mixing ratios among the three molecular building blocks in PBS aqueous solution (pH=7.2, containing 1.5 mM $KH_2PO_4$, 155 mM NaCl and 2.7 mM $Na_2HPO_4$), the equilibrium between the propagation/aggregation and capping/solvation of the cross-linked network fragments can be altered, allowing arbitrary control of the sizes of the water-soluble SNPs. In contrast to the production of polymer-based nanoparticles (Sun et al., *Adv. Mater.*, vol. 19, p. 3157, 2007; Ferreira et al., *Cell Stem Cell*, vol. 3, p. 136, 2008; Bertin et al., *J. Am. Chem. Soc.*, vol. 128, p. 4168, 2006), where significant synthetic endeavors were required to prepare specific types of polymeric building blocks in order to achieve desired size controllability, the three-component supramolecular approach offers synthetic convenience, flexibility and modularity to alter sizes and surface chemistry of the SNPs. Based on such a supramolecular approach, a collection of SNPs with controllable sizes ranging from 30 to 450 nm was obtained. Further studies were carried out to unveil unique properties of these SNPs, including (i) their stability at different temperatures and pH values, as well as in physiological ionic strength media, (ii) the competitive disassembly in the presence of Ad molecules, and (iii) the reversible size controllability via in situ alteration of mixing ratios of the molecular building blocks. Finally, whole-body biodistribution and lymph node drainage studies of both of the 30- and 100-nm $^{64}$Cu-labeled SNPs in mice were carried out using microPET/CT imaging. The results revealed that the sizes of SNPs are crucial factors, which affect the respective in vivo properties of the SNPs.

Figure 3:
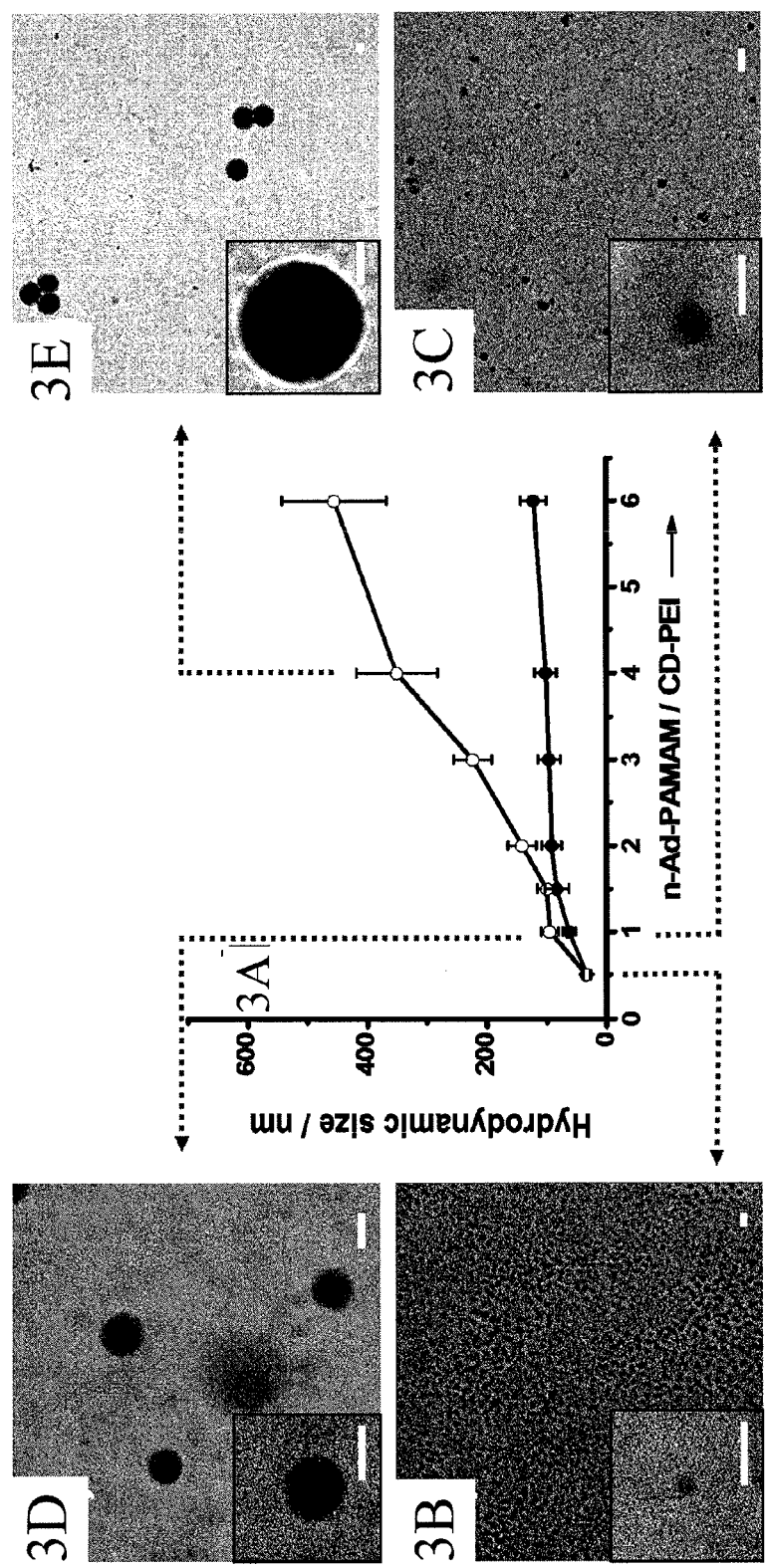
FIG. 3 shows the relationship between SNP size and mixing ratios. 3A shows titration plots summarize the relationship between SNP sizes and mixing ratios of the two molecular building blocks (n-Ad-PAMAM/CD-PEI). Dynamic light scattering (DLS) was employed to measure SNP sizes. Hollow circles: the titration plot observed for an octa-substituted dendrimer building block 8-Ad-PAMAM; Solid circles: the titration plot observed for a tetra-substituted dendrimer building block 4*-Ad-PAMAM. The standard deviation of each data point was contained from, at least, three repeats. TEM images of the resulting SNPs with different sizes of 32±7 nm (3B) from 8-Ad-PAMAM, 61±17 nm (3C) from 4*-Ad-PAMAM, 104±16 nm (3D) from 8-Ad-PAMAM and 340±46 nm (3E) from 8-Ad-PAMAM. Scale bars: 100 nm.

In the polymer building block CD-PEI, there are ca. 7 to 8 CD binding regions or recognition units grafted on a branched PEI backbone according to its $^1$H NMR spectrum. The CD modification may increase bio compatibility and reduce toxicity of the PEI compounds (Davis et al., *Nat. Rev. Drug Discov.*, vol. 3, p. 1023, 2004). In these experiments, two different dendrimer building blocks, i.e., 8-Ad-PAMAM with eight substituted Ad motifs and 4*-Ad-PAMAM (According to MS analysis, 4*-Ad-PAMAM is composed of six different Ad-substituted PAMAMs, including 2-Ad-PAMAM, 3-Ad-PAMAM, 4-Ad-PAMAM, 5-Ad-PAMAM, 6-Ad-PAMAM and 7-Ad-PAMAM) with four Ad motifs (in average, based on its $^1$H NMR spectrum), were tested in parallel. To examine how the mixing ratios between Ad-PAMAM and CD-PEI affect the sizes of the resulting SNPs, dynamic light scattering (DLS, N4 plus, USA) measurements were utilized to analyze the freshly prepared SNPs. To ensure sufficient supply of the capping/solvation group, an excess amount of Ad-PEG were added in to each mixture. In the absence of Ad-PEG, direct mixing of n-Ad-PAMAM and CD-PEI resulted in aggregation and precipitation. The octa-substituted dendrimer 8-Ad-PAMAM was first tested. In this case, CD-PEI (168 µM) in PBS buffer was slowly added into the mixtures containing Ad-PEG (840 µM) and variable amount (84 to 672 µM) of 8-Ad-PAMAM. As shown in FIG. 3A, collection of water-soluble SNPs with variable sizes ranging between 30 and 450 nm was obtained. Meanwhile, the surface charge densities of SNPs (with diameters range from 30 to 450 nm) were determined by zeta potential ($\zeta$) measurements in PBS buffer solution (Zetasizer Nano, Malvern Instruments Ltd), suggesting that the SNPs carry zeta potentials in a range of 16.8±1.2 to 28.5±1.1 mV (FIG. 2). To test how the number of the Ad-substitution groups in a dendrimer core affects the sizes of the respective SNPs, the tetra-substituted dendrimer 4*-Ad-PAMAM was also examined. SNPs with relative smaller sizes (30-120 nm) were obtained under similar self-assembly conditions.

Example 2—Gene Delivery by Supramolecular Nanoparticles (SNP)

General

Reagents and solvents were purchased from Sigma-Aldrich (St. Louis, Mo.) and used as received without further purification otherwise noted. Branched polyethylenimine (PEI, MW=10 kD) was purchased from Polysciences Inc. (Washington, Pa.). Polymers contain primary, secondary and tertiary amine groups in approximately 25/50/25 ratio. $1^{st}$-generation polyamidoamine dendrimer (PAMAM) with 1,4-diaminobutane core and amine terminals in 20% wt. methanol solution was purchased from Dendritic Nanotechnologies, Inc (Mount pleasant, MI). 1-Adamantanamine (Ad) hydrochloride and b-cyclodextrin (β-CD) were purchased from TCI America (San Francisco, Calif.). N-hydroxysuccinimide (SCM) and maleimido (MAL) hetero-functionalized polyethylene glycol (SCM-PEG-MAL, MW=5 kD) was obtained from NANOCS Inc (New York, N.Y.). Phosphate-buffered saline (PBS, 1×, pH 7.2±0.05) for sample preparation, UltraPure™ 10×TBE buffer (including 1 M Tris, 0.9 M boric acid, and 0.01 M EDTA) for electrophoresis experiment and 1×TE buffer (including 10 mM Tris-HCl containing 1 mM EDTA) for DNA dilution were purchased from Invitrogen (Carlsbad, Calif.). 6-Monotosyl-β-cyclodextrin (6-OTs-β-CD) was prepared following the literature reported method (Petter et al., *J. Am. Chem. Soc.*, vol. 112, pp. 3860-3868, 1990). Octa-Ad-grafted polyamidoamine dendrimer (Ad-PAMAM), CD-grafted branched polyethylenimine (CD-PEI) and Ad-grafted polyethylene glycol (Ad-PEG) were prepared as described above. Dry $CH_2Cl_2$ was obtained by refluxing over $CaH_2$ and freshly distilled before use. MCF7 breast cancer cell line, U87 brain cancer cell line and NIH 3T3 mouse fibroblast cell line were purchased from American Type Culture Collection. The Dulbecco's Modified Eagle Medium (DMEM), Earl's Modified Eagle's Medium (EMEM) growth medium, Opti-MEM reduced serum medium and Penicillin/streptomycin were obtained from Invitrogen (Carlsbad, Calif.). Fetal Bovine Serum (FBS) and EGFP-encoded plasmid DNA (pMAX EGFP®, 3.4 kb) were obtained from Lonza Walkerrsville Inc (Walkerrsville, Md.). 4',6-Diamidino-2-phenylindole (DAPI) was purchased from Invitrogen (Carlsbad, Calif.). Arginine-glycine-aspartic-cysteine (RGDC) peptide was purchased from GenScript Corp. (Piscataway, N.J.).

$^1$H NMR spectra were recorded on a Bruker Avance 400 spectrometer in deuterated solvents. Mass spectra were acquired using an Applied Biosystems Voyager DE-STR MALDI-TOF mass spectrometer (Framingham, Mass.). Dynamic light scattering and zeta potentials of SNPs-DNA and RGD-SNPs-DNA were measured on Zetasizer Nano instrument (Malvern Instruments Ltd., United Kingdom). Transmission electron microscope (TEM) images were measured on Philips CM 120 electron microscope operating with an acceleration voltage of 120 kV. Ethidium bromide (EtBr) exclusion assay was performed on a spectrofluorometer (FluoroMax-3, Spex). Cell imaging and gene transfection studies were performed on a Nikon TE2000S inverted fluorescent microscope with a CCD camera (Photomatrix, Cascade II), X-Cite 120 Mercury lamp, automatic stage, and filters for three fluorescent channels (W1 (DAPI), W2 (EGFP and AO) and W3 (PI)).

Electrophoresis Analysis

Figure 12:
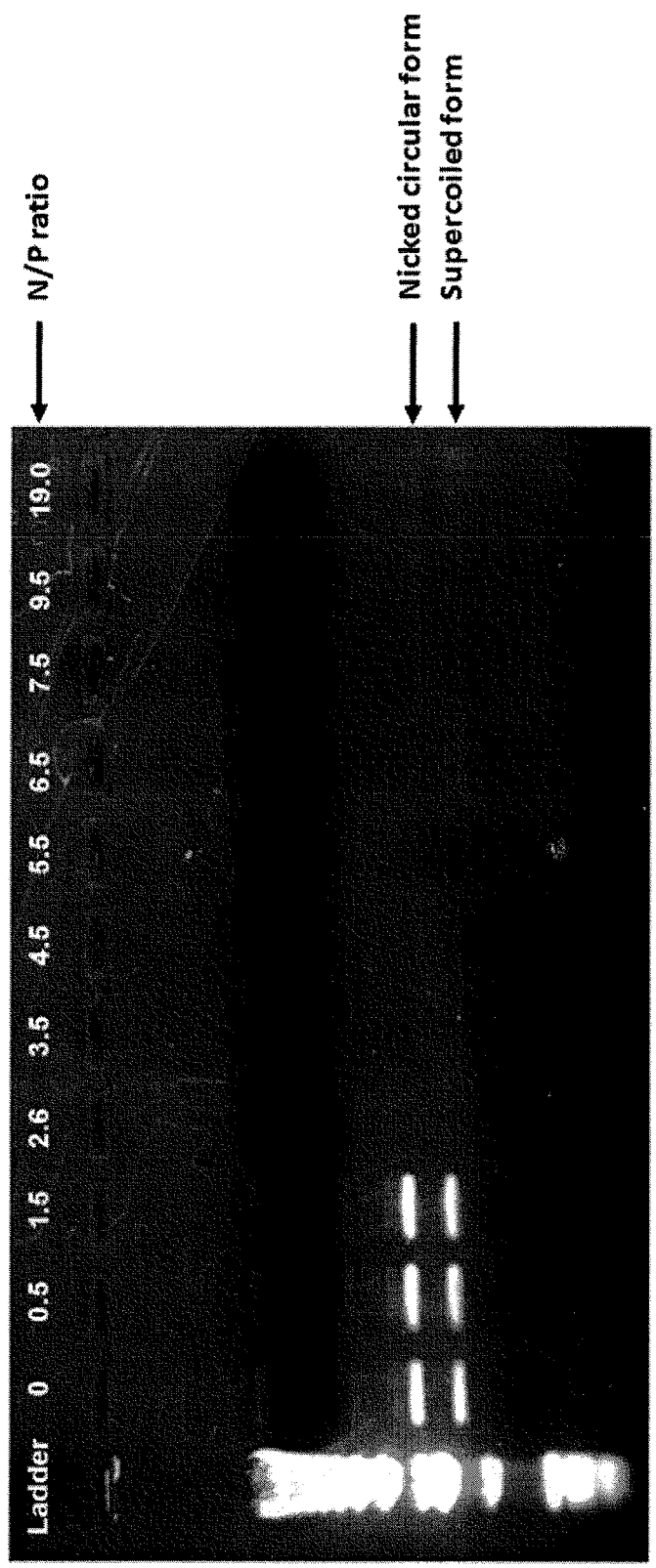
FIG. 12 shows gel electrophoresis of the cationic Ad-PAMAM/CD-PEI hydrogel with anionic DNA at various nitrogen-phosphate (N/P) ratios from 0 to 19 as indicated. The two bands of plasmid DNA observed by electrophoresis represent the nicked circular and supercoiled forms of plasmid, respectively.

The DNA loading capacity of the cationic Ad-PAMAM/CD-PEI hydrogel for the anionic DNA was determined by electrophoresis analysis using 1.0% agarose gel in 1×TBE buffer. Experiments were run at 80 V for 90 min. About 50 ng/μL of DNA was mixed with different amounts of the mixture of cationic Ad-PAMAM/CD-PEI hydrogel to achieve the desired N/P ratio. The resulting solutions were incubated for 1 h prior to running the experiment. DNA was visualized under UV illumination by staining the gels with ethidium bromide (0.5 μg/mL) at room temperature (FIG. 12).

Ethidium Bromide Exclusion Assay

Figure 13:
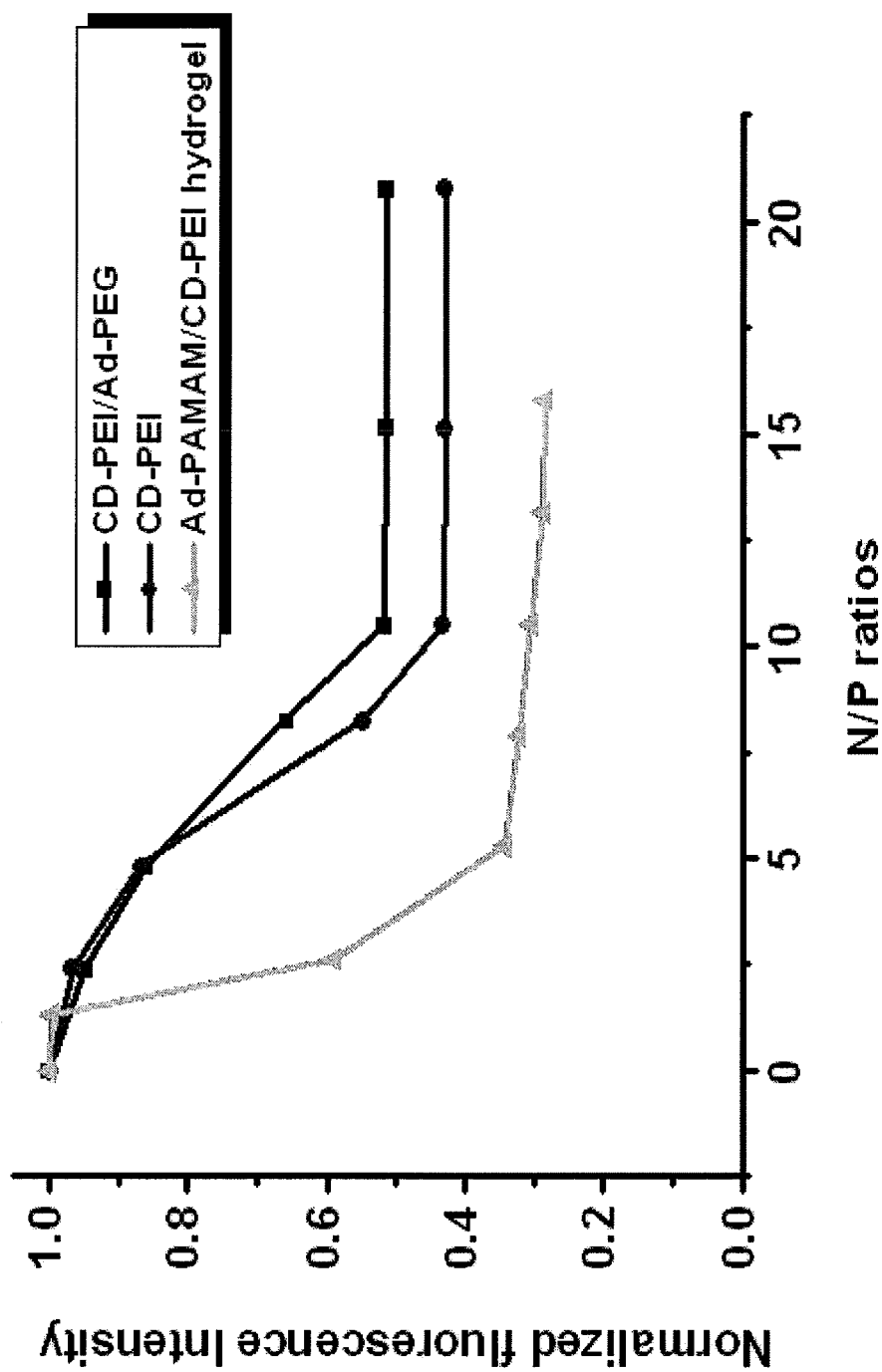
FIG. 13 shows the fluorescence intensity changes of DNA-EtBr, composed of EtBr (400 ng/mL) and DNA (20 µg/mL) in PBS solution (1 mL), were measured at 590 nm after adding various amounts of Ad-PAMAM/CD-PEI hydrogel along with other controls (CD-PEI and the mixture of CD-PEI/Ad-PEG).

The DNA loading capacity of cationic Ad-PAMAM/CD-PEI hydrogel for anionic DNA were further validated via ethidium bromide (EtBr) exclusion assay. A PBS solution (pH 7.2) containing the EtBr (400 ng/mL) and DNA (20 μg/mL) was incubated at room temperature for 10 min to form a stable complex (DNA-EtBr). After adding various amounts of cationic Ad-PAMAM/CD-PEI hydrogel along with other controls (CD-PEI and the mixture of CD-PEI/Ad-PEG), the fluorescence intensity changes of DNA-EtBr were measured using a spectrofluorometer (FluoroMax-3, Spex). The excitation and emission wavelengths were 510 and 590 nm, respectively. Slit width was 5 nm. The most significant fluorescence quenching of DNA-EtBr was observed in the presence of cationic Ad-PAMAM/CD-PEI hydrogel. This result indicated that cationic Ad-PAMAM/CD-PEI hydrogel can condense the anionic plasmid DNA more efficiently than CD-PEI or the mixture of CD-PEI/Ad-PEG (FIG. 13).

Preparation of DNA-Encapsulated SNPs-DNA and RGD-SNPs-DNA

Figure 42:
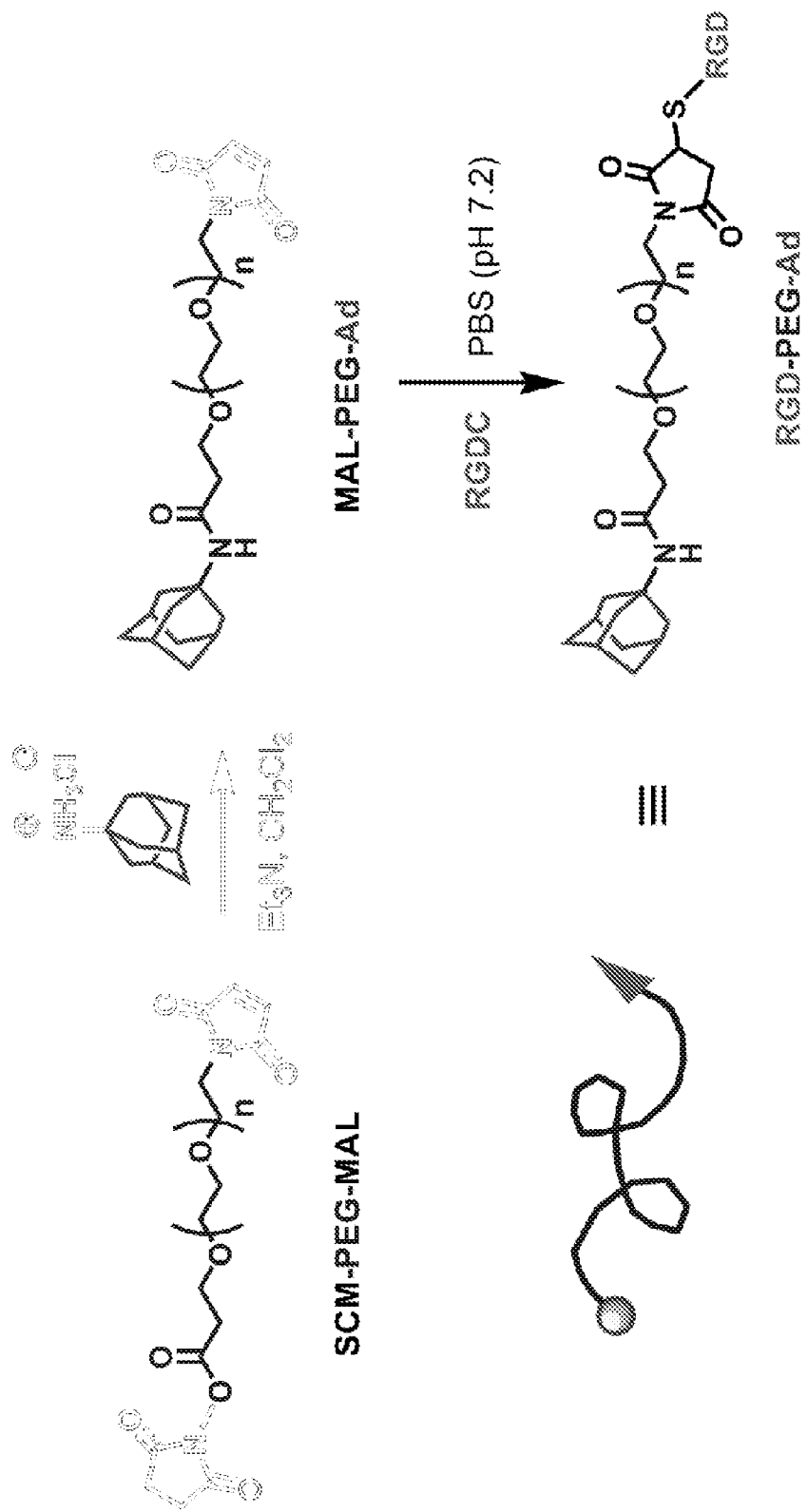
FIG. 42 shows the synthesis of RGD-PEG-Ad from 1-adamantanamine hydrochloride and SCM-PEG-MAL, and addition of RGDC.

Synthesis of RGD-PEG-Ad (FIG. 42)

To a solution of 1-adamantanamine hydrochloride (0.94 mg, 5 μmol, 5.0 equiv.) in 1 mL $CH_2Cl_2$, triethylamine (0.6 mg, 5 μmol, 5.0 equiv.) and SCM-PEG-MAL (5 mg, 1.0 μmol, 1.0 equiv.) were added in sequence. The reaction mixture was stirred at room temperature for 2 h. After the reaction, the solvent was subsequently removed in vacuo, and the PBS buffer solution (1 mL) containing RGDC (2.25 mg, 5.0 μmol, 5.0 equiv.) was added to the reaction residue. The mixture was stirred for another 2 h at room temperature, followed by remove of insoluble 1-adamantanamine by filtration. The solution was then dialyzed with Slide-A-Lyzer® dialysis cassette (MWCO, 2 kD) against water overnight and lyophilized to give RGD-PEG-Ad (3.4 mg, 0.63 μmol), a white powder in 63% yield. $^1$H NMR (400 MHz, DMSO-d6): δ 7.83-9.12 (br, protons on RGD), 3.42-3.54 (br, protons on PEG), 1.13-1.18 (br, protons on Ad). MS (MALDI-TOF, positive mode, DHB): the observed Mn for SCM-PEG-MAL was 5373.49; the $M_n$ value of RGD-PEG-Ad based on the SCM-PEG-MAL was calculated as 5859.78 $(M+H)^+$. found: 5859.33.

Figure 43:
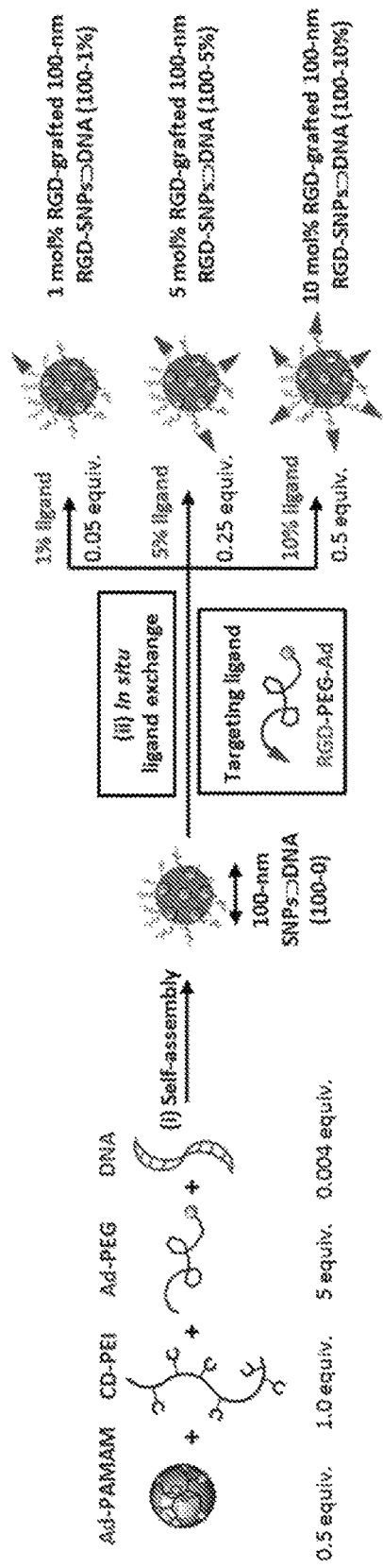
FIG. 43 shows the preparation of 100-0 SNPs-DNA, 100-1% RDG-SNPs-DNA, 100-5% RGD-SNPs-DNA and 100-10% RGD-SNPs-DNA, from CD-PEI Ad-PAMAM Ad-PEG, and DNA, and addition of RGD-PEG-Ad.

Preparation of 100-0 SNPs-DNA, 100-1% RGD-SNPs-DNA, 100-5% RGD-SNPs-DNA and 100-10% RGD-SNPs-DNA (FIG. 43)

To a solution of CD-PEI (15 μg, 0.84 nmol) in 750 μL PBS solution (pH=7.2), the mixture of Ad-PAMAM (1.2 μg, 0.42 nmol), Ad-PEG (21.0 μg, 4.2 nmol) and DNA (7.5 μg, 3.4 pmol) in 750 μL PBS solution was added slowly via a Hamilton syringe under vigorous stirring. The 100-0 SNPs-DNA was obtained after the mixture was incubated at room temperature for 20 min. The resulting solution was split into four aliquots, and three of them were subjected to in situ ligand exchange by adding PBS solutions (10 μL) containing 246 ng (0.042 nmol), 1230 ng (0.21 nmol) and 2460 ng (0.42 nmol) of RGD-PEG-Ad, respectively. Three mixtures were incubated for another 20 min at room temperature to obtain 100-1% RGD-SNPs-DNA, 100-5% RGD-SNPs-DNA and 100-10% RGD-SNPs-DNA, respectively.

Figure 44:
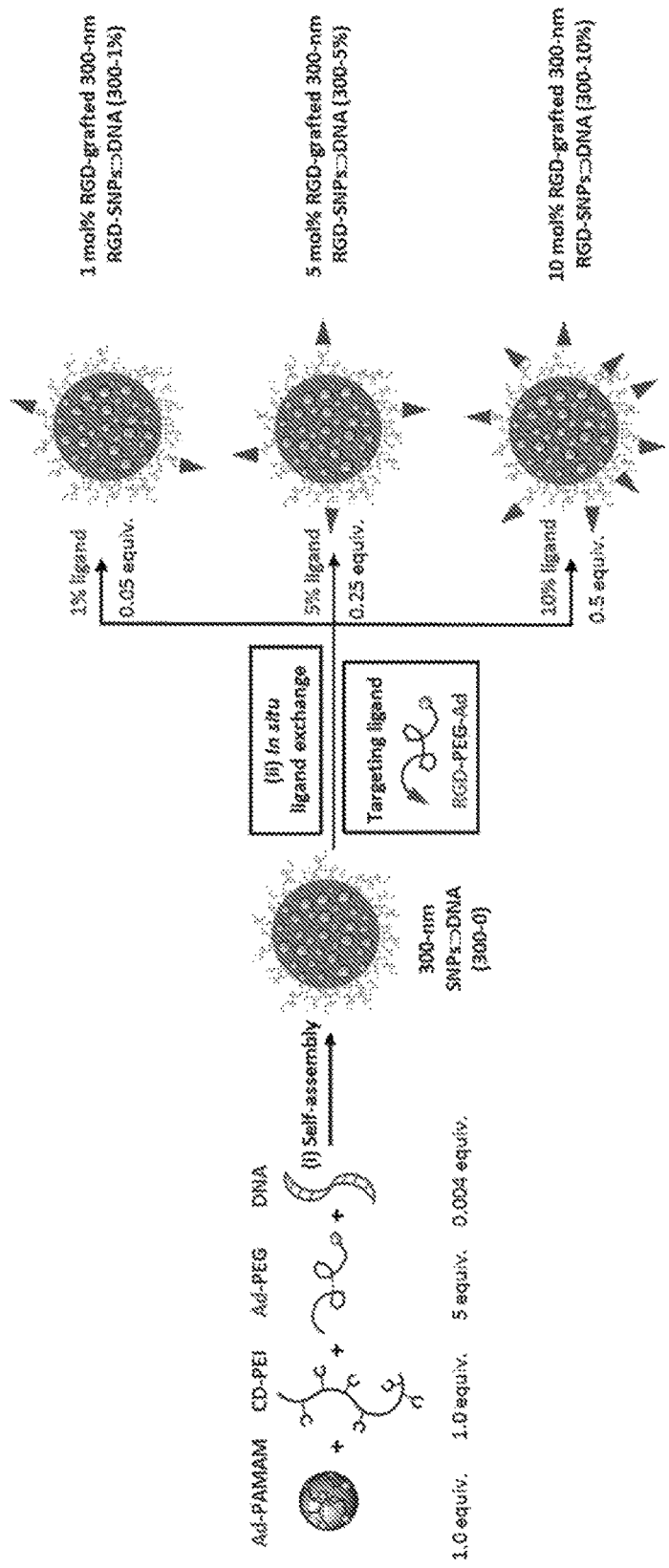
FIG. 44 shows the preparation of 300-0 SNPs-DNA, 300-1% RDG-SNPs-DNA, 300-5% RGD-SNPs-DNA and 300-10% RGD-SNPs-DNA from CD-PEI Ad-PAMAM Ad-PEG and DNA and addition of RGD-PEG-Ad.

Preparation of 300-0 SNPs-DNA, 300-1% RGD-SNPs-DNA, 300-5% RGD-SNPs-DNA and 300-10% RGD-SNPs-DNA. (FIG. 44)

In a similar manner, CD-PEI (15 μg, 0.84 nmol) Ad-PAMAM (2.4 μg, 0.84 nmol), Ad-PEG (21.0 μg, 4.2 nmol), DNA (7.5 μg, 3.4 μmol) were mixed to prepare 300-0 SNPs-DNA. Subsequently, 246 ng (0.042 nmol), 1230 ng (0.21 nmol) and 2460 ng (0.42 nmol) of RGD-PEG-Ad were used to obtain 300-1% RGD-SNPs-DNA, 300-5% RGD-SNPs-DNA and 300-10% RGD-SNPs-DNA, respectively.

Dynamic Light Scattering (DLS)

Figure 14:
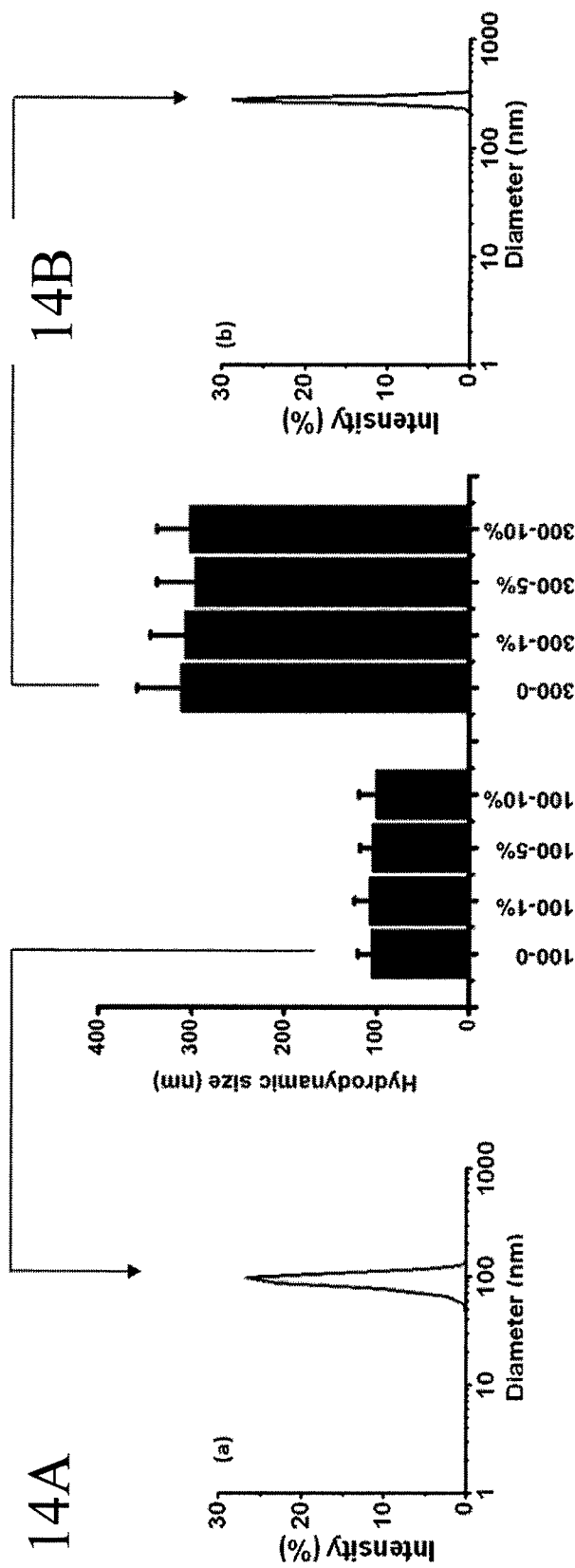
FIG. 14 shows the hydrodynamic sizes of 100-nm and 300-nm SNPs-DNA and RGD-SNPs-DNA in PBS (pH 7.2) solution measured by DLS. The DLS curves of 100-0 SNPs-DNA and 300-0 SNPs-DNA were shown in FIG. 14A and FIG. 14B, respectively.

DLS experiments were performed with a Zetasizer Nano instrument (Malvern Instruments Ltd., United Kingdom) equipped with a 10-mW helium-neon laser (λ=632.8 nm) and thermoelectric temperature controller. Measurements were taken at a 90° scattering angle. The sizes and the standard derivations of assembled SNPs-DNA and RGD-SNPs-DNA were calculated by averaging the values of at least three measurements (FIG. 14).

Transmission Electron Microscope (TEM)

Figure 15:
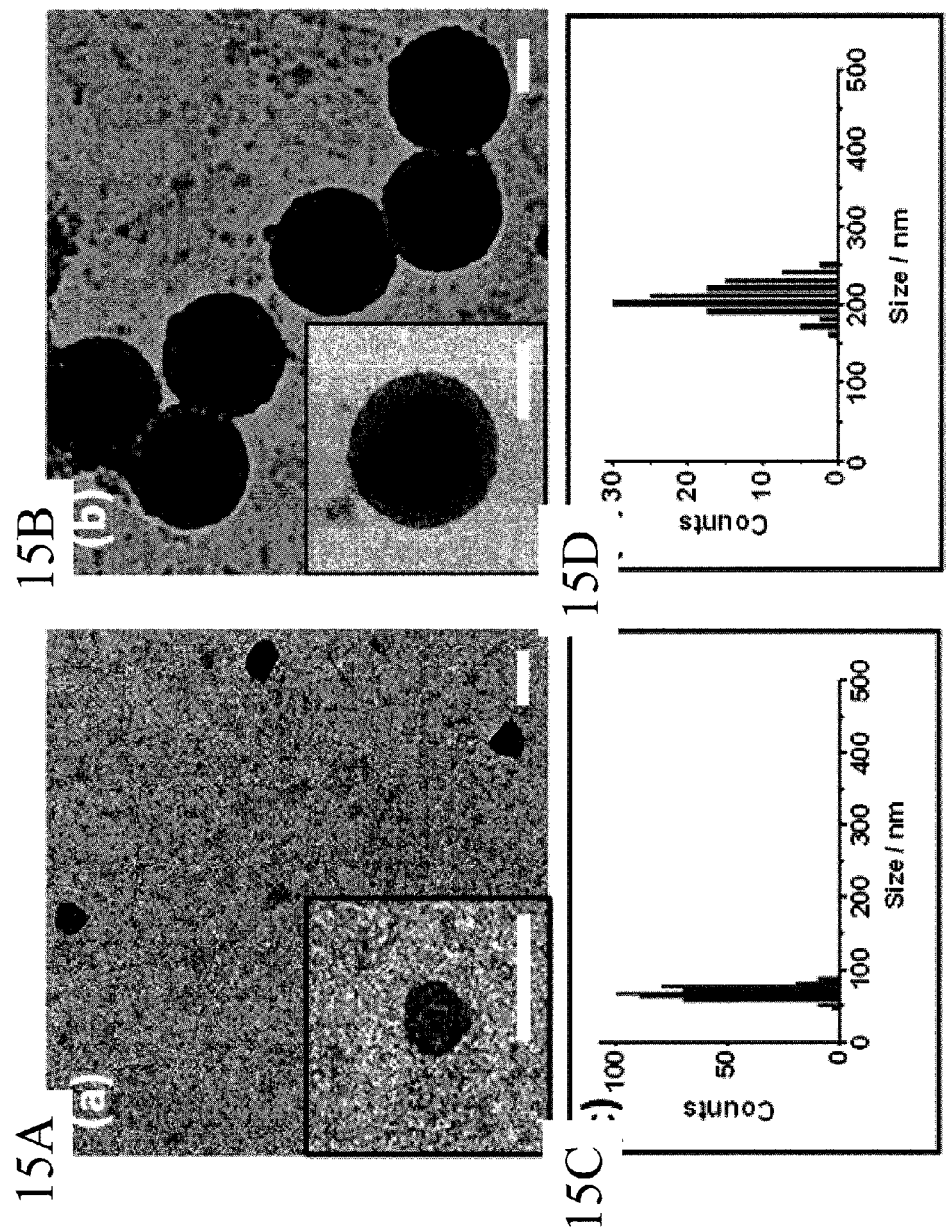
FIG. 15 shows TEM micrographs of 100-nm SNPs-DNA (FIG. 15A) and 300-nm SNPs-DNA (FIG. 15B). Insets: the respective higher magnification TEM images. Scale bars: 100 nm.

The morphology and sizes of SNPs-DNA and RGD-SNPs-DNA were directly examined using transmission electron microscope. The studies were carried out on a Philips CM 120 electron microscope, operating at an acceleration voltage of 120 kV. The TEM samples were prepared by drop-coating 2 μL of SNPs-DNA or RGD-SNPs-DNA solutions onto carbon-coated copper grids. Excess amounts of droplets were removed by filter papers after 45 s. Subsequently, the surface-deposited SNPs-DNA or RGD-SNPs-DNA were negatively stained with 2% uranyl acetate for 45 s before the TEM studies (FIG. 15). The sizes of SNPs-DNA observed by TEM were 62±8 nm for 100-0 SNPs-DNA and 210±24 nm for 300-0 SNPs-DNA. The reduced sizes obtained by TEM were attributed to the dehydration of SNPs-DNA during the TEM sample preparation (Ito, T.; Sun, L.; Bevan, M. A.; Crooks, R. M. *Langmuir,* 2004, 20, 6940-6945).

Zeta Potential Measurements

Figure 16:
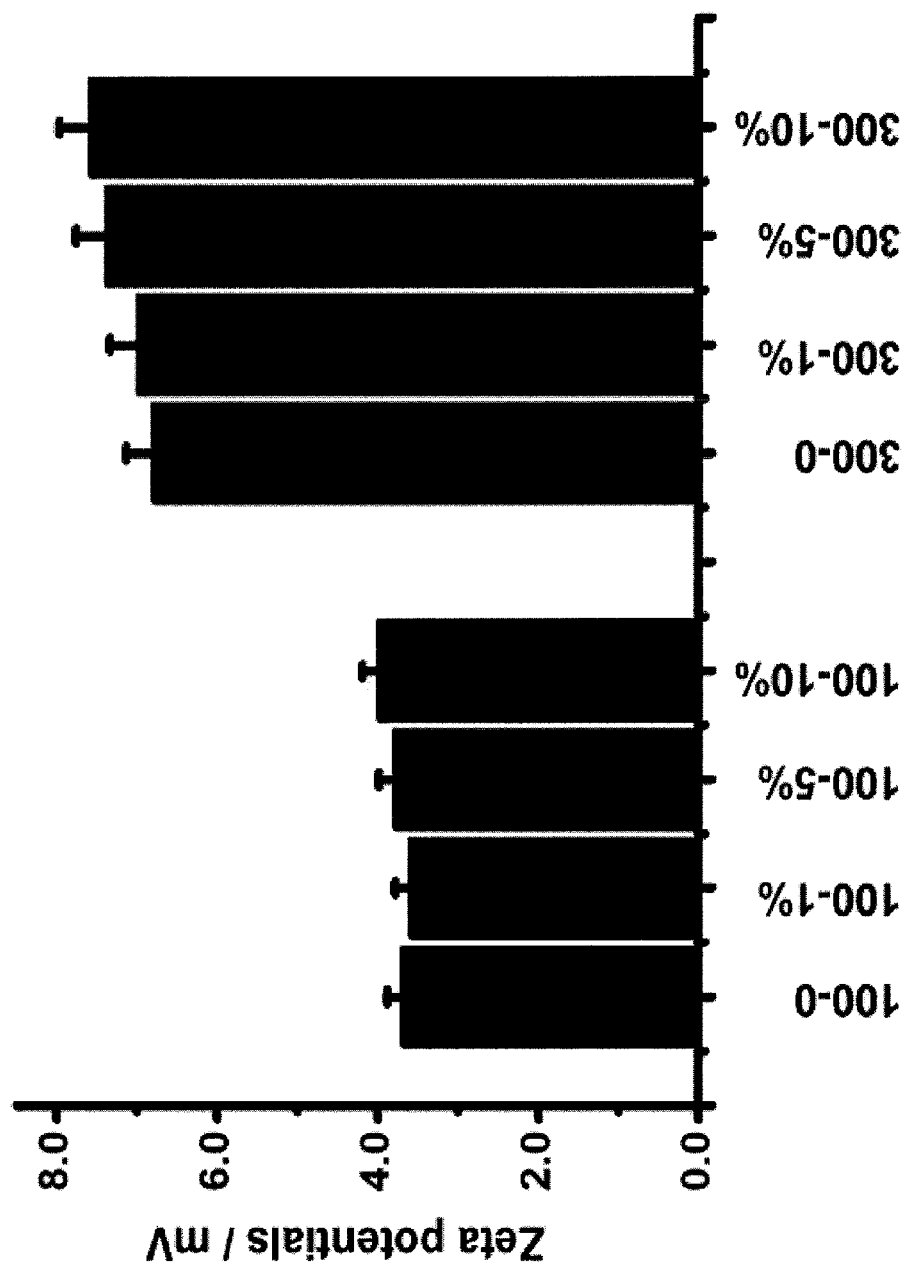
FIG. 16 shows zeta potential variations of SNPs-DNA and RGD-SNPs-DNA in PBS buffer solution (pH 7.2). Error bars were obtained from three independent measurements.

Zeta potentials of SNPs-DNA and RGD-SNPs-DNA were determined by photon correlation spectroscopy using a Zetasizer Nano instrument, (Malvern Instruments, Malvern, Worcestershire, UK). The measurements were performed at 25° C. with a detection angle of 90°, and the raw data were subsequently correlated to Z average mean size using a cumulative analysis by the Zetasizer software package (FIG. 16).

Cell Cultures

3T3 and U87 cell lines were routinely maintained in DMEM containing 10% fetal bovine serum (FBS) and 1% penicillin/streptomycin (Invitrogen, Carlsbad, Calif.). MCF7 was cultured in EMEM containing 10% fetal bovine serum (FBS) and 1% penicillin/streptomycin.

$α_vβ_3$ High-Expressed 3T3 Cells

The $α_vβ_3$ high-expressed 3T3 cells were generated by passaging normal cultured 3T3 cells using scraping-collection. Cells that were detached via scraping resulted in high densities of $α_vβ_3$ integrins on the cell surface. These cells are referred to as $α_vβ_3$ high-expressed 3T3 cells.

$\alpha_v\beta_3$ Low-Expressed 3T3 Cells

The $\alpha_v\beta_3$ low-expressed 3T3 cells were generated by passaging the normal cultured cells using 0.25% trypsin. Trypsin, an enzyme that acts to degrade protein, can be used to cleave the integrins on the cell surface (Rawlings et al., *Meth. Enzymol.*, vol. 244, pp. 19-61, 1994). Cells that were detached using 0.25% trypsin (Ng et al., *Mol. Ther.*, vol. 17, pp. 8282-836, 2009) resulted in low densities of $\alpha_v\beta_3$ integrins on the cell surface. These cells are referred to as $\alpha_v\beta_3$ low-expressed 3T3 cells.

Transfection Procedure

Cells ($1\times10^4$ cells/well) were plated in an 8-well chamber slides and allowed to adhere overnight. EGFP-encoded DNA was diluted in 1×TE buffer. SNPs-DNA with 100 and 300-nm sizes for the gene transfection studies were separately prepared. Each SNPs-DNA or RGD-SNPs-DNA (20 μL) was diluted with 200 μL Opti-MEM medium and, subsequently, transferred to each well. For the control groups, bare DNA (2.2 nM), the complex of CD-PEI (600 nM) with DNA (2.2 nM) and the complex of CD-PEI (600 nM)/Ad-PEG (3 μM) with DNA (2.2 nM) were prepared in PBS buffer (20 μL). Each control sample was diluted with 200 μL Opti-MEM medium and transferred to each well of an 8-well chamber slide (Lab-Tek®, Electron Microscopy Sciences, PA). RGD-jet-PEI was used as a standard transfection reagent and operated according to the protocol provided by the manufacturer. SNPs-DNA and RGD-SNPs-DNA along with controls were incubated with the cells for 4 hours, then removed by aspirating, and replaced with 400 μL/well of fresh regular DMEM/EMEM culture medium. Cells were allowed to grow for 24 h at 37° C. and 5% CO2 and then fixed (4% paraformaldehyde for 15 min at room temperature), washed with PBS three times, stained with DAPI and a final PBS rinse prior to EGFP expression analysis by fluorescence microscope.

Microscope Settings, Imaging Processing and Data Analyzing

The 8-well chamber slide was mounted onto a Nikon TE2000S inverted fluorescent microscope with a CCD camera (Photomatrix, Cascade II), X-Cite 120 Mercury lamp, automatic stage, and filters for three fluorescent channels (W1 (DAPI), W2 (EGFP and AO) and W3 (PI)). Following image acquisition, MetaMorph (Molecular Devices, Version 7.5.6.0) was used to quantify EGFP expressed cells. The Multi-Wavelength Cell Scoring module of the Metamorph software allows image analysis. A nuclei counting application in the module allows us to calculate the total cell number. In order to determine the gene transfection efficiency, the EGFP-expressed cell number was counted by the MetaMorph program that distinguishes the transfected cells from the non-transfected cells. The fluorescence intensity difference between the regular cultured cells and background around 200~300 is measured as a baseline. The cell fluorescence intensity difference between cells and background above 300 are recognized as the transfected cells. The gene transfection efficiency was obtained by the EGFP-expressed cell number divided by the total cell number.

Cell Viability Assay

Figure 17:
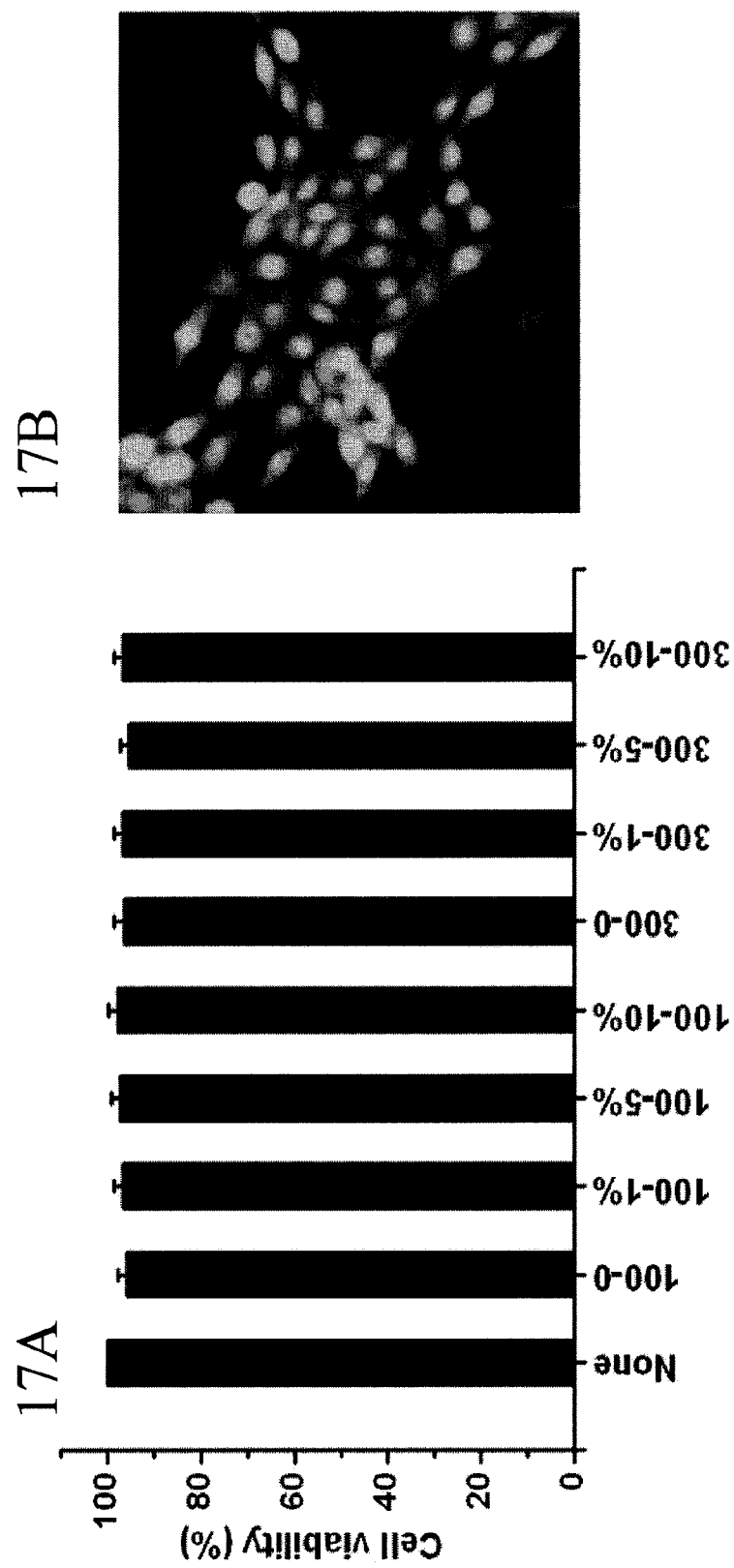
FIG. 17 shows cell viability results.

To determine the number of dead and live cells after transfection, two fluorescent dyes were used. Propidium iodide (PI) is a fluorescent dye that cannot pass through intact cell membranes but readily passes through damaged membranes and binds with DNA. PI fluorescence was bright red when exposed to UV light. The presence of PI in a cell indicates that the cell membrane integrity has been compromised and that the cell is severely damaged. Red fluorescent cells are judged non-viable. Acridine orange (AO) is a fluorescent dye that readily passes through all cell membranes and stains the cytoplasm and nucleus bright green when exposed to UV light. Green fluorescent cells are judged viable. All dyes were used in accordance with the manufacturer's directions. First, 1 mL of 10×AO solution and 1 mL of 10×PI solution were added into 8 mL of PBS in a 15 mL tube to make the AO/PI working solution. Then, approximately 0.5 mL AO/PI working solution was added into each well. Using the fluorescence microscope, images were taken and the viability of the cells transfected by SNPs-DNA and RGD-SNPs-DNA and the cells cultured in the normal medium were evaluated. There were no significant differences in viability, which suggested that the toxicity of SNPs-DNA and RGD-SNPs-DNA were negligible for in vitro transfection studies (FIG. 17).

Discussion

Figure 18:
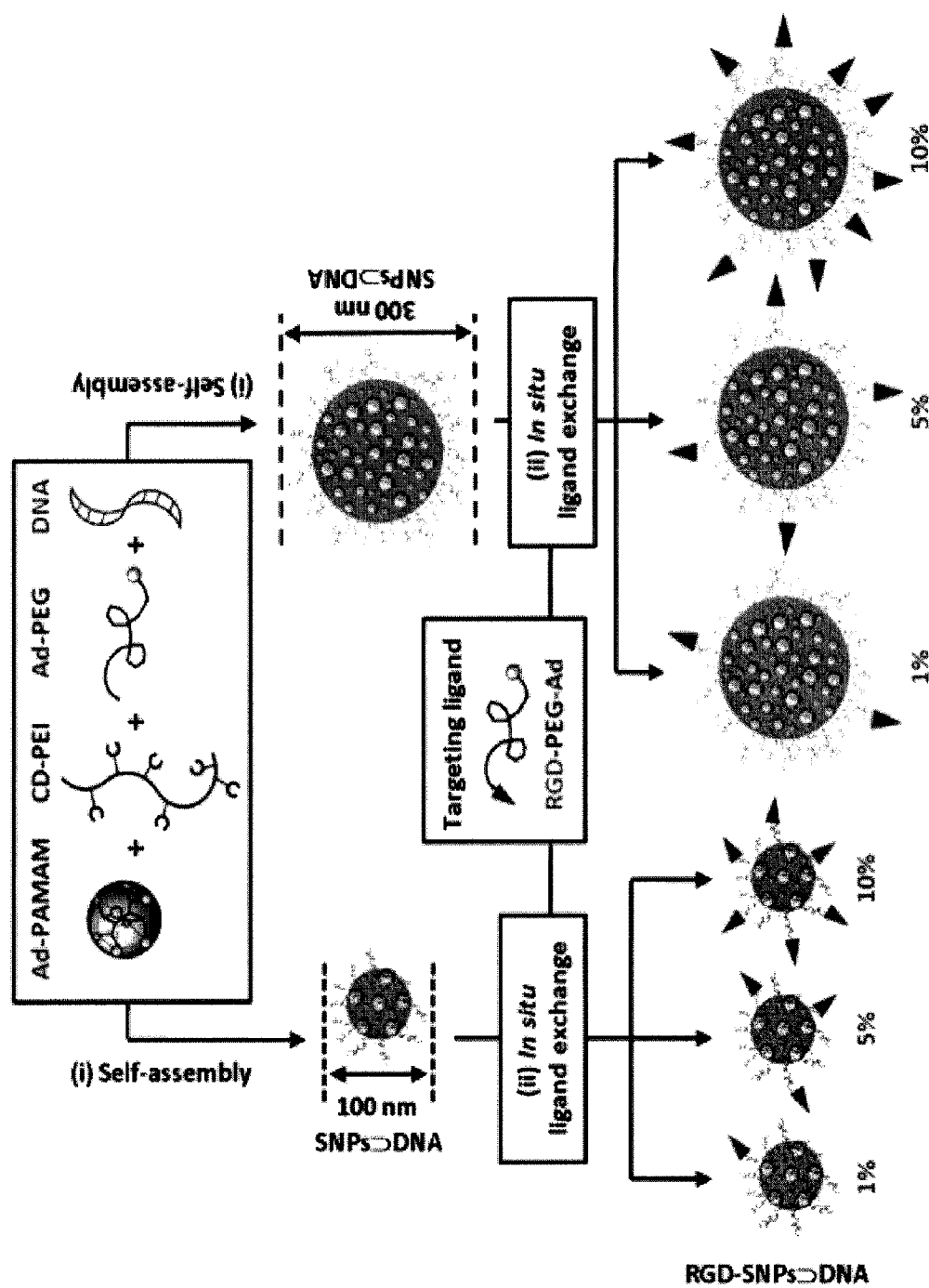
FIG. 18 shows a two-step modular assembly approach for preparation of a small library of DNA-encapsulated supramolecular nanoparticles (SNPs-DNA and RGD-SNPs-DNA) with controllable sizes and tunable RGD ligand coverage.

Here, the supramolecular assembly approach was used to prepare a small library of DNA-encapsulated SNPs (SNPs-DNA and RGD-SNPs-DNA, FIG. 18) with controllable sizes and tunable surface coverage of a targeting ligand, i.e., arginine-glycine-aspartic (RGD) peptide. A two-step preparation process was to first generate both 100 and 300-nm SNPs-DNA from Ad-PAMAM, CD-PEI, Ad-PEG and DNA, followed by in situ RGD ligand exchange of SNPs-DNA to give six different RGD-SNPs-DNA with ligand coverage of 1, 5 and 10 mol % (based on Ad-PEG). In this proof-of-concept study, A plasmid DNA encoded with an enhanced green fluorescent protein (EGFP) driven by a CMV promoter was used as a reporter system, and the RGD ligand (Liu et al., *Nat. Nanotech.*, vol. 2, pp. 47-52, 2007) was employed to recognize the $\alpha_v\beta_3$ integrin receptor on the membranes of certain types of tumor cells. The sizes, morphologies and surface charges of the resulting SNPs-DNA and RGD-SNPs-DNA were characterized by dynamic light scattering (DLS), transmission electron microscope (TEM) and zeta potential measurements, respectively. Finally, the gene transfection efficiency and specificity of each SNPs-DNA and RGD-SNPs-DNA in the small library were examined using $\alpha_v\beta_3$ high-expressed and low-expressed cells, along with the control delivery systems.

DNA Loading

The DNA loading capacity to be used for preparation of SNPs-DNA and RGD-SNPs-DNA was determined. Similar to cationic polymer based gene delivery systems (Srinivasachari et al., *Biomaterials*, vol. 30, pp. 928-938, 2009; Li et al., *Adv. Mater.*, vol. 18, pp. 2969-2970, 2006), the DNA loading capacity of SNPs depends on the net cationic charges embedded in the interior Ad-PAMAM/CD-PEI hydrogel network. Electrophoresis analysis (Zugates et al., *J. Am. Chem. Soc.*, vol. 128, pp. 12726-12734, 2006). and ethidium bromide exclusion assay (Meyer et al., *J. Am. Chem. Soc.*, vol. 130, pp. 3272-3273, 2008) were utilized to measure the DNA loading capacity of the Ad-PAMAM/CD-PEI hydrogel (FIGS. 12 and 13), resulting in the respective nitrogen-phosphate (N/P) ratios of 2.6 and 5.0. The N/P ratio of 5.0 was chosen to ensure complete DNA encapsulation. Next, SNPs-DNA with 100 and 300-nm diameters were prepared separately by slowly adding a PBS solution (pH=7.2) of CD-PEI (600 nM) into PBS solution containing Ad-PAMAM (300 nM for 100-nm SNPs-DNA and 600 nM for 300-nm SNPs-DNA), Ad-PEG (3 μM) and DNA (2.2 nM), followed by incubation at room temperature for 20 min. The DLS measurements indicated that the hydrodynamic sizes of the 100 and 300-nm SNPs-DNA were 106±14 and 312±47 nm, respectively.

Cell Targeting—Preparation

Subsequently, the samples of each size of SNPs-DNA were split into four aliquots, and three of them were subjected to the in situ ligand exchange by adding 30, 150 or 300 nM of RGD-PEG-Ad. A collection of RGD-SNPs-DNA with different RGD coverage (when mixing ratios of RGD target ligand were 1, 5 and 10%, the actual RGD ligand coverages on the 100-nm RGD-SNPs-DNA were 0.8±0.2%, 2.9±0.5% and 6.7±0.8%, respectively. For 300-nm RGD-SNPs-DNA, the RGD ligand coverages were 0.9±0.2%, 2.2±0.4% and 6.7±0.6%, respectively), namely 100-1%, 100-5%, 100-10%, 300-1%, 300-5% and 300-10%, were obtained accordingly. After in situ ligand exchange, the hydrodynamic sizes of RGD-SNPs-DNA exhibited negligible changes (<5%, FIG. 14). The morphologies of SNPs-DNA and RGD-SNPs-DNA were examined using TEM. The TEM images (FIG. 15) showed smaller sizes (62±8 for 100-nm SNPs-DNA and 210±24 nm for 300-nm SNPs-DNA), spherical shapes and narrow size distributions of SNPs-DNA and RGD-SNPs-DNA. Zeta potential measurements indicated that the surface-charge densities of 100 and 300-nm SNPs-DNA were 3.7±0.4 and 6.8±0.5 mV, respectively. After ligand exchange, small increases (3-11%) in zeta potentials of RGD-SNPs-DNA were observed (FIG. 16).

Transfection

An in vitro EGFP transfection study of a collection of SNPs-DNA and RGD-SNPs-DNA was performed along with controls, i.e., DNA, DNA complexes of CD-PEI, CD-PEI/Ad-PEG and RGD-jet-PEI, in 8-well chamber slides containing two $\alpha_v\beta_3$ high-expressed cells (i.e., U87 and scraping-collected 3T3 cells) (Ng et al., Mol. Ther., vol. 17, pp. 828-836, 2009) and two $\alpha_v\beta_3$ low-expressed cells (i.e., MCF7 and 0.25% trypsin-treated 3T3 cells) (Xie et al., J. Am. Chem. Soc., vol. 130, pp. 7542-7543, 2008).

Figure 19:
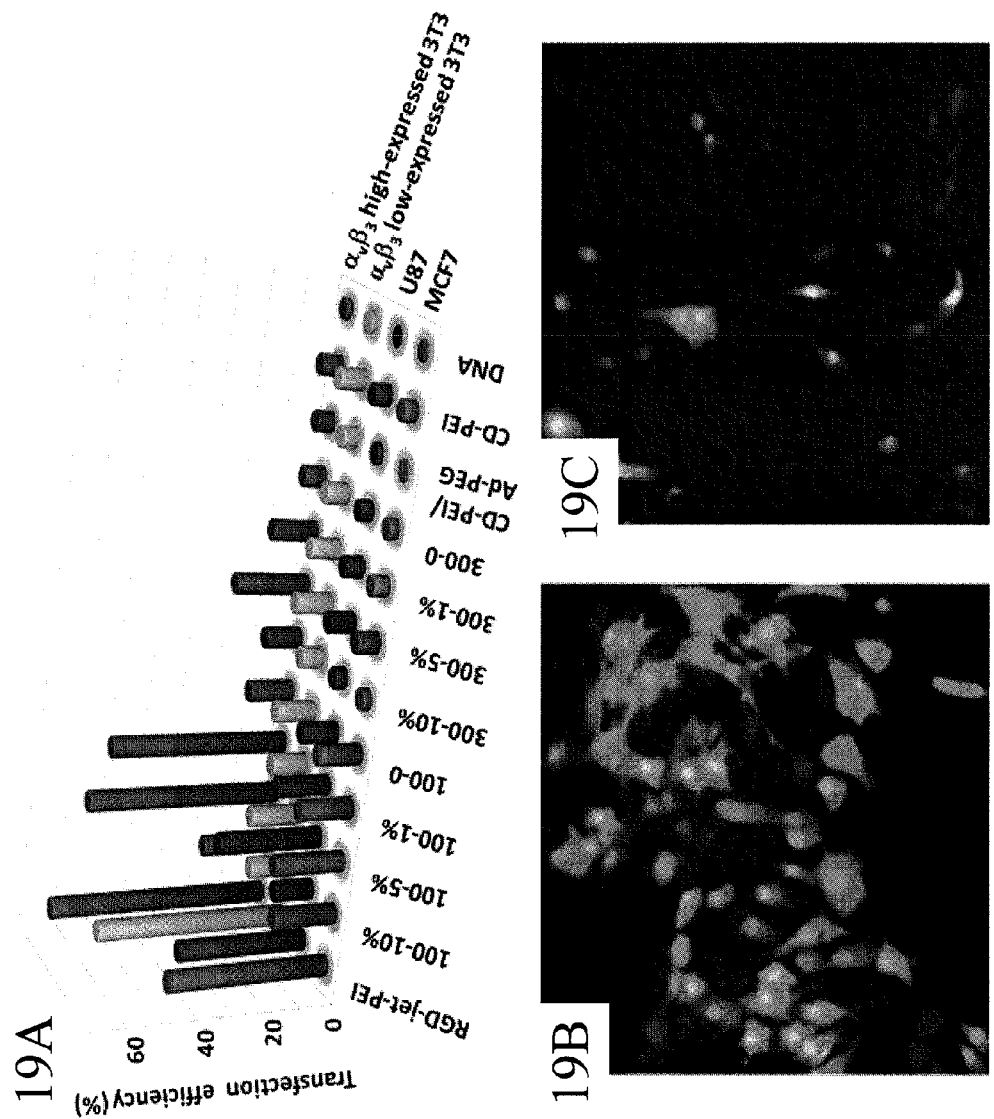
FIG. 19 shows transfection efficiency.

For the purpose of comparison, an equal amount of EGFP-encoded plasmid DNA (100 ng) was added to individual cell culture chambers in this transfection study. The resulting 48 individual EGFP transfection experiments were incubated at 37° C. (5% CO$_2$) for 24 h. After paraformaldehyde fixation and DAPI nuclear staining, a fluorescence microscope was used to quantify the EGFP expression levels in individual cells. These levels were then used to determine the transfection efficiency for each vehicle. The transfection study was repeated three times, and the results of average transfection efficiency of gene delivery vehicles for different cell lines are summarized in FIG. 19. First, DNA complexes based on each of the molecular building blocks (CD-PEI and CD-PEI/Ad-PEG) gave very poor transfection performance similar to free plasmid DNA, indicating that the formation of supramolecular nanoparticles is crucial for achieving enhanced transfection efficiency. Second, it is apparent that 100-nm RGD-SNPs-DNA exhibited higher transfection efficiency than those of 300-nm analogues. This observation is consistent with the results from the reported polymer-based gene delivery systems (Davis et al., Nat. Rev. Drug Discov., vol. 7, pp. 771-782, 2008; Yu et al., Curr. Opinion Mol. Ther., vol. 11, pp. 165-178, 2009; Fukushima et al., J. Am. Chem. Soc., vol. 127, pp. 2810-2811, 2005), in which vehicles with 10-100 nm size range display better gene transfection efficiency (Wang et al., Angew. Chem. Int. Ed., vol. 48, pp. 4344-4348, 2009). Third, 100-5% RGD-SNPs-DNA gave the highest transfection efficiency compared to those observed for SNPs-DNA and other targeted RGD-SNPs-DNA. The reduced transfection efficiency observed for 100-10% RGD-SNPs-DNA can be attributed to an excess amount of free RGD ligand in the culture medium, which compromised the targeted binding of RGD-SNPs-DNA as a result of a competition effect (Bazin et al., Chem. Commun., pp. 5004-5006, 2008). Overall, 100-5% RGD-SNPs-DNA demonstrated the best transfection efficiencies (57±11% and 31±8% for $\alpha_v\beta_3$ high-expressed 3T3 and U87, respectively). These results are comparable to those observed for the commercially available RGD-jet-PEI (64±15% and 38±9% for $\alpha_v\beta_3$ high expressed 3T3 and U87, respectively), which is a well-known selective and efficient transfection reagent for integrin-expressing cell lines (Erbacher et al., Gene Ther, vol. 6, pp. 138-145, 1999). Fourth, in addition to high transfection efficiency, 100-5% RGD-SNPs-DNA also exhibited outstanding delivery specificity to the $\alpha_v\beta_3$ high expressed cells, U87 (31±8%) and 3T3 (57±11%), over the $\alpha_v\beta_3$ low expressed cells, MCF7 (21±6%) and trypsin-treated 3T3 (15±4%). Four-fold difference in transfection efficiencies were observed for 100-5% RGD-SNPs-DNA between $\alpha_v\beta_3$ high-expressed and $\alpha_v\beta_3$ low expressed 3T3 cells, while only 1.2-fold difference was observed for RGD-jet-PEI. In contrast to non-target-specific transfection performance of RGD-jet-PEI, 100-5% RGD-SNPs-DNA had higher transfection efficiency for the U87 cell line with respect to the MCF7 cell line, which indicated good transfection specificity of RGD-SNPs-DNA for the $\alpha_v\beta_3$ high expressed cell lines. Moreover, the toxicity of SNPs-DNA and RGD-SNPs-DNA were tested by using the cell viability assay. The cells transfected by SNPs-DNA and RGD-SNPs-DNA were compared with the cells cultured in the normal medium. There were no significant differences in viability (97±2%), which suggested that the toxicity of SNPs-DNA and RGD-SNPs-DNA is negligible for in vitro transfection studies (FIG. 17).

In conclusion, a convenient, flexible and modular synthetic approach for preparation of a small library of SNPs-DNA and RGD-SNPs-DNA with different sizes and RGD ligand coverage has been demonstrated. Gene transfection studies of SNPs-DNA and RGD-SNPs-DNA library for $\alpha_v\beta_3$ high-expressed cells and $\alpha_v\beta_3$ low-expressed cells were performed. The results revealed that the size and target ligand density of RGD-SNPs-DNA play a critical role in the target-specific gene delivery.

Example 3—Combinatorial Approach to Transfection Optimization

Figure 20:
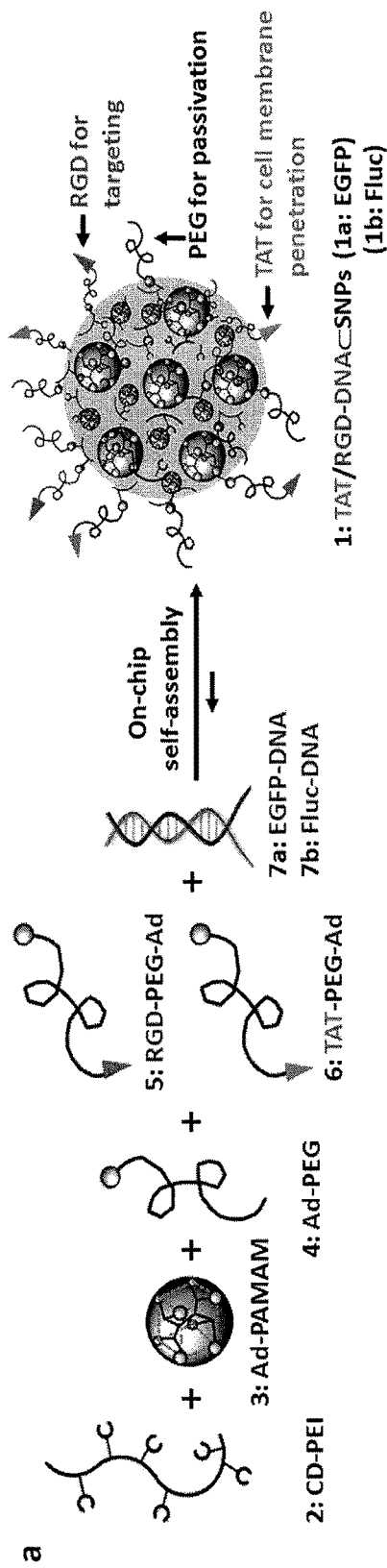
FIG. 20 shows graphical schematic representations of the self-assembly approach for producing a combinatorial library of DNA encapsulated supramolecular nanoparticles (DNA-SNPs, 1), in which a broad structure/functional diversity can be programmed into individual DNA-SNPs (1) by systematically altering the mixing ratios of the five functional molecular building blocks i.e., CD-PEI (2), Ad-PAMAM (3), Ad-PEG (4), RGD-PEG-Ad (5) and TAT-PEG-Ad (6), as well as DNA plasmid (7a: enhanced green fluorescent protein (EGFP) and 7b: fire fly luciferase (FLuc)).

A rapid developmental pathway (FIG. 20) toward highly efficient gene delivery agents is demonstrated that leverages the powers of (i) a combinatorial synthetic approach (FIG. 20) based on supramolecular assembly and (ii) an automated microreactor. Unlike the slow and multistep syntheses employed for producing the existing gene-delivery materials with limited diversity, the supramolecular approach (FIG. 20) enables a convenient, flexible and modular method for generating a combinatorial library of DNA-SNPs (1), in which a broad structural/functional diversity covering the size variation, uniformity, surface chemistry and DNA loading capacity was programmed into individual DNA-SNPs (1) by systematically altering the mixing ratios of five functional molecular building blocks (2-6) and DNA plasmid (7). To test general applicability of this approach, DNA plasmids encoded with either enhanced green fluorescent protein (EGFP, 7a) or fire-fly luciferase (FLuc, 7b) gene driven by a CMV promoter was employed for monitoring gene transfection efficiency of the DNA-SNPs (1). In order to avoid human operational errors, accelerate handling procedures, enhance experimental fidelity and achieve economical use of reagents, a digital Dual-Core Microreactor was used to allow automated sampling, dilution, metering and mixing of 2-7, resulting in a library consisting of up to 648 different DNA-SNPs (1) within 2.5 h. The delivery performance of these DNA-SNPs (1) was quantified/profiled by performing transfection studies of individual DNA-SNPs (1) in 96 well plates containing 3T3 mouse fibroblast cells (8,000 cells per well). Consequently, a small group of DNA-SNPs (1) that facilitate high levels of gene expressions was identified. Comprehensive characterization on these highly efficient DNA-SNPs gene delivery agents was performed, revealing that their improved transfection performance can be attributed to the distinct surface chemistry, Zeta potential, defined size, uniformity and DNA-releasing mechanism. Compared to the leading gene transfection agents, the identified highly efficient TAT/RGD-DNA-SNPs (1) exhibited significantly improved gene transfection efficiency and low toxicity in a number of cell lines and primary cells.

Preparation

The five molecular building blocks (FIG. 20)—CD-PEI (2), Ad-PAMAM (3), Ad-PEG (4), RGD-PEG-Ad (5) and TAT-PEG-Ad (6) with designated functions were prepared and fully characterized. As indicated previously, the complementary CD-PEI (2) and Ad-PAMAM (3) are responsible for constructing cationic CD-PEI/Ad-PAMAM hydrogel networks that can encapsulate anionic DNA (1) to form the cores of DNA-SNPs (1). It is conceivable that the DNA loading capacity of DNA-SNPs (1) is dependent on net positive charges embedded in the hydrogel networks and were determined by measuring the nitrogen/phosphate ratios of DNA-SNPs (1). In this system, Ad-PEG (4) serves as a capping/solvation agent that not only constrains continuous growth of the DNA-encapsulated hydrogel networks, but also confers desired water solubility, structural stability and passivation performance to the resulting DNA-SNPs (1). Such a supramolecular assembly also allows convenient incorporation of functional ligands, i.e., Ad-PEG-RGD (5) and Ad-PEG-TAT (6), enabling delivery specificity (to recognize a certain population of cells with avb3-integrin receptors) and cell transfusion capability (to foster internalization through membrane) to the resulting TAT/RGD-DNA-SNPs (1), respectively. By systematically altering the mixing ratios among the five molecular building blocks (2-6) and DNA (7), structural/functional diversity covering sizes, uniformity, surface chemistry and DNA loading capacity can be programmed into individual TAT/RGD-DNA-SNPs (1) in the resulting combinatorial libraries. In contrast to the lipid-like gene delivery materials where the diversity of the resulting combinatorial library is attributed to a binary combination of hundreds of molecular precursors, the TAT/RGD-DNA-SNPs (1) library with a comparable level of diversity were achieved from ratiometric combination of only the five molecular building blocks and DNA load.

It is feasible to manually prepare the TAT/RGD-DNA-SNPs (1) library by pipetting and mixing individual molecular building blocks and DNA loads, while potential operation errors, limited handling speed and a significant amount of sample consumption might compromise the throughput, fidelity and efficiency of the study. To overcome these challenges, a digital DCM was used to systematically program the structural/functional diversity into the TAT/RGD-DNA-SNPs (1) libraries.

By using the digital DCM, the systematic preparation of DNA-SNPs (1) libraries was achieved by modulating the mixing ratios of CD-PEI (2), RGD-PEG-Ad (5) and TAT-PEG-Ad (6) against fixed amounts of Ad-PAMAM (3), Ad-PEG (4) and plasmid DNA (7a or b). The resulting DNA-SNPs (1) libraries were incubated in the 96-well plates for 20 min at room temperature, prior to transferring to the 96-well plates containing 8000 NIH 3T3 cells in 200 µL DEME culture media in individual wells for large-scale transfection studies in parallel. The gene transfection efficiency was evaluated by either a plate reader or a Xenogene imaging system after culturing the cells at 37° C. (5% $CO_2$) for 24 h.

Figure 21:
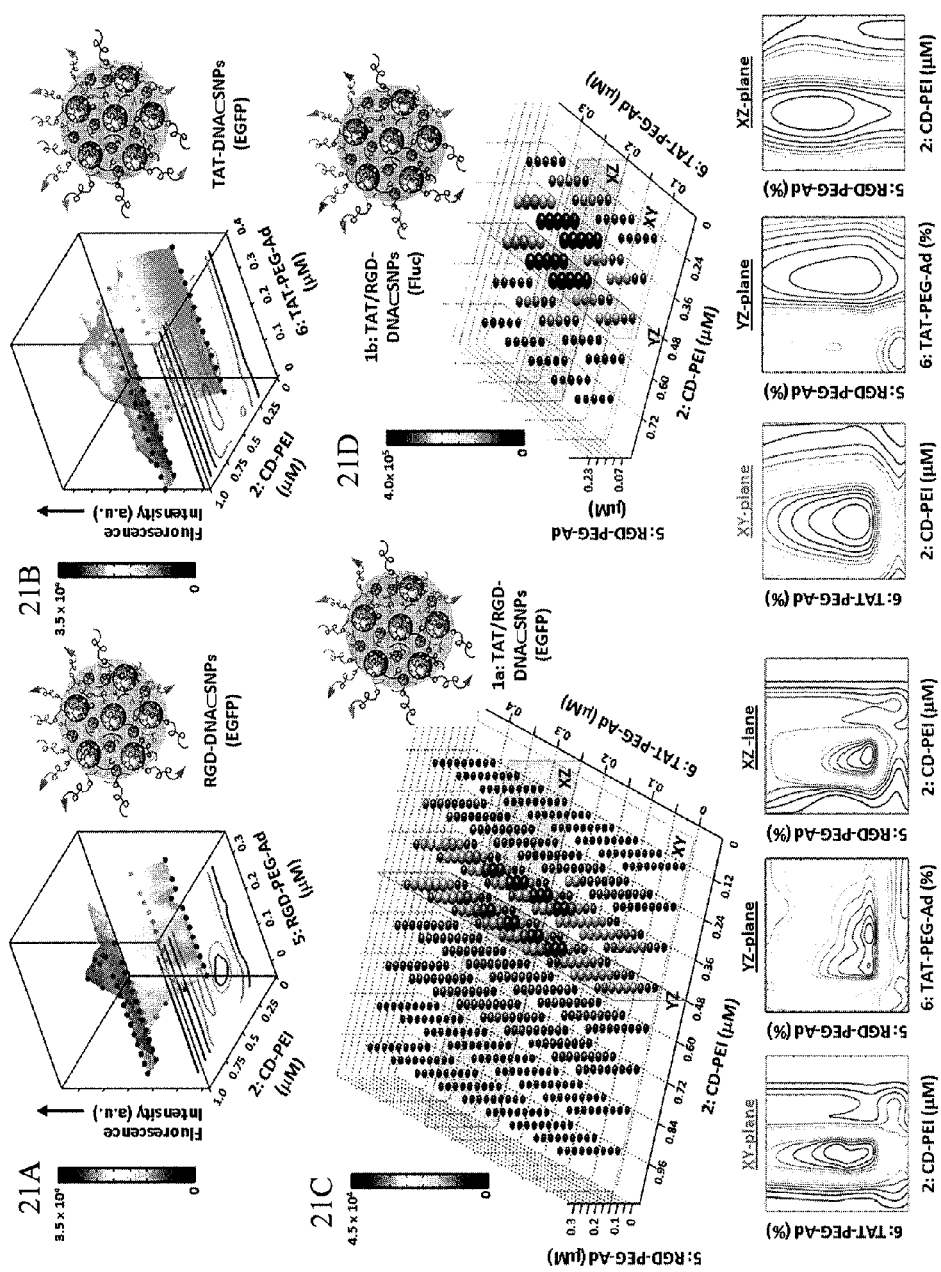
FIG. 21 shows gene transfection performance.

In proof-of-concept trials, a CMV-driven EGFP-encoded plasmid DNA was encapsulated in the DNA-SNPs (1). To prepare a full-scale screening with three variables (i.e., mixing ratios among CD-PEI (2), RGD-PEG-Ad (5) and TAT-PEG-Ad (6)), simplified studies on two pairs of variables (i.e., CD-PEI (2) vs. RGD-PEG-Ad (5) and CD-PEI (2) vs. TAT-PEG-Ad (6)) were first carried out in search of the optimal transfection performance of RGD-DNA-SNPs and TAT-DNA-SNPs, respectively. The transfection outcomes (96 data points in each case) were fitted into two 3-dimensional (3D) profiles (FIGS. 21A and 21B), in which the highest EGFP expression levels of the DNA-SNPs-transfected 3T3 cells were identified at (i) the CD-PEI (2) concentrations ranging from 0.36 to 0.48 µM, and (ii) RGD-PEG-Ad (5) or TAT-PEG-Ad (6) concentrations between 72-144 nM or 90-180 nM. The full-scale screening was accomplished by systematically programming the three variables, i.e., CD-PEI (2) ×8 concentrations, RGD-PEG-Ad (5) ×9 and TAT-PEG-Ad (6) ×9, resulting in a combinatorial library of 648 different RGD/TAT-DNA-SNPs (1a). 648 different RGD/TAT-DNA-SNPs (1a) were generated to fill seven 96-well plates (8,000 NIH 3T3 cells per well). A 4D gene expression plots was employed to conclude the full scale screening of the combinatorial library, revealing that the optimal transfection performance of RGD/TAT-DNA-SNPs (1) was achieved at (i) CD-PEI (1) concentration of 0.36-0.48 µM, a RGD-PEG-Ad (5) of 72-144 nM and TAT-PEG-Ad (5) of 90-180 nM. To validate the applicability of this developmental pathway, a relatively smaller screening was performed to identify RGD/TAT-DNA-SNPs (1b) that exhibit best transaction performance to deliver CMV-driven FLuc-encoded plasmid DNA. In this case, three variables (5×5×5 concentrations) were manipulated, resulting in a combinatorial library of 125 different RGD/TAT-DNA-SNPs (1b). Very consistent results (FIG. 21D) were observed for the transfection performance of RGD/TAT-DNA-SNPs (1b) for delivering FLuc-DNA plasmid. All the four sets of screening studies suggested very similar optimal synthetic variables for production of DNA-SNPs (1).

Figure 22:
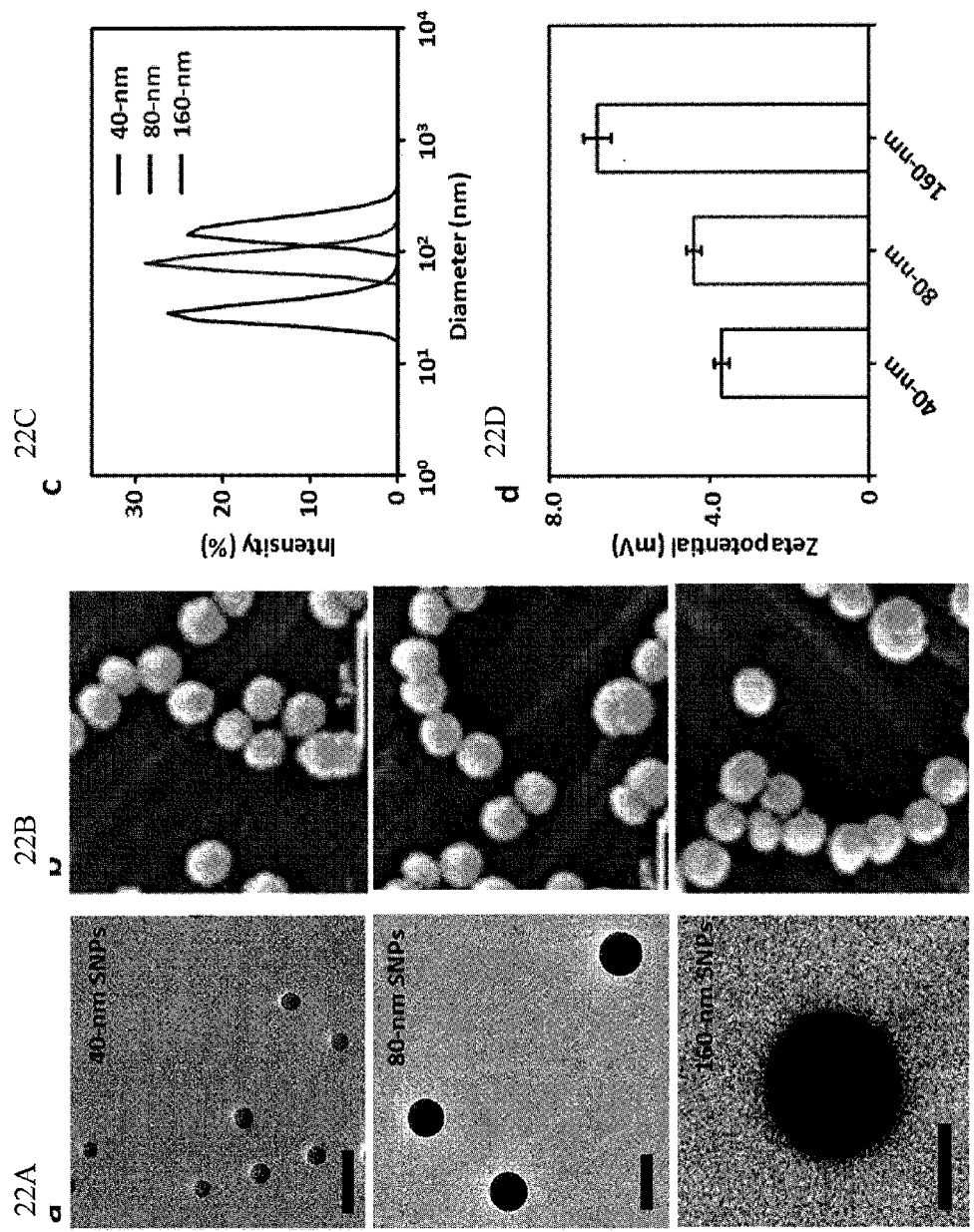
FIG. 22 shows particle size and zeta potentials.

To understand how the optimal synthetic variables affect structural properties as well as transfection performance of RGD/TAT-DNA-SNPs (1), the CD-PEI (1) mixing ratio of representative RGD/TAT-DNA-SNPs (7a) generated at different concentrations were selected, and a relatively large quantity (80 µL) of the RGD/TAT-DNA-SNPs (7) were prepared using the respective synthetic parameters ([CD-PEI (1)]=0.30, 0.40 or 0.5 µM, [RGD-PEG-Ad (4)]=5% and [TAT-PEG-Ad (5)]=9%) in the digital DCM. Continuous operation of the digital DCM generated sufficient DNA-SNPs (7) for subsequent characterizations. Both transmission electron microscopy (TEM, FIG. 22A) and scanning microscopy (SEM, FIG. 22B) were employed to examine the morphology and sizes of the resulting DNA-SNPs (7). DNA-SNPs (7) with distinct sizes of 42±4, 86±9 and 160±13 nm were obtained, corresponding to the CD-PEI (1) concentrations of 0.30, 0.40 and 0.5 µM, respectively. This result suggests that higher CD-PEI (1) mixing ratio lead to the enhanced cross-link degree of the CD-PEI (1)/Ad- PAMAM (3) hydrogel network, resulting in larger DNA-SNPs (7). The size distributions of these on-chip DNA-SNPs (7) are much narrower than those prepared manually. Dynamic light scattering (Zetasizer Nano, Malvern Instruments Ltd) measurements concurred with this observation (FIG. 22C). This improved size distribution may be attributed to the precision and reproducibility of the sampling, metering and mixing process in the microenvironment. In these cases, the 40 and 80-nm DNA-SNPs (7) exhibited the best transfection performance. Thus they were selected for further characterizations, including surface charges, stability, internalization mechanism and pH-dependent releasing mechanism.

Figure 23:
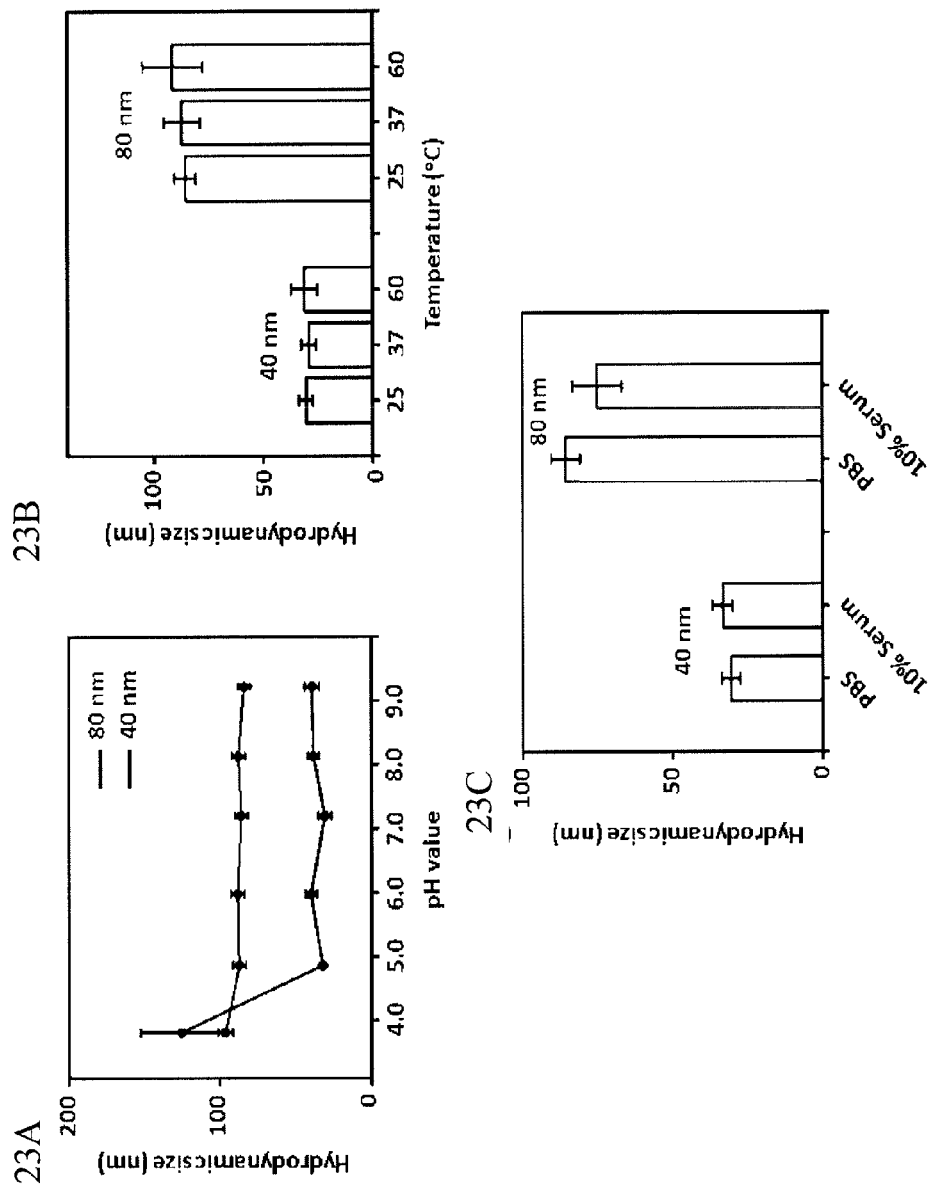
FIG. 23 shows stability studies of SNPs under different conditions.
Figure 24:
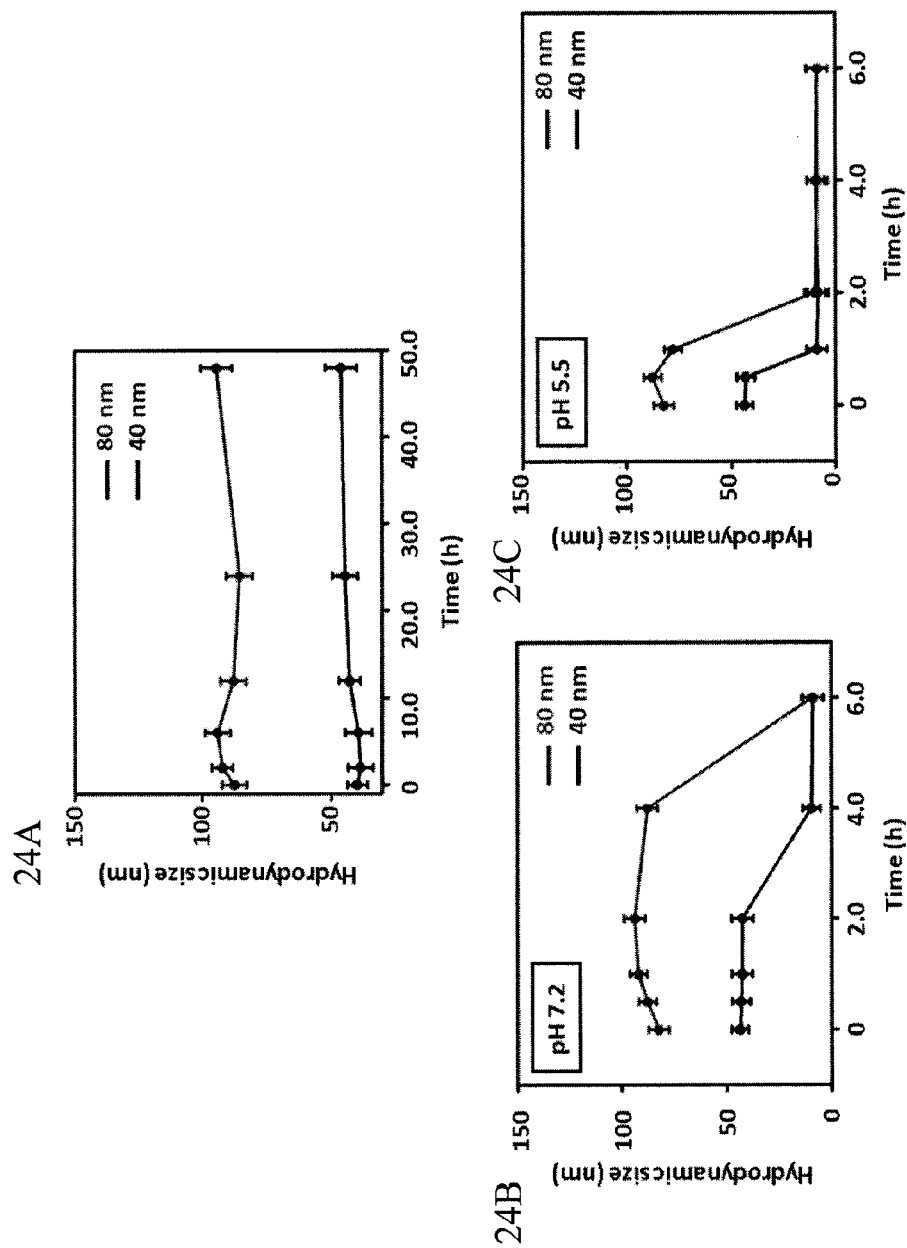
FIG. 24 shows size variation over time and at different pH.
Figure 25:
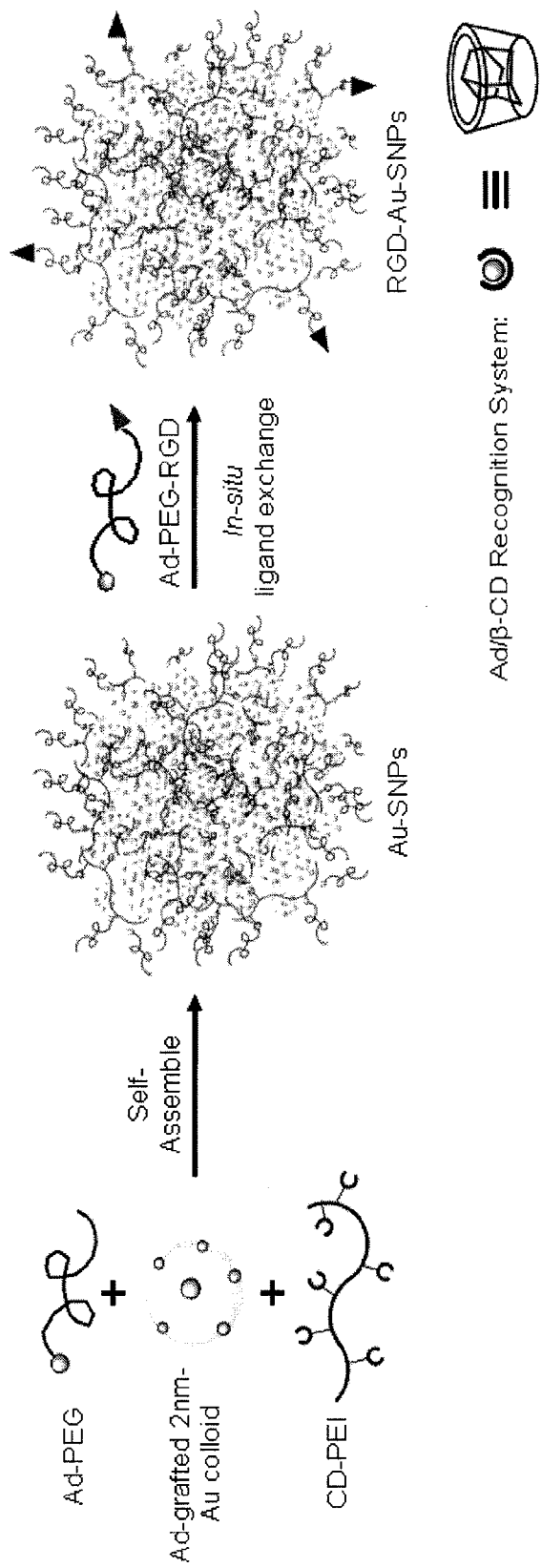
FIG. 25 shows a schematic illustration of a supramolecular synthetic approach for preparation of size-controllable gold supramolecular nanoparticles (Au-SNPs). A molecular recognition system based on adamantane (Ad) and β-cyclodextrin (CD) was employed to assemble three building blocks, i.e., Ad-grafted 2-nm Au colloids, CD-PEI and Ad-PEG. An in situ ligand exchange method was employed to introduce Ad-PEG-RGD onto Au-SNPs, resulting in RGD-Au-SNPs that could recognize a certain type of tumors cells with membrane $\alpha_v\beta_3$ integrin receptors.

The surface-charge densities of SNPs were determined by zeta potential measurements in PBS buffer solution (Zetasizer Nano, Malvern Instruments Ltd), which suggest that the SNPs carry zeta potentials in the range of (16.8) to (28.5) mV (FIG. 22D). The use of the supramolecular approach conferred dynamic characteristics to the self-assembled SNPs. To understand the dynamic stability of the SNPs, real-time DLS measurements was used to monitor the size variation of the 30 and 80 nm SNPs at different pH values, temperatures, serum and physiological ionic strength media. First, negligible size variation of the SNPs at different pH values (pH 3.8-8.3) (FIG. 23A), serum condition (FIG. 23C) and physiological ionic strengths were observed. Second, the variable-temperature DLS measurements indicate that the SNPs are stable over a wide range of temperatures (rt to 60° C., FIG. 23B). The stability of these SNPs may be attributed to the multivalent CD/Ad recognition and electrostatic interactions between anionic DNA and cationic CD-PEI and Ad-PAMAM, which holds individual molecular building blocks in each SNP. Two sets of experiments were carried out to examine the pH-dependent dynamic characteristics of these SNPs, which further validate the molecular mechanism of this supramolecular approach (FIG. 24B-C).

The observed CD-PEI (1) concentration (0.36-0.48 µM) corresponds to an N/P ratio of 4-5. This number is consistent with the maximum DNA loading capacity of the CD-PEI (1)/Ad-PAMAM (3) hydrogel network determined by both electrophoresis analysis and ethidium bromide exclusion assay.

Example 4—Gold Nanoparticle Containing Supramolecular Nanoparticles (Au-SNPs)

The supramolecular approach (Scheme 1) was used to prepare size-controllable Au-SNPs from three building blocks, namely (i) Ad-grafted 2-nm Au colloids, (ii) CD-PEI and (iii) Ad-PEG, to serve as a new type of photothermal agents. Transmission electron microscope (TEM) and zeta potential measurements were employed to characterize the sizes/morphologies and surface charge densities of the resulting Au-SNPs, respectively. Further studies were carried out to unveil the unique physical properties of the Au-SNPs, including (i) the stability at different temperatures and pH values, (ii) the size-dependant photophysical properties and (iii) the thermal-induced disassembly. Moreover, laser-induced microbubble generation experiments based on 118-nm Au-SNPs were performed to demonstrate their significantly enhanced photothermal effects compared to the 2-nm Au colloids. Taking arginine-glycine-aspartic (RGD) peptide as a targeting ligand and $\alpha_v\beta_3$-positive/negative cells as the corresponding biological system, the specificity and selectivity of RGD-Au-SNPs, generated by dynamic in-situ ligand exchange from Au-SNPs, were proved by selectively damage the $\alpha_v\beta_3$-positive cells but not the neighboring $\alpha_v\beta_3$-negative cells.

Preparation of Building Blocks

The three molecular building blocks Ad-grafted 2-nm Au colloids (FIG. 27A), CD-PEI and Ad-PEG were prepared and characterized. Size-controllable Au-SNPs (FIG. 27B) were prepared separately by slowly adding a phosphate buffered saline (PBS, pH=7.2) solution with Ad-grafted 2-nm Au colloids (0.0213 mg/mL) into PBS solutions with variable amount of CD-PEI (from 0.0725 to 5.73 mg/ml) and Ad-PEG (4.2 mg/mL), followed by incubation at room temperature overnight. By simply tuning the ratios between Ad-grafted 2-nm Au colloids and CD-PEI, a collection of Au-SNPs with variable sizes ranging between 40 and 118 nm (FIG. 27C) were obtained. The formation mechanism originally proposed for SNPs may explain the size controllability observed in Au-SNPs. In short, the mixing ratios among the three building blocks altered the equilibrium between the propagation/aggregation of the Au colloids/CD-PEI hydrogel network and the Ad-PEG-induced capping/solvation of the hydrogel network, resulting in size-controlled Au-SNPs.

General

Reagents and solvents were purchased from Sigma-Aldrich (St. Louis, Mo.) and used as received without further purification otherwise noted. 1-Adamantanamine (Ad) hydrochloride and β-cyclodextrin (β-CD) were purchased from TCI America (San Francisco, Calif.). N-hydroxysuccinimide (SCM) and maleimido (MAL) hetero-functionalized polyethylene glycol (SCM-PEG-MAL, MW=5 kD) was obtained from NANOCS Inc (New York, N.Y.). Arginine-glycine-aspartic-cysteine (RGDC) peptide was purchased from GenScript Corp (Piscataway, N.J.). CD-grafted branched polyethylenimine (CD-PEI) and Ad-grafted polyethylene glycol (Ad-PEG) were prepared as described previously. Synthesis of 2-nm Au colloids were based on Brust-Schiffrin two-phase method (Brust et al., *J. Chem. Soc. Chem. Comm.*, p. 801, 1994. Phosphate-Buffered Saline (PBS), Dulbecco's Modified Eagle Medium (DMEM), Earl's Modified Eagle's Medium (EMEM) growth medium, penicillin/streptomycin and cell labeling agent, Vybrant® DiD and DiO cell-labeling solution, were obtained from Invitrogen (Carlsbad, Calif.). Based on the introduction of manufacturer (Invitrogen), the PBS (pH 7.2±0.05) contains monobasic potassium phosphate (I=1.5 mM), sodium chloride (I=155 mM), and dibasic sodium phosphate (I=2.7 mM). U87 glioblastoma cell line and MCF7 breast cancer cell line were purchased from American Type Culture Collection. Fetal Bovine Serum (FBS) was obtained from Lonza Walkerrsville Inc (Walkerrsville, Md.). 4-well Lab-Tek™ chamber slides were purchased from Thermo Fisher Scientific.

$^1$H NMR spectra were recorded on a Bruker Avance 400 spectrometer in deuterated solvents. Mass spectra were acquired using an Applied Biosystems Voyager DE-STR MALDI-TOF mass spectrometer (Framingham, Mass.). Zeta potentials of Au-SNPs were measured on Zetasizer Nano instrument (Malvern Instruments Ltd., United Kingdom). Transmission electron microscope (TEM) images were obtained on Philips CM 120 electron microscope operating with an acceleration voltage of 120 kV. Cell imaging was performed on a Nikon TE2000S inverted fluorescent microscope with a CCD camera (Photomatrix, Cascade II), X-Cite 120 Mercury lamp, automatic stage, and filters for two fluorescent channels W1 (GFP) and W2 (Cy5).

Figure 45:
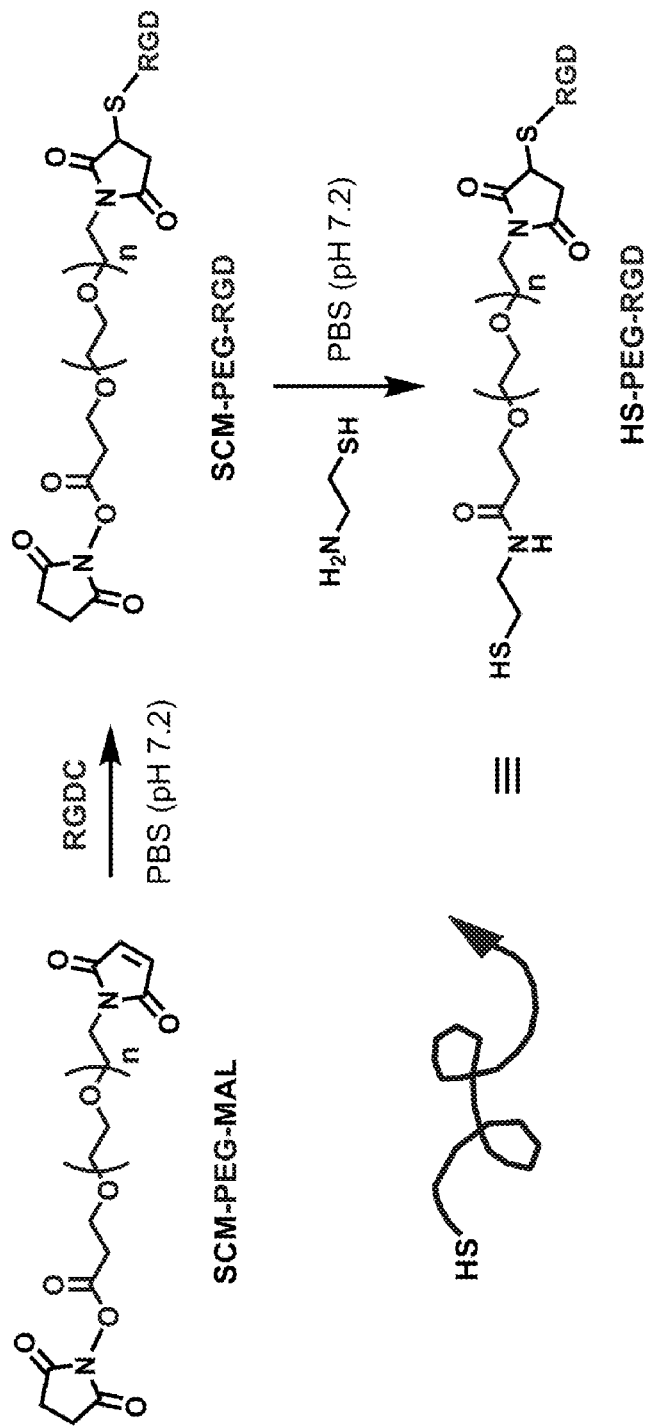
FIG. 45 shows the synthesis of HS-PEG-RGD from SCM-PEG-MAL and RGDC, and addition of 2-aminoethanethiol.

Synthesis of HS-PEG-RGD (FIG. 45)

To a solution of SCM-PEG-MAL (50.0 mg, 10.0 µmol, 1.0 equiv.) in 1 mL PBS (pH 7.2), a PBS buffer solution (10 mL) containing RGDC (22.5 mg, 50.0 µmol, 5.0 equiv.) was added to the reaction mixture. The reaction mixture was stirred at room temperature for 2 hrs. After the reaction, the 2-aminoethanethiol (3.9 mg, 50.0 µmol, 5.0 equiv.) was added to the reaction residue. The mixture was stirred for another 2 hrs at room temperature. The solution was then dialyzed with Slide-A-Lyzer® dialysis cassette (MWCO, 2 kD) against water overnight and lyophilized to give HS-PEG-RGD (31.0 mg, 5.4 µmol, a white powder in 62% yield. $^1$H NMR (400 MHz, DMSO-$d_6$): δ 7.03-8.84 (br, protons on RGD), 3.42-3.54 (br, protons on PEG and aminoethanethiol). MS (MALDI-TOF, positive mode, DHB): the observed Mn for SCM-PEG-MAL was 5373.49; the Mn value of HS-PEG-RGD based on the SCM-PEG-MAL was calculated as 5785.01 (M+H$^+$). found: 5785.29.

Figure 46:
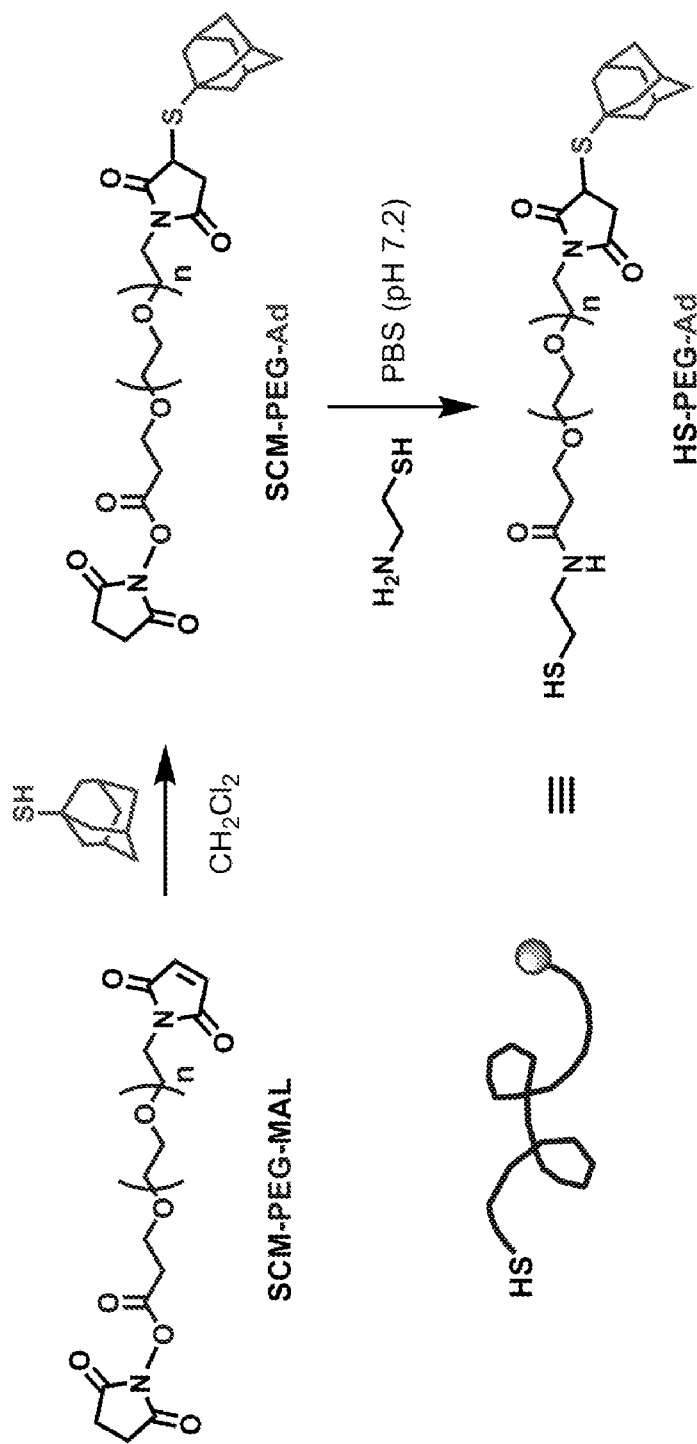
FIG. 46 shows the synthesis of HS-PEG-Ad from SCM-PEG-MAL and adamantane-1-thiol, and addition of 2-aminoethanethiol.

Synthesis of HS-PEG-Ad (FIG. 46)

To a solution of adamantane-1-thiol (8.4 mg, 50.0 µmol, 5.0 equiv.) in 1 mL $CH_2Cl_2$, SCM-PEG-MAL (50.0 mg, 10.0 µmol, 1.0 equiv.) was added slowly. The reaction mixture was stirred at room temperature for 1 h. After the reaction, the solvent was subsequently removed in vacuo, and the PBS buffer solution (10 mL) containing 2-aminoethanethiol (3.9 mg, 50.0 µmol, 5.0 equiv.) was added to the reaction residue. The mixture was stirred for another 2 hrs at room temperature, followed by the removal of insoluble adamantane-1-thiol by filtration. The solution was then dialyzed with Slide-A-Lyzer® dialysis cassette (MWCO, 2 kD) against water overnight and lyophilized to give HS-PEG-Ad (35.5 mg, 6.5 µmol), a white powder in 71% yield. $^1$H NMR (400 MHz, DMSO-$d_6$): δ 7.13-8.72 (br, protons on RGD), 3.43-3.64 (br, protons on PEG), 1.53-1.20 (br, protons on Ad). MS (MALDI-TOF, positive mode, DHB): the observed Mn for SCM-PEG-MAL was 5373.49; the Mn value of HS-PEG-Ad based on the SCM-PEG-MAL was calculated as 5503.60 (M+H$^+$). found: 5503.76.

Figure 47:
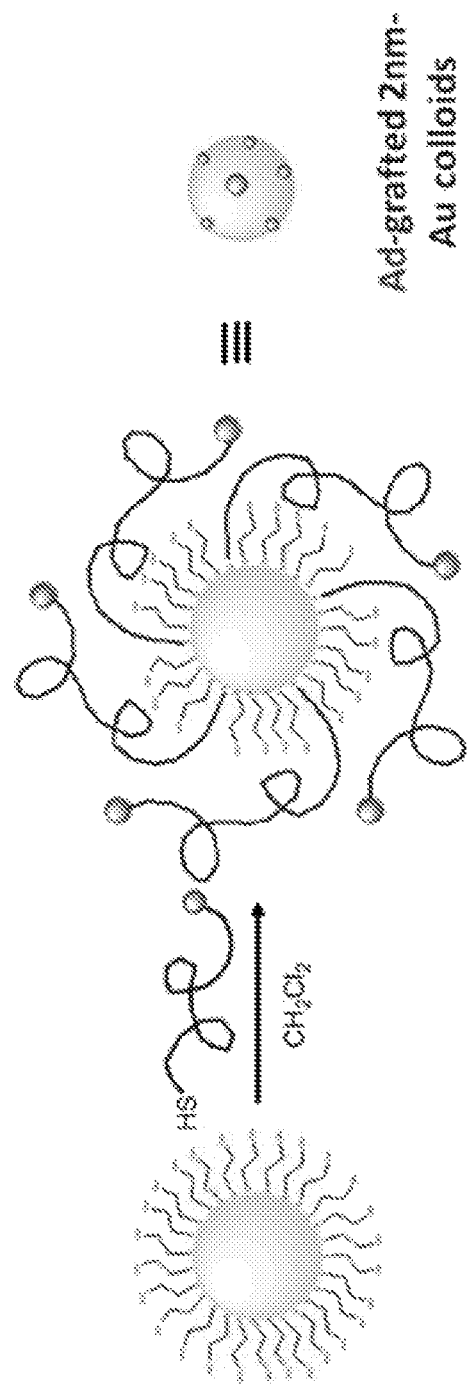
FIG. 47 shows the synthesis of Ad-grafted 2-nm Au colloids from 2-nm Au colloids and Ad-PEG-HS.

Synthesis of Ad-Grafted 2-nm Au Colloids (FIG. 47)

2-nm Au colloids were prepared by following the Brust-Schiffrin two-phase method using thioglycol as a capping ligand (Brust et al., *J. Chem. Soc. Chem. Comm.*, p. 801, 1994). A ligand exchange reaction was employed to produce Ad-grafted 2-nm Au colloids from 2-nm Au colloids (Ingram et al., *J. Am. Chem. Soc.*, vol. 119, p. 9175, 1997; Kim et al., *J. Am. Chem. Soc.*, vol. 131, p. 1360, 2009). 30 mg of 2-nm Au colloids were mixed with 10 mg of Ad-PEG-HS in $CH_2Cl_2$. The solution was stirred at room temperature for 24 hrs. The solvent was removed by rotary evaporator, and then the aggregates were washed with diethyl ether. Finally, Ad-grafted 2-nm Au colloids were obtained.

Figure 48:
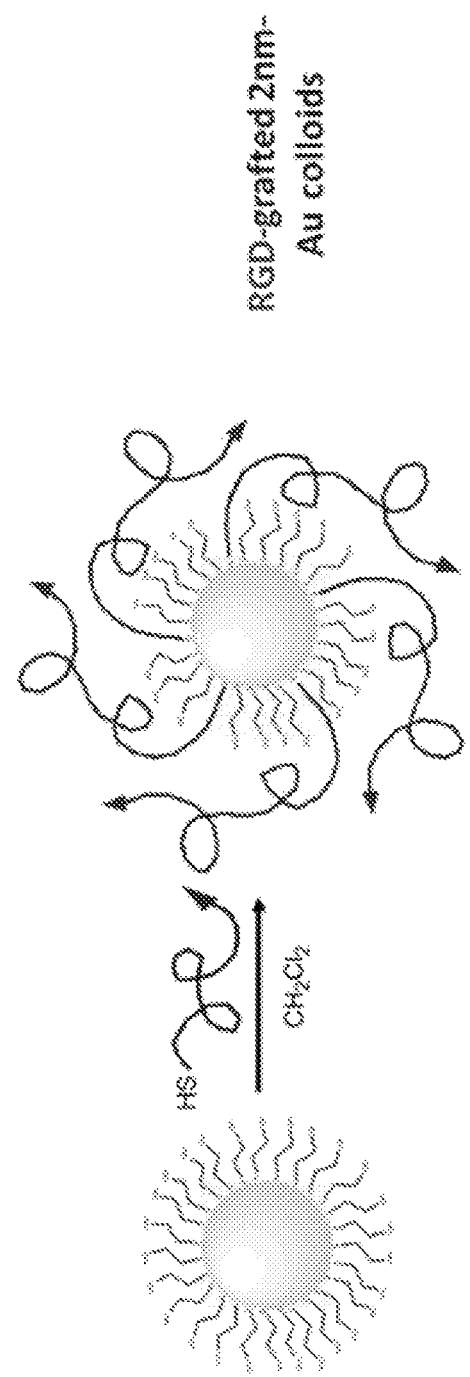
FIG. 48 shows the synthesis of RGD-grafted 2-nm Au colloids from 2-nm Au colloids and RGD-PEG-HS.

Synthesis of RGD-Grafted 2-nm Au Colloids (FIG. 48)

In order to incorporate targeted ligand, RGD-PEG-HS, onto the 2-nm Au colloids, a similar ligand exchange reaction was performed as mentioned above to obtain RGD-grafted 2-nm Au colloids.

Figure 49:
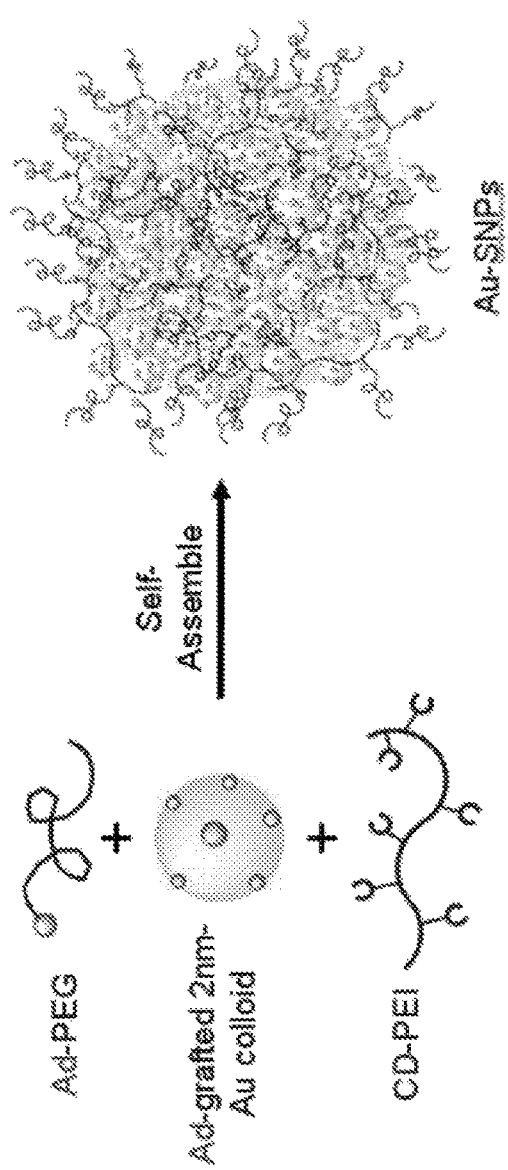
FIG. 49 shows the synthesis of Au-SNPs from Ad-PEG, Ad-grafted 2-nm Au colloid, and CD-PEI.

Synthesis of Au-SNPs (FIG. 49)

To a variable concentration of CD-PEI (0.145, 0.29, 0.57, 1.43, 2.87, 5.73 mg/ml) in 700 µL PBS buffer, 10 µL of Ad-grafted 2-nm Au colloids (3.2 mg/L) was slowly added. A 700-µL of PBS buffer containing Ad-PEG (6.3 mg) was sequentially added into the mixture to obtain a collection of Au-SNPs with different sizes range from 40 to 118 nm (40±5, 59±6, 78±5, 99±7, 118±23 nm) shown in FIG. 26.

Figure 50:
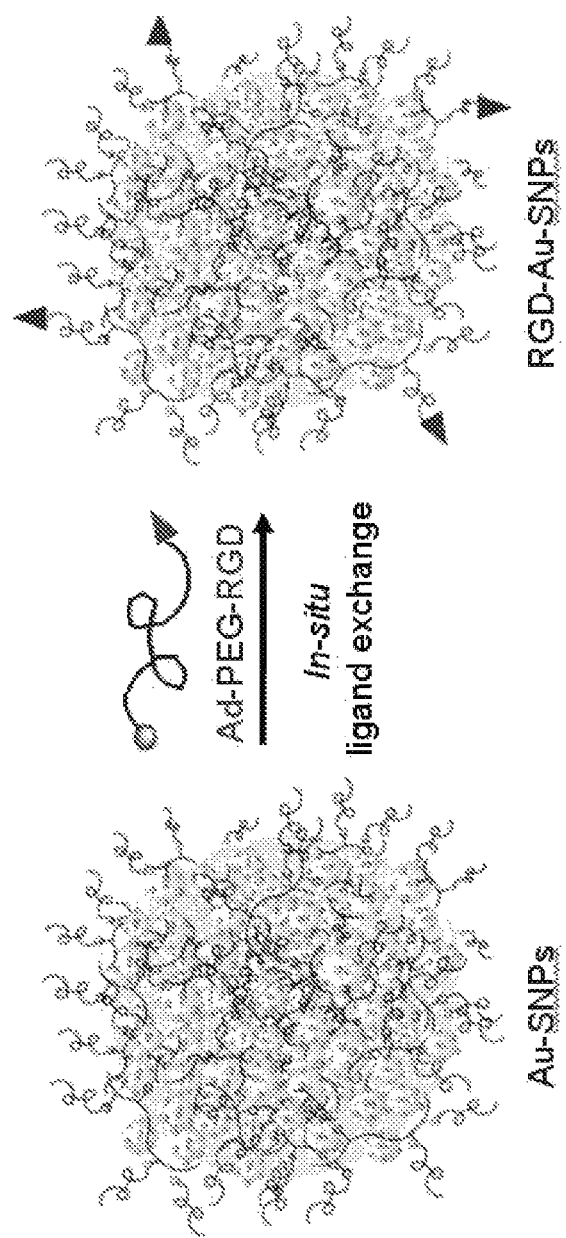
FIG. 50 shows the in-situ ligand exchange to obtain RGD-Au-SNPs from Au-SNPs and Ad-PEG-RGD.

In-Situ Ligand Exchange to Obtain RGD-Au-SNPs (FIG. 50)

In order to synthesize RGD-Au-SNPs, a convenient incorporation of targeting ligand, i.e., arginine-glycine-aspartic (RGD) peptide can be simply accomplished by in-situ RGD ligand exchange of the resulting Au-SNPs to give RGD-Au-SNPs with ligand coverage of 5 mol %.

Transmission Electron Microscopy

Figure 26:
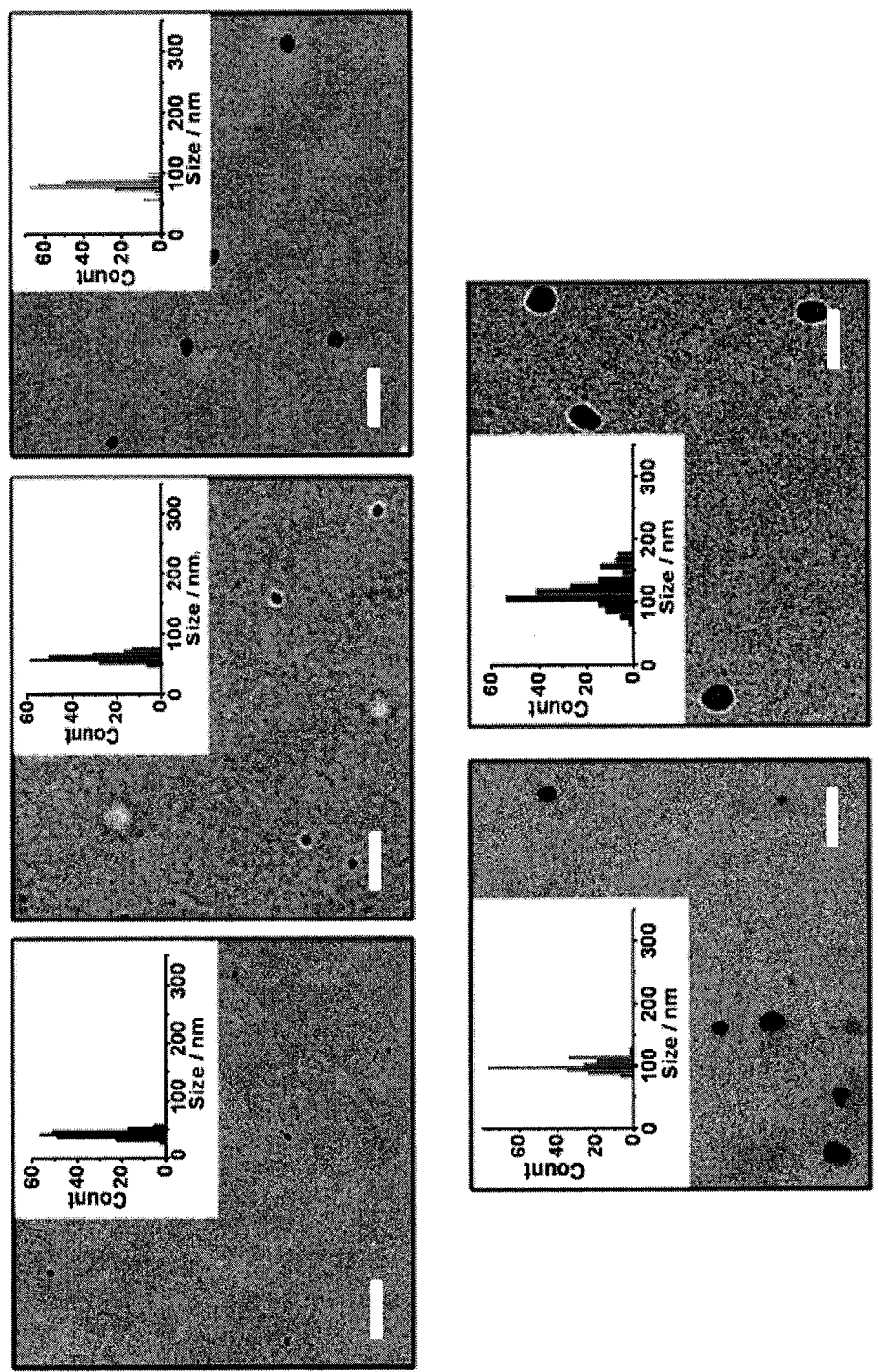
FIG. 26 shows TEM images and histograms of different sizes of Au-SNPs range from 40±5 nm, 59±6 nm, 78±5 nm, 99±7 nm, 118±23 nm. Scale bar: 300 nm.
Figure 27:
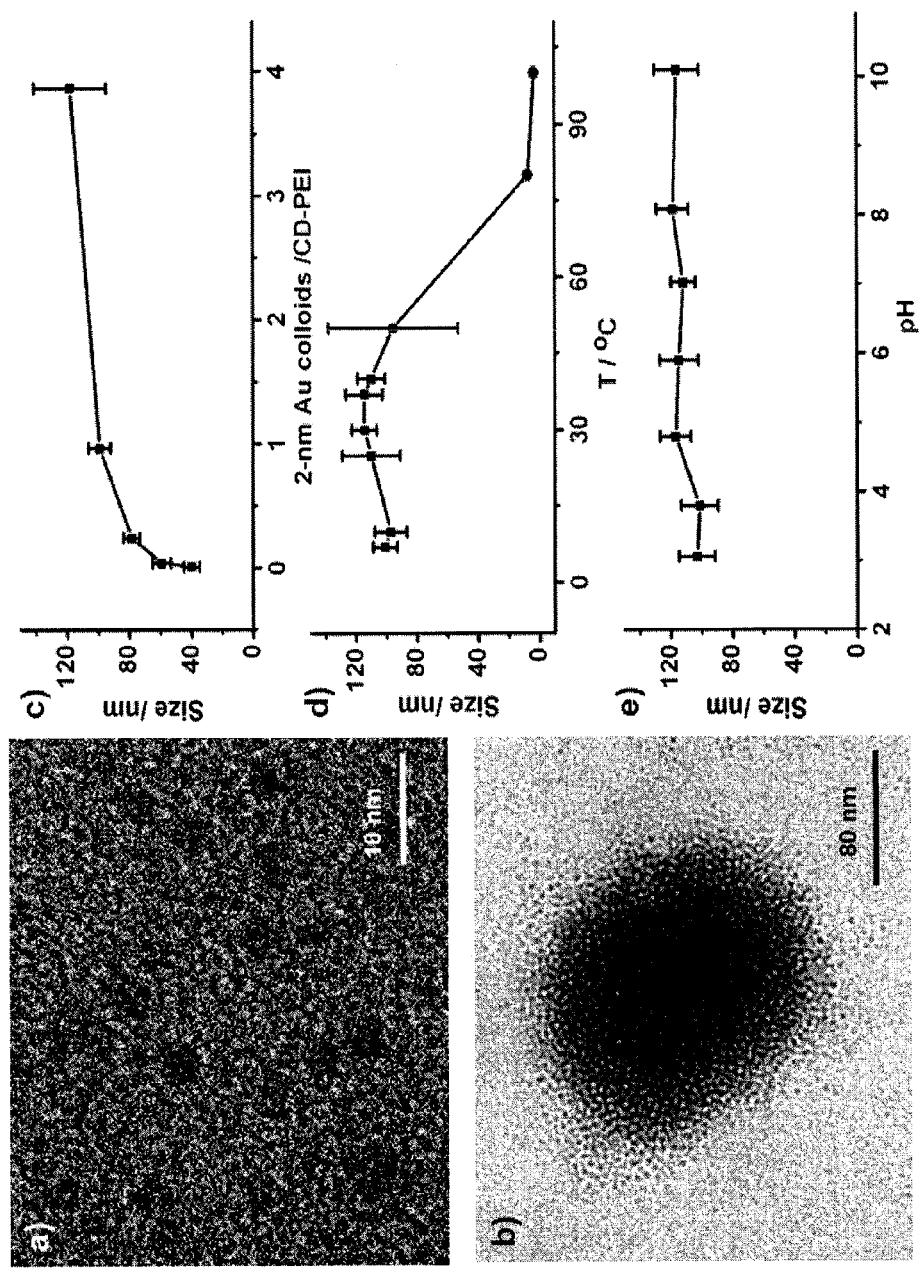
FIG. 27 shows transmission electron microscopy (TEM) images analysis.

The morphology and sizes of Au-SNPs were examined on a Philips CM 120 transmission electron microscope (TEM), operating at an acceleration voltage of 120 kV. The TEM samples were prepared by drop-coating 2 µL of Au-SNPs solutions onto carbon-coated copper grids. Excess amounts of droplets were removed by filter papers after 45 s. FIG. 26 shows a collection of Au-SNPs with the size ranging from 40 to 118 nm (40±5, 59±6, 78±5, 99±7, 118±23 nm). Note that their size distributions were obtained by measuring more than 200 Au-SNPs for each size. TEM images indicated that Au-SNPs exhibit spherical shapes with a narrow size distribution (FIG. 27B). FIG. 27B shows a typical and highly-magnified TEM image of single Au-SNP, where individual 2-nm Au colloids can be clearly visualized.

Zeta Potential

Figure 28:
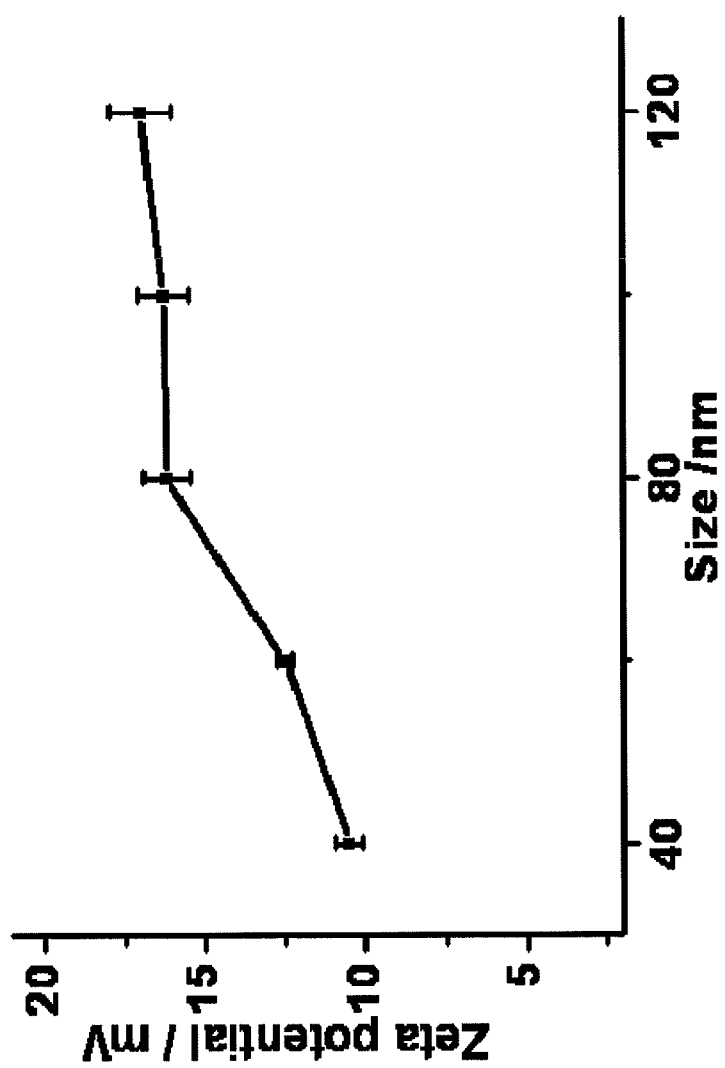
FIG. 28 shows size-dependent zeta potential variations of Au-SNPs in PBS buffer. Error bars are obtained from three independent measurements.

Zeta potentials of Au-SNPs were determined by photon correlation spectroscopy using a Zetasizer Nano instrument, (Malvern Instruments, Malvern, Worcestershire, UK). The measurements were performed at 25° C. with a detection angle of 90°, and the raw data were subsequently correlated to zeta potential by the Zetasizer software program. The zeta potentials were averaged by at least 3 measurements. Through multivalent Ad/CD recognition interactions, the ammonium groups in CD-PEI endow the Au-SNPs with positive charges. As the sizes of Au-SNPs increase, the charge increases from 10.5 to 17 mV (10.5±0.44, 12.5±0.25, 16.2±0.74, 16.3±0.76, 17±0.96 mV) shown in FIG. 28.

Stability

Since Au-SNPs were prepared via supramolecular assembly, the dynamic stabilities of the Au-SNPs were characterized at different environmental variables (temperature and pH), taking 118-nm Au-SNPs as an example. It is well-known that overall aggregates size from dynamic light scattering (DLS) measurement is much larger than the average size from TEM measurement, especially for inorganic nanoparticles (Shenhar et al., *Adv. Mater.*, vol. 17, p. 657, 2005). In this case, the size distribution of Au-SNPs from TEM measurements was employed to monitor size variation of Au-SNPs in PBS at temperature ranging from 7-100° C. (FIG. 27D) and at pH value from 3 to 10 (FIG. 27E). The results indicated that 118-nm Au-SNPs are stable in PBS at 7 to 40° C. and a pH value ranging from 5 to 10, suggesting that Au-SNPs can be used under physiological conditions. At higher temperatures (>50° C. in FIG. 29C), broader size distribution of Au-SNPs were observed by TEM. Complete disassembly of 118-nm Au-SNPs into 2 nm Au colloids can be attained when the temperature was increased to 100° C. The thermal disassembly of 118-nm Au-SNPs can be attributed to the weakened Ad/CD supramolecular interactions at an elevated temperature (Rekharsky et al., *Chem Rev*, vol. 98, p. 1875, 1998).

Stability of Au-SNPs Under Different Temperatures

Figure 29:
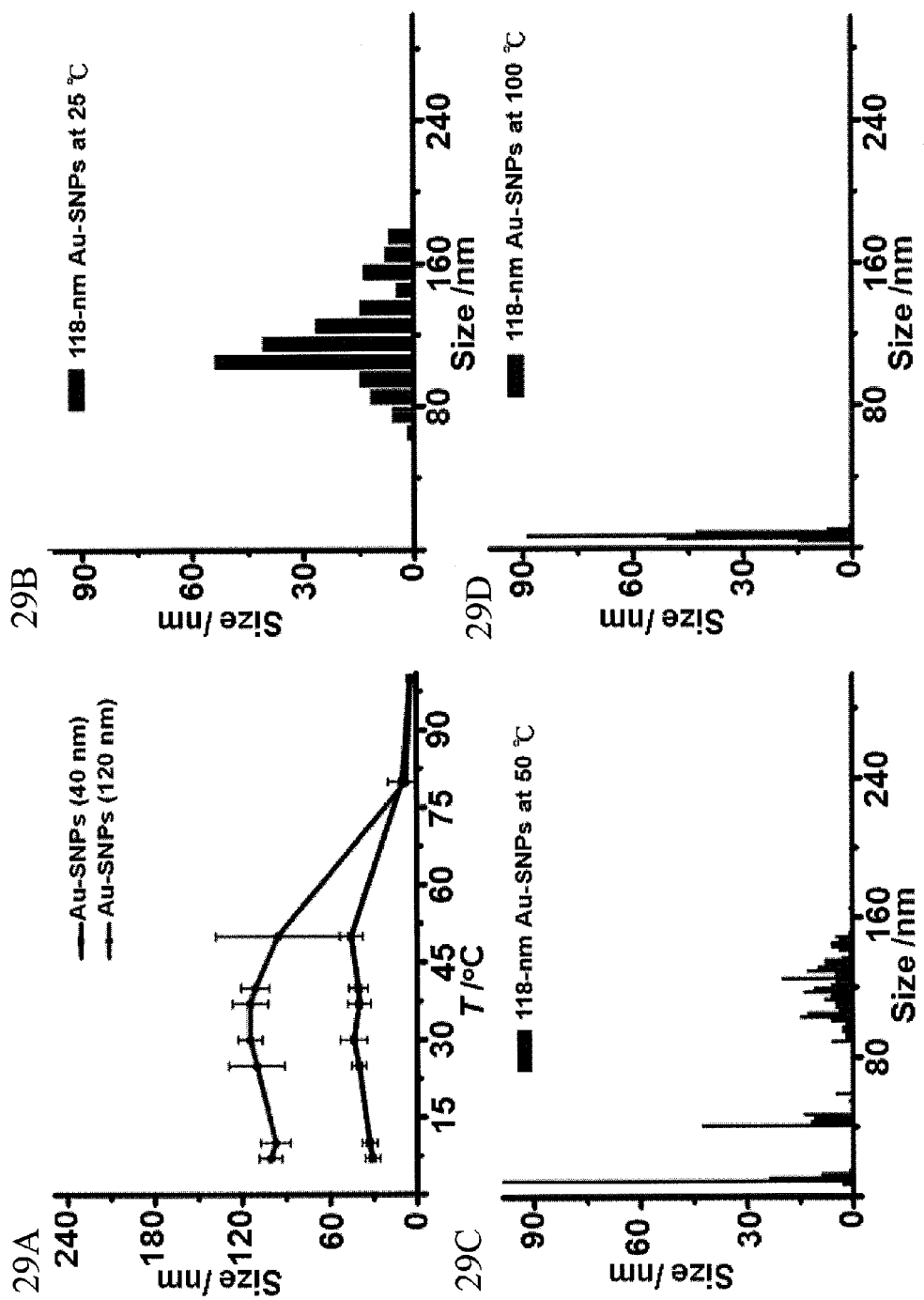
FIG. 29 shows the stability of Au-SNPs under different temperature.
Figure 30:
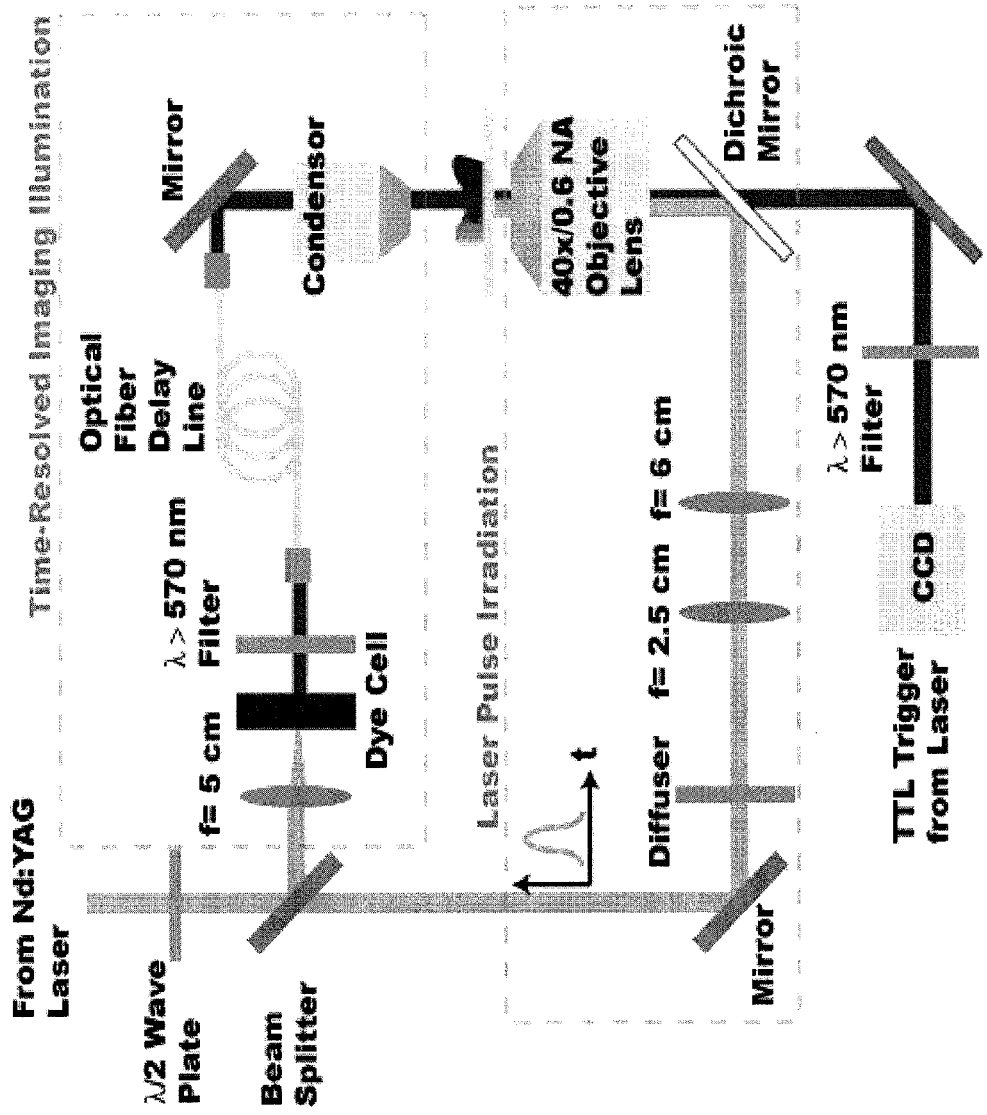
FIG. 30 shows an illustration of the pulse laser system setup.

To understand the thermal stability of the Au-SNPs, both 40 and 118-nm Au-SNPs solutions were placed in a water bath for 20 min. The studies were performed at different temperatures ranging from 7 to 100° C. Then the size variations of these Au-SNPs at different temperatures were measured by TEM and summarized in a plot (FIG. 29A). FIG. 29B is the TEM histogram of 118-nm Au-SNPs measured at 25° C. The histogram shows the size distribution of 118-nm Au-SNPs. When at a higher temperature (50° C.) in FIG. 29C, Au-SNPs started to disassemble into fragments with an average size of 40 nm. At 100° C., 118-nm Au-SNPs disassembled completely, and only ca. 2 nm Au colloids were observed (FIG. 29D). The results indicated that the Au-SNPs exhibited good thermal stability at the temperature range of 7 to 40° C.

Stability of Au-SNPs in Different pH Values

In order to understand Au-SNPs' characteristics under physiological conditions and their ability to provide a reasonable pH range for further experiments, the pH-dependent stability test of Au-SNPs was carried out by adding stock solutions of 40- and 118-nm Au-SNPs into different pH buffer solutions ranging from 0.9 to 10.1. The different pH buffer solutions were used as following: 100 mM HCl—KCl buffer (pH 0-2.0), 100 mM Glycine-HCl buffer (pH 2.2-3.6), 100 mM $CH_3COOH$—$CH_3COONa$ buffer (pH 3.7-5.6), 100 mM $Na_2HPO_4$—$NaH_2PO_4$ buffer (pH 5.8-8.0), 100 mM Tris-HCl buffer (pH 7.0-9.0) and 100 mM$Na_2CO_3$—$NaHCO_3$ buffer (pH 9.2-10.8). Typically, a 100-μL Au-SNPs stock solution in PBS (pH=7.2) was injected into 900-μL different pH buffer solutions. The resulting solutions were mixed and equilibrated for 10 min. Final pH values were determined by pH meter. Then the size variations of Au-SNPs solutions at different pH were measured by TEM. Note that each data point in the curve (FIG. 27E) was obtained by measuring more than 200 Au-SNPs. The results indicated that the Au-SNPs were stable at a pH range from 5 to 10.

Photothermal Ability

Cell Culture

U87 glioblastoma cell line ($2 \times 10^5$ cells/well) and MCF7 breast cancer cell line ($2 \times 10^5$ cells/well) were cultured on a 4-well Lab-Tek™ chamber slide in DMEM containing 10% fetal bovine serum (FBS) and 1% penicillin/streptomycin and EMEM containing 10% fetal bovine serum (FBS) and 1% penicillin/streptomycin, respectively. Cell cultures were maintained at 37° C. under a humidified condition with 5% $CO_2$. To help visually distinguish two different types of cells, the U87 and MCF7 cells were labeled with green and red fluorescent dyes (DiO and DiD cell-labeling solution, Invitrogen), respectively by using the suggested Experimental Protocol. After 24 hrs of plating, the cells were washed once with PBS, and the solutions of particles (including RGD-grafted 2-nm Au colloids, 118-nm Au-SNPs and 118-nm RGD-Au-SNPs) were added respectively. After 20 min of incubation, the cells were washed three times with PBS to remove extra solution and their individual culture medium was added followed by 2 hrs incubation. For the cell mixture experiment, a 1:1 cell mixture containing U87 cells and MCF7 cells was carried out under the similar treatment.

Pulsed Laser Irradiation

Scheme S8 illustrates the laser system setup applied in the microbubble studies. The laser source is a Q-switched, frequency-doubled Nd:YAG laser at 532 nm in wavelength and 6 ns in pulsewidth (Continuum, Minilite I). The laser beam is linearly polarized and the pulse energy can be adjusted using a variable attenuator consisting of a half wave plate and a polarizing beam splitter. The pulse energy was measured using a pyroelectric optical energy detector (Newport, 1918-C). The pulsed laser beam was directed into the epi fluorescence port of an inverted microscope (Zeiss, AxioObserver) and weakly focused through an objective lens (40×, 0.6 NA). The final laser spot diameter on the sample plane was 1 mm. A holographic diffuser (Edmund Optics, NT55-848) was placed in the beam path to reduce interference effects and smoothen the laser intensity profile.

Imaging Cavitation Microbubbles by Time-Resolved Imaging System

To capture the extremely short-lived cavitation microbubbles induced by the pulsed laser (typically with a lifetime <1 μs), a time-resolved imaging system was used. This included a high-speed Intensified CCD camera (Princeton Instrument, PI-MAXII), providing exposure times as short as 500 ps. A programmable delay between receiving the laser triggering signal and the camera shutter opening was set by the camera control unit. After the polarizing beam splitter, one arm of the laser beam was sent through a fluorescent dye cell (Exciton, LDS 698). The excited fluorescence pulse (wavelength centered around 698 nm) was coupled into a multimode fiber (Thorlabs, BFL37-600) and then sent through the microscope condenser to illuminate the sample, in synchronization with the camera shutter. A nanosecond time delay between the captured bubble image and the excitation laser pulse can be achieved by controlling the length of the optical fiber delay line.

Discussion

Figure 31:
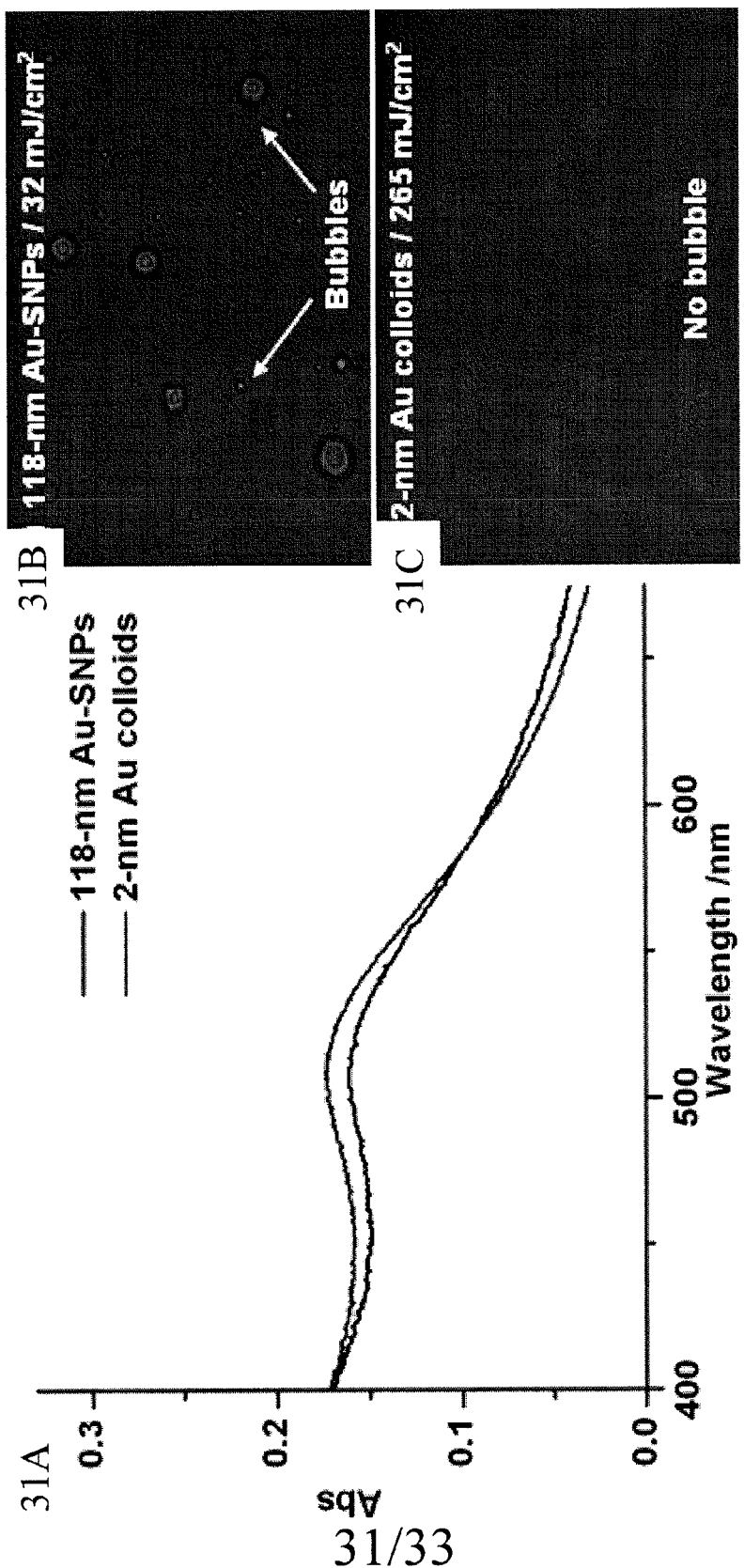
FIG. 31 shows optical features of Au-SNP.

To test feasibility of the Au-SNPs as a photothermal agent, 118-nm Au-SNPs were used as the model system. It is widely recognized that the diameter of nanoparticle therapeutics for cancer should be in the rough range of 10-120 nm (Davis et al., *Nature Rev. Drug Discov.*, vol. 7, p. 771-782, 2008). For comparison, 2-nm Au colloids were employed as a control. Firstly, UV-Vis spectroscopic measurements were performed to investigate the photophysical properties (FIG. 31A) of 118-nm Au-SNPs and 2-nm Au colloids. Given the characteristic surface plasmon resonance absorption of Au-SNPs and Au colloids (ranging between 500 to 530 nm) (Khlebtsov et al., *Nanotechnology*, vol. 17, p. 5167, 2006), a 532-nm green pulse laser was chosen to test their photothermal effects. Secondly, laser-induced microbubble generation studies were performed to monitor the locally accumulated heat of individual Au-SNPs. A broad range of energy density (3-265 mJ/cm$^2$) of a 532-nm pulse laser with 6-ns pulse duration were tested. Au-SNPs and Au colloid suspensions in PBS (with a normalized Au concentration 4.67 mg/mL) were irradiated by the laser with the variable energy. For 118-nm Au-SNPs, a laser threshold of 32 mJ/cm$^2$ was sufficient for generating microbubble (FIG. 31B) upon laser irradiation. In contrast, no microbubbles were observed for 2-nm Au colloid even under the maximum laser energy tested (265 mJ/cm$^2$, FIG. 31C). Again, the significant enhancement of the photothermal effects in 118-nm Au-SNPs can be attributed to the heat collective effect (Richardson et al., *Nano Lett*, vol. 9, p. 1139, 2009) in Au-SNPs. The formation of explosive vapor bubble on individual Au-SNPs requires an elevated local temperature higher than the critical temperature of the liquid medium (374° C. for water) (Kotaidis et al., *Appl Phys Lett*, vol. 87, 2005). Upon the formation of microbubbles, the localized accumulated heat may facilitate the thermal disassembly of Au-SNPs into smaller fragments, similar to what were observed in FIG. 27D. To monitor laser-induced Au-SNPs disassembly, a pulsed laser (with a 6-ns pulse duration) was employed to irradiate Au-SNPs at a repetition rate of 1 Hz. The microbubble formation was captured by the time-resolved imaging setup at 70 ns after the laser pulse arrival. A dramatic decrease of the laser-induced microbubbles was observed after several laser pulse irradiations, suggesting that most of Au-SNPs in the solution have thermally disassembled into smaller fragments which attenuates their photothermal characteristics (Huang et al., *Lasers Med Sci*, vol.

23, p. 217, 2008; Khlebtsov et al., *Nanotechnology*, vol. 17, p. 5167, 2006). In the following photothermal treatment studies, a fixed laser power of 120 mJ/cm$^2$ was employed to ensure the microbubble formation of 118-nm Au-SNPs.

Cell Targeting

Figure 32:
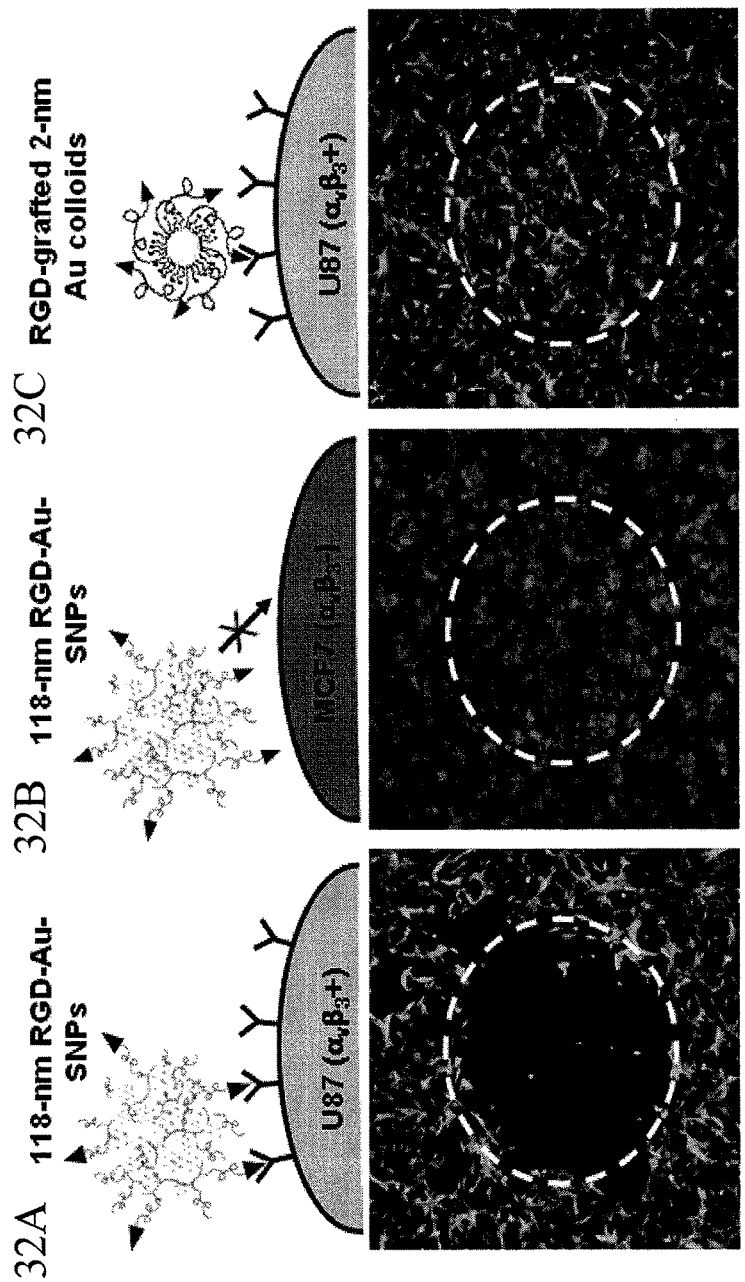
FIG. 32 shows fluorescence micrographs.

By incorporation of targeting ligands, Au nanostructure-based photothermal agents can be utilized for targeted photothermal treatment of certain types of cancer cells (Lapotko et al., *Laser Surg Med*, vol. 38, p. 631, 2006; Huang et al., *Langmuir*, vol. 24, p. 11860, 2008; Pitsillides et al., *Biophys J*, vol. 84, p. 4023, 2003; Wang et al., *Angew Chem Int Ed Engl*, vol. 48, p. 2759, 2009). In this study, the dynamic ligand exchange (adding 0.21 mg of Ad-PEG-RGD to 1.0 mL of 118-nm Au-SNPs solution (4.67 mg/mL) was employed to produce RGD-Au-SNPs which could recognize tumor cells with membrane $\alpha_v\beta_3$ integrin receptors (Liu et al., *Nat Nanotech*, vol. 2, p. 47, 2007). Along with the controls (i.e., RGD-grafted 2-nm Au colloids and non-targeting 118-nm Au-SNPs), 118-nm RGD-Au-SNPs were utilized to perform targeted photothermal treatment in 4-well chamber slides containing both $\alpha_v\beta_3$-positive U87 glioblastoma cells and $\alpha_v\beta_3$-negative MCF7 breast cancer cells. To help visually distinguish two different types of cells, the U87 and MCF7 cells were labeled with green and red fluorescent dyes (DiO and DiD cell-labeling solution, Invitrogen), respectively. After 20 min incubation with the three agents and subsequent replacement of culture media (to remove the free agents), the cells in the culture chambers were exposed to pulse laser irradiation (6 ns, 120 mJ/cm$^2$) with a beam diameter of 1 mm (determined by a photo mask). By maintaining the irradiated cells in an incubator (5% $CO_2$, 37° C.) for 2 hrs, the cells damaged by microbubble formation would detach from the substrates. An inverted fluorescence microscope (Nikon TE2000) was employed to examine the cells within the laser irradiated regions. As shown in FIG. 32A, cell detachment was observed for the RGD-Au-SNPs-treated U87 cells. In contrast, negligible cell detachment was observed for both RGD-Au-SNPs-treated MCF7 cells (FIG. 32B) and the two non-targeted Au-SNPs-treated cells. These results suggested that (i) RGD peptide confer target specificity to RGD-Au-SNPs, enabling photothermal treatment of $\alpha_v\beta_3$-positive U87 cells, and (ii) non-targeting Au-SNPs exhibit insignificant effects on cancer cells because that their surface-grafted PEG chains (Harris, *Poly(ethylene glycol) Chemistry: Biotechnical and Biomedical Applications*, Plemun Press, New York, 1992) are capable of reducing the nonspecific binding onto the cells. Further, there was undetectable cell detachment observed for the Au colloids-treated U87 cells (FIG. 32C), validating the previous observation that 2-nm Au colloids exhibit minute photothermal effects at the given pulse laser irradiation.

The selectivity of RGD-Au-SNPs for target-specific photothermal treatment was measured by targeted depletion of $\alpha_v\beta_3$-positive cells in a cell mixture containing both $\alpha_v\beta_3$-positive U87 and negative MCF7 cells. A 1:1 cell mixture (FIG. 33A) containing U87 cells and MCF7 cells was treated with RGD-Au-SNPs (4.67 mg/ml). After removal of free RGD-Au-SNPs, the cell mixture was irradiated by pulse laser. In the laser irradiated region, U87 cells were depleted, and the remaining MCF7 cells were able to be continuously cultured on the substrates. (FIG. 33A, right) It is noticeable, in the region outsides the laser footprint, both the positive and negative cells remained to be present. These results suggested that the photothermal treatment of RGD-Au-SNPs is highly selective to targeted cells. Besides the above mentioned specific targeting effects of RGD-Au-SNPs, the use of pulse laser generated effective photothermal effects in a defined location within a ns period, allowing localized cell damage in a spatial confined fashion. Unlike continuous wave radiations, a large area of cell damage was often observed as a result of heat diffusion in unconfined conditions from the targeted cells to surrounding medium over the relatively long period of light irradiation (O'Neal et al., *Cancer Lett*, vol. 209, p. 171, 2004).

Figure 33:
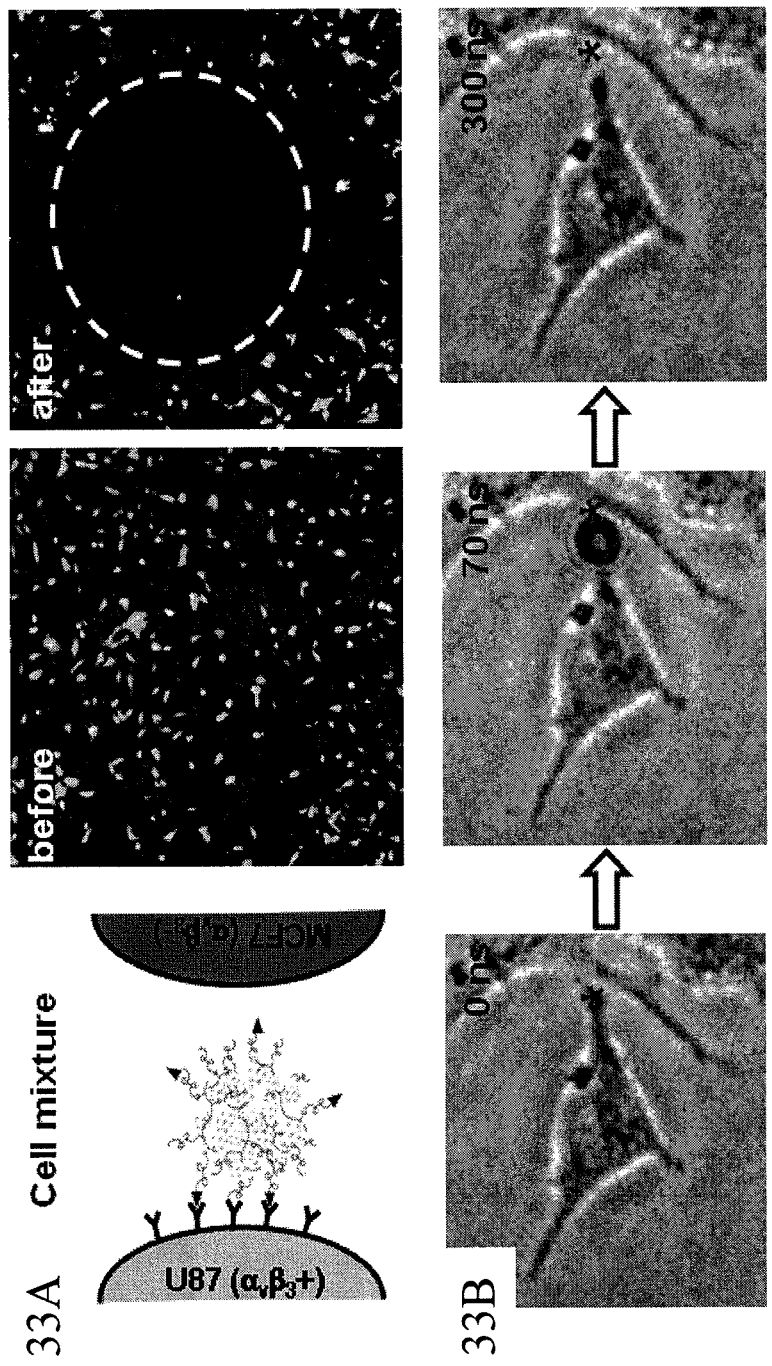
FIG. 33 shows photothermal treatment of a mixture of U87 and MCF7 cells.

It should be noted that the cell damage mechanism has to do with the mechanical destruction associated with the formation of explosive microbubbles, which is similar to those proposed for photothermal agents based on Au nanoparticles (Lapotko et al., *Laser Surg Med*, vol. 38, p. 631, 2006; Hleb et al., *Nanomed*, vol. 3, p. 647, 2008; Wu et al., *Optics Express*, 2009, in press) or carbon nanotubes (Kang et al., *Small*, vol. 5, p. 1292, 2009) but is dramatically different from the heating damage mechanism observed for the other photothermal agents (Huang et al., *Lasers Med Sci*, vol. 23, p. 217, 2008; Gobin et al., *Nano Lett*, vol. 7, p. 1929, 2007; Pitsillides et al., *Biophys J*, vol. 84, p. 4023, 2003; Huang et al., *J Am Chem Soc*, vol. 128, p. 2115, 2006). To visualize the microbubble-induced mechanical destruction (Hleb et al., *Nanomed*, vol. 3, p. 647, 2008) of the targeted cell, time-resolved imaging was conducted to monitor how a RGD-Au-SNP-grafted cell responded to microbubble formation right after laser irradiation. To ensure that a small number of RGD-Au-SNPs were grafted on the cells, the $\alpha_v\beta_3$-positive U87 cells were treated with a diluted concentration (0.93 mg/ml) of 118-nm RGD-Au-SNP. FIG. 33B shows the time-dependant response of RGD-Au-SNP-treated U87 cell to an irradiation of the 6-ns pulse laser (120 mJ/cm$^2$). After irradiation, a fast contraction of the cellular protrusion was observed as the result of the localized mechanical destruction caused by a microbubble.

In conclusion, the synthesis of size-controllable Au-SNPs from 2-nm Au colloids by utilizing a supramolecular self-assembly approach has be successfully demonstrated. The resulting Au-SNPs exhibited enhanced photothermal effects and may be utilized for demonstration of targeted photothermal treatment of subpopulation of cancer cells after incorporation of target-specific ligands (i.e., RGD). It is expected that (i) such a supramolecular assembly approach can be applied to assemble other "small" inorganic nanoparticles (e.g., superparamagnetic oxide nanoparticles (Lee et al., *Angew Chem Int Ed Engl*, vol. 45, p. 8160, 2006) for a broader application in materials science and biomedicine; (ii) a diversity of functional building blocks and therapeutic loads (e.g., DNAs, proteins and drugs) can be packaged into Au-SNPs, and laser-induced disassembly of Au-SNPs can be employed as a controlled release mechanism; and (iii) two-photon laser (Starkey et al., *Clin Cancer Res*, vol. 14, p. 6564, 2008) can be employed to overcome the tissue penetration limitation.

Conclusions

It is currently thought that the diameter of nanoparticle-based therapeutics for cancer should be in the range of 10-100 nm. The lower bound is based on the measurement of sieving coefficients for the glomerular capillary wall, as it is estimated that the threshold for first-pass elimination by the kidneys is 10 nm (Venturoli et al., *Am. J. Physiol*, vol. 288, pp. F605-F613, 2005). The upper bound on size is not as well defined at this time. The vasculature in tumors is known to be leaky to macromolecules. The lymph system of tumors in mouse models is poorly operational and macromolecules leaking from the blood vessels accumulate—a phenomenon known as "enhanced permeability and retention (EPR) effect" (Matsumura et al., *Cancer Res.*, vol. 6, pp.

6387-6392, 1986). Numerous lines of evidence suggest that this phenomenon is also operational in humans. It has been shown that entities in the order of hundreds of nanometer (nm) in size can leak out of the blood vessels and accumulate within tumors. However, large macromolecules or nanoparticles could have limited diffusion in the extracellular space (Dreher et al., *J. Natl Cancer Inst.*, vol. 98, pp. 335-344, 2006). Experiments from animal models suggest that sub-150 nm, neutral or slightly negatively charged entities can move through tumor tissue (Nomura et al., *Pharm Res.*, vol. 15, pp. 128-132, 1998). Additionally, recent data show that nanoparticles in the size range of 50-100 nm that carry a very slight positive charge can penetrate throughout large tumors, following systemic administration (Hu-Lieskovan et al., *Cancer Res.*, vol. 65, pp 8984-8992, 2005). Thus, well designed nanoparticles in the 10-100 nm size range and with a surface charge either slightly positive or slightly negative should have accessibility to and within disseminated tumors when they were dosed into the circulatory system. If this size range is correct, then these nanoparticles will be restricted from exiting normal vasculature (that requires sizes less than 1-2 nm); however they will still be able to access the liver, as entities up to 100-150 nm in diameter are able to do so.

Nanoparticle Surface Properties

Nanoparticles have high surface-to-volume ratios when compared with larger particles, and so control of their surface proper ties is crucial to their behavior in humans (Chen et al., *J Neurosurg*, vol. 103, pp. 311-319, 2005). The ultimate fate of nanoparticles within the body can be determined by the interactions of nanoparticles with their local environment, which depends on a combination of size and surface properties. Nanoparticles that are sterically stabilized (for example by polyethylene glycol (PEG) polymers on their surface) and have surface charges that are either slightly negative or slightly positive tend to have minimal self-self and self-non-self interactions. Also, the inside surface of blood vessels and the surface of cells contain many negatively charged components, which would repel negatively charged nanoparticles. As the surface charge becomes larger (either positive or negative), macrophage scavenging is increased and can lead to greater clearance by the reticulo endothelial system. Thus, minimizing nonspecific interactions by steric stabilization and control of surface charge helps to prevent nanoparticle loss to undesired locations. However, the complete removal of nonspecific interactions is not currently possible, and so there is always some particle loss; the key is to minimize these interactions as much as possible. If nanoparticle loss could be avoided, it would be expected that the distribution of the nanoparticles within a mammal would be uniform if no size restrictions existed on the basis of thermodynamic considerations. However, there are numerous size-restricted locations within the body that would create non-uniformity. For example, the brain is protected by the blood-brain barrier, which has severe size and surface property limitations for entrance. By understanding the size and surface property requirements for reaching specified sites within the body, localization of nanoparticles to these sites may be accomplished.

Nanoparticle with Targeting Ligands.

The introduction of targeting ligands that provide specific nanoparticle-cell surface interactions can play a critical role in controlling the delivery specificity of the nanoparticle. For example, nanoparticles can be targeted to cancer cells if their surfaces contain moieties such as peptides, proteins or antibodies. These moieties can interact with cancer cell surface receptor proteins, such as transferrin receptors, that are known to be increased in number on a wide range of cancer cells (Gaffer et al., *J. Clin. Pathol.*, vol. 36, pp. 539-545, 1983). These targeting ligands enable nanoparticles to first bind to cell-surface receptors and enter cells by receptor-mediated endocytosis. Recent work comparing non-targeted and targeted nanoparticles (lipid-based (Kirpotin et al., *Cancer Res.*, vol. 66, pp. 6732-6740, 2006) or polymer-based (Bartlett et al., *Proc. Natl. Acad Sci. USA*, vol. 104, pp. 15549-15554, 2007) has shown that the primary role of the targeting ligands is to enhance cellular uptake into cancer cells rather than increasing the accumulation in the tumor.

Distinguishing Features of Nanoparticle Therapeutics for Cancer.

Nanoparticles can be tuned to provide long or short circulation times by careful control of size and surface properties. Also, they can be directed to specific cell types within target organs (for example, hepatocytes versus Kupffer cells in the liver (Popielarski et al., *Bioconjug Chem.*, vol. 16, pp. 1071-1080, 2005). While other types of cancer therapeutics such as molecular conjugates (for example, antibody-drug conjugates) can also meet these minimum specifications, targeted nanoparticles have at least five features that distinguish them from other therapeutic modalities for cancer. First, nanoparticles can carry a large payload of drug entity and protect it from degradation. For example, a 70 nm nanoparticle can contain approximately 2,000 small interfering RNA (siRNA) molecules (Bartlett et al., *Bioconjug Chem.*, vol. 18, pp. 456-468, 2007), whereas antibody conjugates carry fewer than ten (Song et al., *Nature Biotech.*, vol. 23, pp. 709-717, 2005). These high payload amounts can also be achieved with other drug types such as small-molecule or peptide drugs. Furthermore, nanoparticle payloads are located within the particle, and their type and number do not affect the pharmacokinetic properties and biodistribution of the nanoparticles. This is unlike molecular conjugates in which the type and number of therapeutic entities conjugated to the targeting ligand (such as an antibody) significantly modifies the overall properties of the conjugate. Second, the nanoparticles are sufficiently large to contain multiple targeting ligands that can allow multivalent binding to cell-surface receptors (Hong, *Chem Biol.*, vol. 14, pp. 107-115, 2007). Nanoparticles have two parameters for tuning the binding to target cells: the affinity of the targeting moiety and the density of the targeting moiety. The multivalency effects can lead to high effective affinities when using arrangements of low-affinity ligands (Hong, *Chem Biol.*, vol. 14, pp. 107-115, 2007; Montet et al., *J. Med. Chem*, vol. 49, pp. 6087-6093, 2006; Carlson et al., *ACS Chem. Biol.*, vol. 2, pp. 119-127, 2007). Thus, the repertoire of molecules that can be used as targeting agents is greatly expanded as many low-affinity ligands that are not sufficient for use as molecular conjugates can now be attached on nanoparticles to create higher affinity via multivalent binding to cell-surface receptors. Third, nanoparticles are sufficiently large to accommodate multiple types of drug molecules. Numerous therapeutic interventions can be simultaneously applied with a nanoparticle in a controlled manner. As mentioned in the first point, the fact that the pharmacokinetic properties of the nanoparticle are not modified by the amount of the therapeutic also holds true with multiple types of the therapeutics being combined together within the nanoparticles. Fourth, the release kinetics of drug molecules from nanoparticles can be tuned to match the mechanism of action. For example, topoisomerase I inhibitors such as the camptothecin-based chemotherapeutic drugs are reversible binders of the enzyme. So, the mechanism of action for camptothecin-based drugs on the topoisomerase I enzyme suggests enhanced efficacy with prolonged exposure of the drug (Pommier, *Curr. Med. Chem. Anticancer Agents*, vol. 4, pp. 429-434, 2004), making a slow release from the nanoparticles most desirable. With siRNA, the gene inhibition kinetics are greatly influenced by cell cycle times (Bartlett et al., *Nucl. Acid Res.*, vol. 34, pp. 322-333, 2006; Bartlett et al., *Biotech. Bioeng.*, vol. 97, pp. 909-921, 2007), and for uses in cancer there may not be a need for slow release of the therapeutic agent. Fifth, nanoparticles may have the potential to bypass multidrug resistance mechanisms that involve cell-surface protein pumps (for example, glycoprotein P), as they enter cells via endocytosis. Overall, it seems that controlled combination of these features through nanoparticle design could minimize side effects of anticancer drugs while enhancing efficacy, and clinical results are emerging that suggest that this promise is starting to be realized.

Nanoparticles as Anticancer Agents

Liposomes (~100 nm and larger) carrying chemotherapeutic small-molecule drugs have been approved for cancer since the mid-1990s, and are mainly used to solubilize drugs, leading to biodistributions that favor higher uptake by the tumor than the free drug (Zamboni, *Clin. Cancer Res*, vol. 11, pp. 8230-8234, 2005). However, liposomes do not provide control for the time of drug release, and in most cases do not achieve effective intracellular delivery of the drug molecules (Zamboni, *Clin. Cancer Res*, vol. 11, pp. 8230-8234, 2005), therefore limiting their potential to be useful against multidrug resistant cancers. An example is Doxil (ortho biotech), a PEG-liposome containing the cytotoxic drug doxorubicin. Doxil was originally approved for the treatment of AIDS-related Kaposi's sarcoma and is now approved for use in ovarian cancer and multiple myeloma. This agent circulates in the body as a nanoparticle and has a half-life-100-times longer than free doxorubicin. Its primary advantage in the clinic is the reduction in cardiotoxicity over that of doxorubicin (Rahman et al., *Int. J. Nanomedicine*, vol. 2, pp. 567-583, 2007; Batist, *Cardiovasc. Toxicol.*, vol. 7, pp. 72-74, 2007). However, such nanoscale systems have also shown that unwanted attributes can manifest themselves. For example, although Doxil has been shown to have reduced cardiotoxicity compared with free doxorubicin, it also has skin toxicity that is not observed with the drug alone (Uziely, *J. Clin. Oncol*, vol. 13, pp. 1777-1785, 1995). Newer nanoparticle systems, as defined by a higher degree of multi-functionality (incorporating features such as slow release and/or targeting ligands), have enhanced features such as reduced toxicity without the emergence of other toxicities compared with the initial approved products.

Nanoparticles without Targeting Ligands

Several nanoparticle-based therapeutics (e.g., liposomes, polymer micelles and polymer-based nanoparticles) with the drug molecules that they carry are compared. In each case—for example, doxorubicin compared with the doxorubicin-carrying nanoparticles SP1049C, NK911 and Doxil—the nanoparticle alters the pharmacokinetic properties of the drug molecule. Clearance is a common pharmacokinetic parameter that is readily available from clinical trials, and it is a better indicator of differences in circulation times among the therapeutics. Dramatically reduced clearances have been obtained with nanoparticles such as Doxil, XYoTAX (CT-2103) and IT-101. The longer circulation times of the nanoparticles compared with the free drug alone can improve tumor uptake (Boddy, *Clin. Cancer Res.*, vol. 11, pp. 7834-7840, 2005). Moreover, polymeric micelles (sub-100 nm) have been shown to accumulate more readily in tumors than the larger liposomes (Sutton et al., *Pharm. Res.*, vol. 24, pp. 1029-1046, 2007). Therefore, careful control of size will be important to the pharmacokinetics, biodistribution, tumor accumulation and tumor penetration of the nanoparticle therapeutic. Some of the nanoparticles that are now in clinical testing also have mechanisms to control the release of the drug, as discussed below with IT-101. These methodologies are based on cleavage of a chemical bond between the particle and the drug by hydrolysis; by enzymes that are located within and outside cells, e.g., lysozymes and esterases; or by enzymes that are located only within cells, e.g., cathepsin.

Nanoparticles with Targeting Ligands

The nanoparticles utilize passive targeting to reach tumors. That is, it is thought that the leaky vasculature of tumors allows the nanoparticles to extravasate, whereas the normal vasculature does not (this property is involved in the altered biodistribution of nanoparticles compared with the drug molecule). Ultimately, active targeting via the inclusion of a targeting ligand on the nanoparticles is envisioned to provide the most effective therapy. The few ligand-targeted therapeutics that are either approved or in the clinic. PK2 (FCE28069), a HPMA-polymer-Gly-Phe-leu-Gly-doxorubicin conjugate that also contain the sugar galactosamine, was the first ligand-targeted nanoparticle to reach the clinic. The galactose-based ligand was used to target the asialoglycoprotein receptor (ASGPR), which is expressed on hepatocytes, in the hope that its high expression is retained on primary liver cancer cells. At present, the only targeted nanoparticles in the clinic are MbP-426, which contains the cytotoxic platinumbased drug oxaliplatin in a liposome; SGT-53, a liposome containing a plasmid coding for the tumor suppressor p53; and CAIAA-01, a polymer-siRNA composite. CAIAA-01 is a targeted nanoparticle that has high drug (siRNA) payload per targeting ligand, proven multivalent binding to cancer cell surfaces and an active drug (siRNA) release mechanism that is triggered upon the recognition of intracellular localization by pH ecline below a value of 6.0 (which occurs in the endocytic pathway) (Heidel et al., *Proc. Natl. Acad. Sci. USA*, vol. 104, pp. 5715-5721, 2007). As mentioned above, recent work comparing non-targeted and targeted nanoparticles has shown that the primary role of the targeting ligands is to enhance cellular uptake into cancer cells and to minimize the accumulation in normal tissue. This behavior suggests that the colloidal properties of nanoparticles will determine their biodistribution, whereas the targeting ligand serves to increase the intracellular uptake in the target tumor. If this turns out to be the case in general, then the targeting ligand affinity and surface density on the nanoparticle will determine cellular uptake.

Supramolecular Nanoparticles

Different from the conventional chemical synthesis capable of making/breaking covalent bonds, supramolecular chemistry, combining two basic concepts—self assembly and molecular recognition—offers a powerful and convenient tool for preparation of nanostructured materials from molecular building blocks (Meyer et al., *Chem. Soc. Rev.*, vol. 36, p. 1705, 2007; Hwang et al., *Angew. Chem.*, vol. 119, p. 214, 2007; Hwang et al., *Angew. Chem. Int. Ed*, vol. 46, p. 210, 2007; Ludden et al., *Chem. Soc. Rev.*, vol. 35, p. 1122, 2006; Park et al., *Nature*, vol. 451, p. 553, 2008; Stoddart et al., *Proc. Natl. Acad. Sci. USA*, vol. 99, p. 4797, 2002; Liu et al., *Angew. Chem.*, vol. 116, p. 2744, 2004; Liu et al., *Angew. Chem. Int. Ed.*, vol. 43, p. 2690, 2004). The fact is that the concept of self assembly has been extensively used to prepare organic nanoparticles. For instance, liposomes and nanoscale vesicles (Torchilin, *Nat. Rev. Drug Discov.*, vol. 4, p. 145, 2005) with bi-layered membranes (Li et al., *Advanced Drug Delivery Reviews*, vol. 60, pp. 1000-1017, 2008), which are prepared through self-assembly of phospholipids, can serve as powerful nano-vehicles for drug and gene delivery Self-aggregation of amphiphilic block water soluble copolymers forms nanoparticles, which can be utilized for drug delivery and molecular imaging (Sun, *Advanced Materials*, vol. 19, p. 3157, 2007; Ferreira et al., *Cell stem cell*, vol. 3, pp. 136-146, 2008; Bull et al., *Nano Letters*, vol. 5, pp. 1-4, 2005; Bertin, et al., *Journal of the American Chemical Society*, vol. 128, pp. 4168-4169, 2006). However, the concept of molecular recognition seems to be an underappreciated strength which could be applied for producing organic nanoparticles and unique properties of the resulting nanoparticles.

β-Cyclodextrin (CD) is one of the most commonly used supramolecular building blocks (Wenz et al., *Chemical Reviews*, vol. 106, pp. 782-817, 2006). CD molecules feature a hydrophilic/biocompatible external wall and a hydrophobic internal binding pocket. The external walls of the CDs confer desired hydrophilicity and biocompatibility to the CD-based supramolecular structures, thus enabling a diversity of biomedical applications (Li et al., *Advanced Drug Delivery Reviews*, vol. 60, pp. 1000-1017, 2008). A guest molecule (i.e., adamantane (Ad) or its derivatives) with suitable size and hydrophobicity can be included into the internal binding pocket of a CD through their hydrophobic interactions in aqueous solution, allowing a convenient, flexible and modular synthetic approach for preparation of functional supramolecular materials (Ludden et al., *Chemical Society Reviews*, vol. 35, pp. 1122-1134, 2006). CD-containing cationic polymers have been employed as vectors for highly efficient delivery of siRNA. Through the CD/Ad recognition, Ad-functionalized PEG chains were grated onto the nanoparticles to enable biocompatibility long systemic circulation in vivo (Bartlett et al., *Proc Natl Acad Sci USA*, vol. 104, pp. 15549-15554, 2007).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

We claim:

1. A self-assembled supramolecular nanoparticle (SNP), comprising:
    a plurality of binding components, each having a plurality of binding regions, wherein the plurality of binding regions comprises β-cyclodextrin;
    a plurality of cores that are suitable to at least provide some mechanical structure to said self-assembled supramolecular nanoparticle, wherein each of said plurality of cores is one of an organic core or an inorganic core, which comprises at least one core binding element adapted to bind to the binding regions to form a first inclusion complex, wherein the core binding element comprises adamantane, and wherein the first inclusion complex is adamantane-β-cyclodextrin; and
    a plurality of terminating components, each having a single terminating binding element that binds to remaining binding regions of one of said plurality of binding components by forming a second inclusion complex, wherein the single terminating binding element comprises adamantane, and wherein the second inclusion complex is adamantane-β-cyclodextrin;
    wherein said plurality of cores and said plurality of binding components self assemble when brought into contact to form said self-assembled supramolecular nanoparticle, and
    wherein said plurality of terminating components act to occupy the remaining binding regions of said plurality of binding components, and said plurality of terminating components are present in a sufficient quantity relative to said plurality of binding regions of said plurality of binding components to terminate further binding, thereby forming a discrete particle, and
    wherein the discrete particle is a member of a monodisperse population having a size of at least about 30 nm and less than about 500 nm.

2. A self-assembled supramolecular nanoparticle according to claim 1, wherein at least one of the cores further comprises at least one element selected from a light emitting compound, a compound having a radioactive or magnetically active isotope, a targeting ligand that targets at least one cell surface proteins, and a cell permeation ligand.

3. A self-assembled supramolecular nanoparticle according to claim 2, wherein the at least one element is a targeting ligand that targets at least one cell surface proteins, wherein the targeting ligand is selected from the group consisting of an antibody, an oligonucleotide, a polypeptide, and a small molecule.

4. A self-assembled supramolecular nanoparticle according to claim 3, wherein the at least one element is a cell permeation ligand.

5. A self-assembled supramolecular nanoparticle according to claim 2, wherein the targeting ligand is selected from the group consisting of RGD, EGF, folic acid, transferrin, and antibodies for targeting cell surface markers.

6. A self-assembled supramolecular nanoparticle according to claim 1, comprising at least two different terminating components.

7. A self-assembled supramolecular nanoparticle according to claim 1, further comprising a cargo, wherein the cargo is encapsulated within the supramolecular nanoparticle.

8. A self-assembled supramolecular nanoparticle according to claim 7 wherein said cargo is a therapeutic compound; siRNA; peptide; oligonucleotide; or plasmid.

9. A self-assembled supramolecular nanoparticle according to claim 7 wherein said cargo is a therapeutic compound or plasmid.

10. A self-assembled supramolecular nanoparticle according to claim 1, wherein said inorganic core comprises at least one of gold nanoparticles, magnetic nanoparticles, quantum dots, silica nanoparticles or semiconductive oxides.

11. A self-assembled supramolecular nanoparticle according to claim 1, wherein said organic core comprises at least one of dendrimers, polymers, micelles, liposomes or vesicles.

12. A self-assembled supramolecular nanoparticle according to claim 1, wherein said organic core comprises at least one of a dendrimer, branched polyethyleneimine, linear polyethyleneimine, polylysine, polylactide, polylactide-co-glycolide, polyanhydrides, poly-ε-caprolactones, polymethyl methacrylate, poly(N-isopropyl acrylamide) or polypeptides.

13. A self-assembled supramolecular nanoparticle according to claim 12, wherein said organic core comprises a dendrimer.

14. A self-assembled supramolecular nanoparticle according to claim 1, wherein said plurality of terminating components comprises at least one of polyethylene glycol, polymer, polypeptide, or oligosaccharide.

15. A self-assembled supramolecular nanoparticle according to claim 1, wherein the binding component further comprises at least one element selected from the group consisting of a light emitting compound, a compound having a radioactive or magnetically active isotope, a targeting ligand that targets at least one cell surface proteins, and a cell permeation ligand.

16. A self-assembled supramolecular nanoparticle according to claim 15, wherein the one or more elements is a targeting ligand that targets at least one cell surface proteins, or a cell permeation ligand.

17. A self-assembled supramolecular nanoparticle according to claim 1, wherein the terminating component further comprises at least one element selected from the group consisting of a light emitting compound, a compound having a radioactive or magnetically active isotope, a targeting ligand that targets at least one cell surface proteins, and a cell permeation ligand.

18. A self-assembled supramolecular nanoparticle according to claim 17, wherein the at least one element is a targeting ligand that targets at least one cell surface proteins, or a cell permeation ligand.

19. A self-assembled supramolecular nanoparticle according to claim 1, wherein the structural components are selected from the group consisting of 4-Ad-PAMAM, 8-Ad-PAMAM, and Ad-grafted 2-nm Au colloids.

20. A self-assembled supramolecular nanoparticle according to claim 1, wherein the binding components are selected from the group consisting of CD-PEI, CD-PEI-DOTA, and 6-Mono-tosy-β-cyclodextrin (6-OTs-β-CD).

21. A self-assembled supramolecular nanoparticle according to claim 1, wherein the terminating components are selected from the group consisting of Ad-PEG, RGD-PEG-Ad, and TAT-PEG-Ad.

22. A self-assembled supramolecular nanoparticle according to claim 1, wherein the binding components further comprise a polymer, an oligosaccharide, or a polypeptide.

23. A self-assembled supramolecular nanoparticle according to claim 1, wherein the binding components further comprise polyethylene imine or poly-L-lysine.

* * * * *